(12) United States Patent
Levine et al.

(10) Patent No.: US 8,882,698 B2
(45) Date of Patent: *Nov. 11, 2014

(54) ANTI-OBESITY DEVICES

(75) Inventors: Andy H. Levine, Newton, MA (US);
David A. Melanson, Hudson, NH (US);
John C. Meade, Mendon, MA (US)

(73) Assignee: GI Dynamics, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/430,949

(22) Filed: Mar. 27, 2012

(65) Prior Publication Data

US 2012/0184967 A1 Jul. 19, 2012

Related U.S. Application Data

(60) Continuation of application No. 11/635,890, filed on Dec. 8, 2006, now Pat. No. 8,486,153, which is a division of application No. 11/541,616, filed on Oct. 2, 2006, now Pat. No. 7,766,861, which is a division of application No. 10/726,011, filed on Dec. 2, 2003, now Pat. No. 7,122,058.

(60) Provisional application No. 60/512,145, filed on Oct. 17, 2003.

(51) Int. Cl.
*A61M 5/00* (2006.01)
*A61B 17/04* (2006.01)
(Continued)

(52) U.S. Cl.
CPC ....... *A61F 5/0076* (2013.01); *A61F 2002/9528* (2013.01); *A61B 17/0401* (2013.01);
(Continued)

(58) Field of Classification Search
CPC ............... A61F 5/00; A61F 2/95; A61F 2/07; A61F 2002/9511; A61F 2002/9665; A61F 2002/9505; A61M 25/00
USPC .............. 604/8, 104, 198, 194, 191; 606/108, 606/194, 198; 623/1.15, 1.17, 1.11, 23.65, 623/1.12, 1.2
See application file for complete search history.

(56) References Cited

U.S. PATENT DOCUMENTS

| | | | |
|---|---|---|---|
| 1,899,781 | A | 2/1933 | Twiss |
| 2,464,933 | A | 3/1949 | Kaslow |

(Continued)

FOREIGN PATENT DOCUMENTS

| | | |
|---|---|---|
| DE | 33 26 061 A1 | 2/1984 |
| EP | 0 480 667 B1 | 4/1992 |

(Continued)

OTHER PUBLICATIONS

Bethge, N., et al., "Human tissue responses to metal stents implanted in vivo for the palliation of malignant stenoses," *Gastrointestinal Endoscopy* 43(6):596-602 (1996).

(Continued)

*Primary Examiner* — Philip R Wiest
*Assistant Examiner* — Ariana Zimbouski
(74) *Attorney, Agent, or Firm* — Hamilton, Brook, Smith & Reynolds, P.C.

(57) ABSTRACT

Method and apparatus for limiting absorption of food products in specific parts of the digestive system is presented. A gastrointestinal implant device is anchored in the pyloric portion of the gastrointestinal system and extends beyond the ligament of Treitz. All food exiting the stomach is funneled through the device. The gastrointestinal device includes an anchor for anchoring the device in the pyloric portion and a flexible sleeve that extents into the duodenum. The anchor is collapsible for endoscopic delivery and removal.

33 Claims, 56 Drawing Sheets

(51) Int. Cl.
    *A61B 17/11*    (2006.01)
    *A61F 5/00*     (2006.01)
    *A61F 2/95*         (2013.01)
    *A61F 2/04*         (2013.01)
    *A61F 2/90*         (2013.01)
    *A61B 17/00*        (2006.01)
    *A61F 2/848*        (2013.01)
    *A61F 2/07*         (2013.01)
    *A61B 17/06*        (2006.01)

(52) U.S. Cl.
    CPC .. *A61F 2220/0016* (2013.01); *A61F 2002/045* (2013.01); *A61B 17/1114* (2013.01); *A61F 2002/044* (2013.01); *A61F 2/04* (2013.01); *A61F 2/90* (2013.01); *A61B 2017/00867* (2013.01); *A61B 17/0469* (2013.01); *A61F 2/848* (2013.01); *A61F 2002/075* (2013.01); *A61F 2/95* (2013.01); *A61F 2250/0039* (2013.01); *A61B 17/0482* (2013.01); *A61F 2/07* (2013.01); *A61F 2002/8486* (2013.01); *A61F 2002/8483* (2013.01); *A61F 5/0089* (2013.01); *A61B 2017/00238* (2013.01); *A61B 2017/0419* (2013.01); *A61B 2017/061* (2013.01)
    USPC .............. 604/8; 604/83; 604/84; 606/108; 23/1.11; 23/1.15; 23/1.17; 23/23.65

(56) References Cited

U.S. PATENT DOCUMENTS

| | | | |
|---|---|---|---|
| 3,780,740 A | 12/1973 | Rhea | |
| 4,133,315 A | 1/1979 | Berman et al. | |
| 4,134,405 A | 1/1979 | Smit | |
| 4,246,893 A | 1/1981 | Berson | |
| 4,265,694 A | 5/1981 | Boretos et al. | |
| 4,270,542 A | 6/1981 | Plumley | |
| 4,271,827 A | 6/1981 | Angelchik | |
| 4,279,251 A | 7/1981 | Rusch | |
| 4,315,509 A * | 2/1982 | Smit | 606/108 |
| 4,341,218 A * | 7/1982 | U | 606/195 |
| 4,403,604 A | 9/1983 | Wilkinson et al. | |
| 4,416,267 A | 11/1983 | Garren et al. | |
| 4,501,264 A | 2/1985 | Rockey | |
| 4,580,568 A | 4/1986 | Gianturco | |
| 4,607,618 A | 8/1986 | Angelchik | |
| 4,617,932 A | 10/1986 | Kornberg | |
| 4,641,653 A | 2/1987 | Rockey | |
| 4,648,383 A | 3/1987 | Angelchik | |
| 4,763,653 A | 8/1988 | Rockey | |
| 4,768,507 A | 9/1988 | Fischell et al. | |
| 4,823,808 A | 4/1989 | Clegg et al. | |
| 4,846,836 A | 7/1989 | Reich | |
| 4,878,905 A | 11/1989 | Blass | |
| 4,905,693 A | 3/1990 | Ravo | |
| 4,913,141 A * | 4/1990 | Hillstead | 623/1.11 |
| 4,991,594 A | 2/1991 | Angelchik | |
| 5,035,706 A | 7/1991 | Giantureo et al. | |
| 5,037,387 A | 8/1991 | Quinn et al. | |
| 5,041,126 A | 8/1991 | Gianturco | |
| 5,057,091 A | 10/1991 | Andersen | |
| 5,059,166 A | 10/1991 | Fischell et al. | |
| 5,104,399 A | 4/1992 | Lazarus | |
| 5,123,917 A | 6/1992 | Lee | |
| 5,135,516 A | 8/1992 | Sahatjian et al. | |
| 5,152,756 A | 10/1992 | Quinn et al. | |
| 5,152,782 A | 10/1992 | Kowligi et al. | |
| 5,176,617 A | 1/1993 | Fischell et al. | |
| 5,190,561 A | 3/1993 | Graber | |
| 5,226,429 A | 7/1993 | Kuzmak | |
| 5,236,423 A | 8/1993 | Mix et al. | |
| 5,254,133 A | 10/1993 | Seid | |
| 5,279,553 A | 1/1994 | Winkler et al. | |
| 5,282,824 A | 2/1994 | Gianturco | |
| 5,290,294 A | 3/1994 | Cox et al. | |
| 5,306,300 A | 4/1994 | Berry | |
| 5,314,444 A | 5/1994 | Gianturco | |
| 5,314,472 A | 5/1994 | Fontaine | |
| 5,314,473 A | 5/1994 | Godin | |
| 5,318,530 A | 6/1994 | Nelson, Jr. | |
| 5,322,501 A | 6/1994 | Mahmud-Durrani | |
| 5,330,500 A | 7/1994 | Song | |
| 5,364,353 A | 11/1994 | Corfitsen et al. | |
| 5,387,235 A | 2/1995 | Chuter | |
| 5,389,090 A | 2/1995 | Fischell et al. | |
| 5,401,241 A | 3/1995 | Delany | |
| 5,405,378 A | 4/1995 | Strecker | |
| 5,417,697 A | 5/1995 | Wilk et al. | |
| 5,423,851 A | 6/1995 | Samuels | |
| 5,443,498 A | 8/1995 | Fontaine | |
| 5,456,713 A | 10/1995 | Chuter | |
| 5,480,423 A | 1/1996 | Ravenscroft et al. | |
| 5,492,530 A | 2/1996 | Fischell et al. | |
| 5,507,767 A | 4/1996 | Maeda et al. | |
| 5,507,771 A | 4/1996 | Gianturco | |
| 5,540,713 A * | 7/1996 | Schnepp-Pesch et al. ... | 623/1.18 |
| 5,562,697 A | 10/1996 | Christiansen | |
| 5,569,219 A | 10/1996 | Hakki et al. | |
| 5,605,530 A | 2/1997 | Fischell et al. | |
| 5,607,442 A | 3/1997 | Fischell et al. | |
| 5,611,787 A | 3/1997 | Demeter et al. | |
| 5,620,763 A | 4/1997 | House et al. | |
| 5,624,430 A | 4/1997 | Eton et al. | |
| 5,630,797 A | 5/1997 | Diedrich et al. | |
| 5,634,928 A | 6/1997 | Fischell et al. | |
| 5,639,274 A | 6/1997 | Fischell et al. | |
| 5,643,312 A | 7/1997 | Fischell et al. | |
| 5,662,713 A | 9/1997 | Andersen et al. | |
| 5,665,064 A | 9/1997 | Bodicky et al. | |
| 5,669,932 A | 9/1997 | Fischell et al. | |
| 5,690,642 A | 11/1997 | Osborne et al. | |
| 5,693,084 A | 12/1997 | Chuter | |
| 5,695,516 A | 12/1997 | Fischell et al. | |
| 5,697,971 A | 12/1997 | Fischell et al. | |
| 5,713,948 A | 2/1998 | Uflacker | |
| 5,715,832 A | 2/1998 | Koblish et al. | |
| 5,718,973 A | 2/1998 | Lewis et al. | |
| 5,720,776 A | 2/1998 | Chuter et al. | |
| 5,722,984 A | 3/1998 | Fischell et al. | |
| 5,730,698 A | 3/1998 | Fischell et al. | |
| 5,733,325 A | 3/1998 | Robinson et al. | |
| 5,735,859 A | 4/1998 | Fischell et al. | |
| 5,735,892 A | 4/1998 | Myers et al. | |
| 5,741,292 A * | 4/1998 | Mendius | 606/191 |
| 5,743,874 A | 4/1998 | Fischell et al. | |
| 5,749,825 A | 5/1998 | Fischell et al. | |
| 5,749,848 A * | 5/1998 | Jang et al. | 604/509 |
| 5,755,777 A | 5/1998 | Chuter | |
| 5,759,174 A | 6/1998 | Fischell et al. | |
| 5,772,668 A | 6/1998 | Summers et al. | |
| 5,776,186 A | 7/1998 | Uflacker | |
| 5,792,144 A | 8/1998 | Fischell et al. | |
| 5,792,172 A | 8/1998 | Fischell et al. | |
| 5,800,456 A | 9/1998 | Maeda et al. | |
| 5,800,526 A | 9/1998 | Anderson et al. | |
| 5,820,584 A | 10/1998 | Crabb | |
| 5,824,041 A | 10/1998 | Lenker et al. | |
| 5,824,058 A | 10/1998 | Ravenscroft et al. | |
| 5,830,229 A | 11/1998 | Konya et al. | |
| 5,840,009 A | 11/1998 | Fischell et al. | |
| 5,843,164 A | 12/1998 | Frantzen et al. | |
| 5,855,601 A | 1/1999 | Bessler et al. | |
| 5,876,445 A | 3/1999 | Andersen et al. | |
| 5,879,282 A | 3/1999 | Fischell et al. | |
| 5,879,370 A | 3/1999 | Fischell et al. | |
| 5,895,391 A | 4/1999 | Farnholtz | |
| 5,910,145 A | 6/1999 | Fischell et al. | |
| 5,913,895 A | 6/1999 | Burpee et al. | |
| 5,919,233 A | 7/1999 | Knopf et al. | |
| 5,925,063 A | 7/1999 | Khosravi | |
| 5,925,076 A | 7/1999 | Inoue | |
| 5,935,161 A | 8/1999 | Robinson et al. | |
| 5,962,620 A | 10/1999 | Reich et al. | |

(56) References Cited

U.S. PATENT DOCUMENTS

| | | | |
|---|---|---|---|
| 5,964,771 | A | 10/1999 | Beyar et al. |
| 5,976,153 | A | 11/1999 | Fischell et al. |
| 5,984,964 | A * | 11/1999 | Roberts et al. ............... 623/1.11 |
| 6,013,019 | A | 1/2000 | Fischell et al. |
| 6,013,085 | A | 1/2000 | Howard |
| 6,025,044 | A | 2/2000 | Campbell et al. |
| 6,027,508 | A | 2/2000 | Ren et al. |
| 6,027,526 | A | 2/2000 | Limon et al. |
| 6,074,673 | A | 6/2000 | Guillen |
| 6,077,297 | A | 6/2000 | Robinson et al. |
| 6,086,604 | A | 7/2000 | Fischell et al. |
| 6,099,552 | A | 8/2000 | Adams |
| 6,102,887 | A | 8/2000 | Altman |
| 6,120,533 | A | 9/2000 | Fischell |
| 6,120,534 | A | 9/2000 | Ruiz |
| 6,146,323 | A | 11/2000 | Fischell |
| 6,152,956 | A | 11/2000 | Pierce |
| 6,179,868 | B1 | 1/2001 | Burpee et al. |
| 6,187,016 | B1 | 2/2001 | Hedges et al. |
| 6,190,403 | B1 | 2/2001 | Fischell et al. |
| 6,200,336 | B1 | 3/2001 | Pavcnik et al. |
| 6,221,043 | B1 | 4/2001 | Fischell et al. |
| 6,221,102 | B1 | 4/2001 | Baker et al. |
| 6,241,757 | B1 | 6/2001 | An et al. |
| 6,245,097 | B1 | 6/2001 | Inoue |
| 6,251,064 | B1 | 6/2001 | Silverman et al. |
| 6,251,132 | B1 | 6/2001 | Ravenscroft et al. |
| 6,254,629 | B1 | 7/2001 | Inoue |
| 6,270,521 | B1 | 8/2001 | Fischell et al. |
| 6,293,960 | B1 | 9/2001 | Ken |
| 6,302,891 | B1 | 10/2001 | Nadal |
| 6,302,917 | B1 | 10/2001 | Dua et al. |
| 6,315,708 | B1 | 11/2001 | Salmon et al. |
| 6,322,538 | B1 | 11/2001 | Elbert et al. |
| 6,331,190 | B1 | 12/2001 | Shokoohi et al. |
| 6,332,877 | B1 | 12/2001 | Michels |
| 6,355,056 | B1 | 3/2002 | Pinheiro |
| 6,356,782 | B1 | 3/2002 | Sirimanne et al. |
| 6,375,660 | B1 | 4/2002 | Fischell et al. |
| 6,383,214 | B1 | 5/2002 | Banas et al. |
| 6,387,114 | B2 | 5/2002 | Adams |
| 6,401,718 | B1 | 6/2002 | Johnson et al. |
| 6,402,779 | B1 | 6/2002 | Colone et al. |
| 6,406,792 | B1 | 6/2002 | Briquet et al. |
| 6,428,558 | B1 | 8/2002 | Jones et al. |
| 6,450,989 | B2 | 9/2002 | Dubrul et al. |
| 6,458,074 | B1 | 10/2002 | Matsui et al. |
| 6,468,298 | B1 | 10/2002 | Pelton |
| 6,485,409 | B1 | 11/2002 | Voloshin et al. |
| 6,485,515 | B2 | 11/2002 | Strecker |
| 6,508,833 | B2 | 1/2003 | Pavcnik et al. |
| 6,514,282 | B1 | 2/2003 | Inoue |
| 6,520,985 | B1 | 2/2003 | Burpee et al. |
| 6,524,335 | B1 | 2/2003 | Hartley et al. |
| 6,524,336 | B1 | 2/2003 | Papazolgou et al. |
| 6,530,951 | B1 | 3/2003 | Bates et al. |
| 6,537,247 | B2 | 3/2003 | Shannon |
| 6,540,775 | B1 | 4/2003 | Fischell et al. |
| 6,540,789 | B1 | 4/2003 | Silverman et al. |
| 6,544,291 | B2 | 4/2003 | Taylor |
| 6,547,817 | B1 | 4/2003 | Fischell et al. |
| 6,558,400 | B2 | 5/2003 | Deem et al. |
| 6,558,429 | B2 | 5/2003 | Taylor |
| 6,565,597 | B1 | 5/2003 | Fearnot et al. |
| 6,572,646 | B1 | 6/2003 | Boylan et al. |
| 6,582,460 | B1 | 6/2003 | Cryer |
| 6,589,213 | B2 | 7/2003 | Reydel |
| 6,589,275 | B1 | 7/2003 | Ivancev et al. |
| 6,623,518 | B2 | 9/2003 | Thompson et al. |
| 6,635,069 | B1 | 10/2003 | Teoh et al. |
| 6,635,079 | B2 | 10/2003 | Unsworth et al. |
| 6,645,239 | B1 | 11/2003 | Park et al. |
| 6,652,555 | B1 | 11/2003 | VanTassel et al. |
| 6,656,194 | B1 | 12/2003 | Gannoe et al. |
| 6,656,212 | B2 | 12/2003 | Ravenscroft et al. |
| 6,669,722 | B2 | 12/2003 | Chen et al. |
| 6,675,809 | B2 | 1/2004 | Stack et al. |
| 6,676,692 | B2 | 1/2004 | Rabkin et al. |
| 6,695,875 | B2 | 2/2004 | Stelter et al. |
| 6,699,263 | B2 | 3/2004 | Cope |
| 6,699,278 | B2 | 3/2004 | Fischell et al. |
| 6,706,061 | B1 | 3/2004 | Fischell et al. |
| 6,716,240 | B2 | 4/2004 | Fischell et al. |
| 6,736,840 | B2 | 5/2004 | Fischell et al. |
| 6,740,121 | B2 | 5/2004 | Geitz |
| 6,755,869 | B2 | 6/2004 | Geitz |
| 6,764,518 | B2 | 7/2004 | Godin |
| 6,773,440 | B2 | 8/2004 | Gannoe et al. |
| 6,776,791 | B1 | 8/2004 | Stallings et al. |
| 6,802,868 | B2 | 10/2004 | Silverman et al. |
| 6,821,291 | B2 | 11/2004 | Bolea et al. |
| 6,845,776 | B2 | 1/2005 | Stack et al. |
| 6,855,159 | B1 | 2/2005 | Tanner et al. |
| 6,860,901 | B1 | 3/2005 | Baker et al. |
| 6,918,871 | B2 * | 7/2005 | Schulze ........................ 600/114 |
| 6,926,658 | B2 * | 8/2005 | Farnan ............................. 600/3 |
| 6,936,065 | B2 | 8/2005 | Khan et al. |
| 6,960,233 | B1 | 11/2005 | Berg et al. |
| 6,989,024 | B2 | 1/2006 | Hebert et al. |
| 7,011,654 | B2 | 3/2006 | Dubrul et al. |
| 7,011,671 | B2 | 3/2006 | Welch |
| 7,011,673 | B2 | 3/2006 | Fischell et al. |
| 7,025,791 | B2 | 4/2006 | Levine et al. |
| 7,037,327 | B2 | 5/2006 | Salmon et al. |
| 7,037,344 | B2 | 5/2006 | Kagan et al. |
| 7,066,951 | B2 | 6/2006 | Chobotov |
| 7,081,132 | B2 | 7/2006 | Cook et al. |
| 7,087,088 | B2 | 8/2006 | Berg et al. |
| 7,121,283 | B2 | 10/2006 | Stack et al. |
| 7,122,058 | B2 | 10/2006 | Levine et al. |
| 7,146,984 | B2 | 12/2006 | Stack et al. |
| 7,152,607 | B2 | 12/2006 | Stack et al. |
| 7,160,312 | B2 | 1/2007 | Saadat |
| 7,175,660 | B2 | 2/2007 | Cartledge et al. |
| 7,211,114 | B2 | 5/2007 | Bessler et al. |
| 7,220,237 | B2 | 5/2007 | Gannoe et al. |
| 7,220,284 | B2 | 5/2007 | Kagan et al. |
| 7,267,694 | B2 | 9/2007 | Levine et al. |
| 7,314,489 | B2 | 1/2008 | McKenna et al. |
| 7,329,285 | B2 | 2/2008 | Levine et al. |
| 7,335,224 | B2 | 2/2008 | Øhlenschlaeger |
| 7,338,520 | B2 | 3/2008 | Bailey et al. |
| 7,347,875 | B2 | 3/2008 | Levine et al. |
| 7,354,454 | B2 | 4/2008 | Stack et al. |
| 7,476,256 | B2 | 1/2009 | Meade et al. |
| 7,507,218 | B2 | 3/2009 | Aliski et al. |
| 7,611,528 | B2 | 11/2009 | Goodson, IV et al. |
| 7,678,068 | B2 | 3/2010 | Levine et al. |
| 7,682,330 | B2 | 3/2010 | Meade et al. |
| 7,758,535 | B2 | 7/2010 | Levine et al. |
| 7,766,861 | B2 * | 8/2010 | Levine et al. ................... 604/57 |
| 7,785,361 | B2 | 8/2010 | Nikolchev et al. |
| 7,803,177 | B2 | 9/2010 | Hartley et al. |
| 7,815,671 | B2 | 10/2010 | Wright et al. |
| 7,981,163 | B2 | 7/2011 | Meade et al. |
| 8,092,510 | B2 | 1/2012 | Metcalf et al. |
| 8,303,669 | B2 | 11/2012 | Meade et al. |
| 8,333,797 | B2 | 12/2012 | Goodson et al. |
| 8,486,153 | B2 | 7/2013 | Levine et al. |
| 8,579,954 | B2 | 11/2013 | Licata |
| 2001/0020190 | A1 | 9/2001 | Taylor |
| 2002/0022853 | A1 | 2/2002 | Swanson et al. |
| 2002/0032487 | A1 | 3/2002 | Dua et al. |
| 2002/0065545 | A1 | 5/2002 | Leonhardt et al. |
| 2002/0091439 | A1 | 7/2002 | Baker et al. |
| 2002/0147489 | A1 | 10/2002 | Hong et al. |
| 2002/0151953 | A1 | 10/2002 | Chobotov et al. |
| 2002/0155100 | A1 | 10/2002 | Kieffer et al. |
| 2002/0183768 | A1 | 12/2002 | Deem et al. |
| 2002/0183786 | A1 | 12/2002 | Girton |
| 2002/0188344 | A1 | 12/2002 | Bolea et al. |
| 2002/0193828 | A1 | 12/2002 | Griffin et al. |
| 2003/0032941 | A1 | 2/2003 | Boyle et al. |
| 2003/0040804 | A1 | 2/2003 | Stack et al. |

(56) References Cited

U.S. PATENT DOCUMENTS

| | | |
|---|---|---|
| 2003/0040808 A1 | 2/2003 | Stack et al. |
| 2003/0050684 A1 | 3/2003 | Abrams et al. |
| 2003/0069539 A1 | 4/2003 | Gandhi et al. |
| 2003/0109892 A1 | 6/2003 | Deem et al. |
| 2003/0109931 A1 | 6/2003 | Geitz |
| 2003/0109935 A1 | 6/2003 | Geitz |
| 2003/0120265 A1 | 6/2003 | Deem et al. |
| 2003/0149467 A1 | 8/2003 | Linder et al. |
| 2003/0153927 A1 | 8/2003 | DiPoto et al. |
| 2003/0154986 A1* | 8/2003 | Fariss et al. ............... 128/207.14 |
| 2003/0191476 A1 | 10/2003 | Smit |
| 2003/0199989 A1 | 10/2003 | Stack et al. |
| 2003/0199990 A1 | 10/2003 | Stack et al. |
| 2003/0199991 A1 | 10/2003 | Stack et al. |
| 2003/0208260 A1 | 11/2003 | Lau et al. |
| 2003/0216749 A1 | 11/2003 | Ishikawa et al. |
| 2003/0233140 A1 | 12/2003 | Hartley et al. |
| 2004/0019388 A1 | 1/2004 | Starkebaum |
| 2004/0024386 A1 | 2/2004 | Deem et al. |
| 2004/0037865 A1 | 2/2004 | Miller |
| 2004/0039452 A1 | 2/2004 | Bessler |
| 2004/0044357 A1 | 3/2004 | Gannoe et al. |
| 2004/0082963 A1 | 4/2004 | Gannoe et al. |
| 2004/0092892 A1 | 5/2004 | Kagan et al. |
| 2004/0092974 A1 | 5/2004 | Gannoe et al. |
| 2004/0093063 A1 | 5/2004 | Wright et al. |
| 2004/0093065 A1 | 5/2004 | Yachia et al. |
| 2004/0098079 A1 | 5/2004 | Hartley et al. |
| 2004/0107004 A1 | 6/2004 | Levine et al. |
| 2004/0117031 A1 | 6/2004 | Stack et al. |
| 2004/0122410 A1 | 6/2004 | Deem et al. |
| 2004/0122452 A1 | 6/2004 | Deem et al. |
| 2004/0122453 A1 | 6/2004 | Deem et al. |
| 2004/0122470 A1 | 6/2004 | Deem et al. |
| 2004/0133147 A1 | 7/2004 | Woo |
| 2004/0136971 A1 | 7/2004 | Scharp et al. |
| 2004/0138525 A1 | 7/2004 | Saadat et al. |
| 2004/0138529 A1 | 7/2004 | Wiltshire et al. |
| 2004/0138760 A1 | 7/2004 | Schurr |
| 2004/0138761 A1 | 7/2004 | Stack et al. |
| 2004/0143342 A1 | 7/2004 | Stack et al. |
| 2004/0148034 A1 | 7/2004 | Kagan et al. |
| 2004/0151740 A1 | 8/2004 | Aoki et al. |
| 2004/0153167 A1 | 8/2004 | Stack et al. |
| 2004/0158229 A1 | 8/2004 | Quinn |
| 2004/0158331 A1 | 8/2004 | Stack et al. |
| 2004/0172063 A1 | 9/2004 | Li et al. |
| 2004/0172141 A1 | 9/2004 | Stack et al. |
| 2004/0172142 A1 | 9/2004 | Stack et al. |
| 2004/0172143 A1 | 9/2004 | Geitz |
| 2004/0181242 A1 | 9/2004 | Stack et al. |
| 2004/0193093 A1 | 9/2004 | Desmond, III |
| 2004/0193261 A1 | 9/2004 | Berreklouw |
| 2004/0210243 A1 | 10/2004 | Gannoe et al. |
| 2004/0220682 A1 | 11/2004 | Levine et al. |
| 2004/0236363 A1 | 11/2004 | Kieturakis et al. |
| 2004/0236401 A1 | 11/2004 | Shin et al. |
| 2004/0249362 A1 | 12/2004 | Levine et al. |
| 2005/0004681 A1 | 1/2005 | Stack et al. |
| 2005/0033331 A1 | 2/2005 | Burnett et al. |
| 2005/0043601 A1 | 2/2005 | Kilcoyne et al. |
| 2005/0043817 A1 | 2/2005 | McKenna et al. |
| 2005/0049718 A1 | 3/2005 | Dann et al. |
| 2005/0055039 A1 | 3/2005 | Burnett et al. |
| 2005/0060017 A1 | 3/2005 | Fischell et al. |
| 2005/0075622 A1 | 4/2005 | Levine et al. |
| 2005/0080395 A1 | 4/2005 | Levine et al. |
| 2005/0080431 A1 | 4/2005 | Levine et al. |
| 2005/0080480 A1 | 4/2005 | Bolea et al. |
| 2005/0080491 A1 | 4/2005 | Levine et al. |
| 2005/0085787 A1 | 4/2005 | Laufer |
| 2005/0085923 A1 | 4/2005 | Levine et al. |
| 2005/0090873 A1 | 4/2005 | Imran |
| 2005/0096725 A1 | 5/2005 | Pomeranz et al. |
| 2005/0096750 A1 | 5/2005 | Kagan et al. |
| 2005/0107862 A1 | 5/2005 | Øhlenschlaeger |
| 2005/0111072 A1 | 5/2005 | Miyagaki et al. |
| 2005/0125020 A1 | 6/2005 | Meade et al. |
| 2005/0125075 A1 | 6/2005 | Meade et al. |
| 2005/0149114 A1 | 7/2005 | Cartledge et al. |
| 2005/0171556 A1 | 8/2005 | Murphy |
| 2005/0182481 A1 | 8/2005 | Schlick et al. |
| 2005/0192614 A1 | 9/2005 | Binmoeller |
| 2005/0216040 A1 | 9/2005 | Gertner et al. |
| 2005/0216042 A1 | 9/2005 | Gertner |
| 2005/0221072 A1 | 10/2005 | Dubrow et al. |
| 2005/0228415 A1 | 10/2005 | Gertner |
| 2005/0228504 A1 | 10/2005 | Demarais |
| 2005/0240279 A1 | 10/2005 | Kagan et al. |
| 2005/0256587 A1 | 11/2005 | Egan |
| 2005/0267405 A1 | 12/2005 | Shah |
| 2005/0267499 A1 | 12/2005 | Stack et al. |
| 2005/0267533 A1 | 12/2005 | Gertner |
| 2006/0009858 A1 | 1/2006 | Levine et al. |
| 2006/0064120 A1 | 3/2006 | Levine et al. |
| 2006/0106332 A1 | 5/2006 | Knudson et al. |
| 2006/0142836 A1 | 6/2006 | Hartley et al. |
| 2006/0155312 A1 | 7/2006 | Levine et al. |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0212042 A1 | 9/2006 | Lamport et al. |
| 2006/0265082 A1 | 11/2006 | Meade et al. |
| 2006/0271175 A1 | 11/2006 | Woolfson et al. |
| 2006/0287734 A1 | 12/2006 | Stack et al. |
| 2007/0005147 A1 | 1/2007 | Levine et al. |
| 2007/0010794 A1 | 1/2007 | Dann et al. |
| 2007/0010864 A1 | 1/2007 | Dann et al. |
| 2007/0026042 A1 | 2/2007 | Narayanan |
| 2007/0027548 A1 | 2/2007 | Levine et al. |
| 2007/0032879 A1 | 2/2007 | Levine et al. |
| 2007/0049801 A1 | 3/2007 | Lamport et al. |
| 2007/0083258 A1 | 4/2007 | Falotico et al. |
| 2007/0083271 A1 | 4/2007 | Levine et al. |
| 2007/0173787 A1 | 7/2007 | Huang et al. |
| 2008/0071383 A1 | 3/2008 | Levine et al. |
| 2008/0097466 A1 | 4/2008 | Levine et al. |
| 2008/0103604 A1 | 5/2008 | Levine et al. |
| 2008/0208357 A1 | 8/2008 | Melanson et al. |
| 2008/0221575 A1 | 9/2008 | Betts |
| 2008/0223476 A1 | 9/2008 | Stinson |
| 2008/0234834 A1 | 9/2008 | Meade et al. |
| 2012/0215152 A1 | 8/2012 | Levine et al. |
| 2013/0012862 A1 | 1/2013 | Meade et al. |
| 2014/0194805 A1 | 7/2014 | Levine et al. |

FOREIGN PATENT DOCUMENTS

| | | |
|---|---|---|
| EP | 0 278 937 B1 | 10/1993 |
| EP | 0 506 918 B1 | 1/1996 |
| EP | 0 754 017 B1 | 1/1997 |
| EP | 0 843 538 B1 | 5/1998 |
| EP | 0 857 471 A2 | 8/1998 |
| EP | 0 935 977 | 8/1999 |
| EP | 1 481 649 A1 | 12/2004 |
| EP | 1 504 778 A2 | 9/2005 |
| EP | 1 772 115 A1 | 4/2007 |
| FR | 2 380 034 | 9/1978 |
| JP | 04212348 | 8/1992 |
| JP | 2000 126304 | 5/2000 |
| WO | WO 92/06734 A1 | 4/1992 |
| WO | WO 95/05132 A | 2/1995 |
| WO | WO 97/03624 A1 | 2/1997 |
| WO | WO 98/08456 | 3/1998 |
| WO | WO 98/22045 A | 5/1998 |
| WO | WO 99/23953 A | 5/1999 |
| WO | WO 99/44536 A | 9/1999 |
| WO | WO 00/12027 | 3/2000 |
| WO | WO 00/32137 | 6/2000 |
| WO | WO 00/042945 | 7/2000 |
| WO | WO 00/42949 | 7/2000 |
| WO | WO 01/12256 A1 | 2/2001 |
| WO | WO 01/35861 A1 | 5/2001 |

(56) References Cited

FOREIGN PATENT DOCUMENTS

| | | |
|---|---|---|
| WO | WO 01/45485 A2 | 6/2001 |
| WO | WO 02/081019 A1 | 10/2002 |
| WO | WO 02/096327 A | 12/2002 |
| WO | WO 02/096327 A2 | 12/2002 |
| WO | WO 03/017882 A2 | 3/2003 |
| WO | WO 03/034976 A1 | 5/2003 |
| WO | WO 03/086246 A1 | 10/2003 |
| WO | WO 03/086247 A1 | 10/2003 |
| WO | WO 03/086360 A1 | 10/2003 |
| WO | WO 03/094785 A1 | 11/2003 |
| WO | WO 2004/000169 A1 | 12/2003 |
| WO | WO 2004/004542 A2 | 1/2004 |
| WO | WO 2004/014237 A1 | 2/2004 |
| WO | WO 2004/019765 A2 | 3/2004 |
| WO | WO 2004/019765 A3 | 3/2004 |
| WO | WO 2004/021894 A1 | 3/2004 |
| WO | WO 2004/037064 A2 | 5/2004 |
| WO | WO 2004/037064 A3 | 5/2004 |
| WO | WO 2004/049982 A2 | 6/2004 |
| WO | WO 2004/064680 A1 | 8/2004 |
| WO | WO 2004/064682 A1 | 8/2004 |
| WO | WO 2004/064685 A1 | 8/2004 |
| WO | WO 2004/069331 A2 | 8/2004 |
| WO | WO 2004/069332 A1 | 8/2004 |
| WO | WO 2004/073782 A1 | 9/2004 |
| WO | WO 2004/080336 A2 | 9/2004 |
| WO | WO 2004/087014 A2 | 10/2004 |
| WO | WO 2004/087233 A2 | 10/2004 |
| WO | WO 2004/093639 A3 | 11/2004 |
| WO | WO 2005/011533 A1 | 2/2005 |
| WO | WO 2005/060869 A1 | 7/2005 |
| WO | WO 2005/060882 A1 | 7/2005 |
| WO | WO 2005/082296 A1 | 9/2005 |
| WO | WO 2005/110280 A2 | 11/2005 |
| WO | WO 2005/110280 A3 | 11/2005 |
| WO | WO 2005/117716 A2 | 12/2005 |
| WO | WO 2005/118049 A1 | 12/2005 |
| WO | WO 2005/120363 A1 | 12/2005 |
| WO | WO 2006/016894 A1 | 2/2006 |
| WO | WO 2006/034062 A1 | 3/2006 |
| WO | WO 2006/078781 A1 | 7/2006 |
| WO | WO 2006/078927 A1 | 7/2006 |
| WO | WO 2006/088578 A1 | 8/2006 |
| WO | WO 2006/102012 A1 | 9/2006 |
| WO | WO 2006/133311 A2 | 12/2006 |

OTHER PUBLICATIONS

Binkert, C. A., et al., "Benign and Malignant Stenoses of the Stomach and Duodenum: Treatment with Self-expanding Metallic Endoprostheses," *Radiology* 199(2):335-338 (1996).

Choostent™, Covered Esophageal Stent, Instructions, Retrieved from the Internet (http://mitech.co.kr/uploads/images/282/use guide esophachoo_english.pdf) on Jul. 26, 2005.

Cwikiel, W., et al., "Self-expanding Stent in the Treatment of Benign Esophageal Strictures: Experimental Study in Pigs and Presentation of Clinical Cases," *Radiology* 187(3):667-671 (1993).

Dolan, K. et al., "Treating Diabetes in the Morbidly Obese by Laproscopic Gastric Band," *Obesity Surgery*, vol. 13, pp. 439-443 (2003).

Dormann, A.J. et al., "Self-expanding metallic stents for continous dilatation of benign stenosis in gastrointestinal tract—first results of long-term follow-up in interim stent application in pyloric and colonic obstructions," *Z Gastroenteral* 39:957-960 (2001).

Feretis, C., et al., "Palliation of Malignant Gastric Outlet Obstruction with Self-Expanding Metal Stents," *Endoscopy* 28:225-228 (1996).

Hwang, J.C., et al., "Covered Retrievable Tracheobronichial Hinged Stent: An Experimental Study in Dogs," *J. Vasc. Interv. Radiol.*, 12(12):1429-1436 (Dec. 2001).

International Search Report from related application PCT/US2008/013540 mailed on Mar. 26, 2009.

Irie, T., et al., "Relocatable Gianturco Expandable Metallic Stents," *Radiology*, 178:575-578 (1991).

Lee, B.H., et al., "New Self-Expandable Spiral Metallic Stent: Preliminary clinical Evaluation in Malignant Biliary Obstruction," *J. Vasc Interv Radiol.*, 6(4):635-640 (Jul. 8, 1995).

Lee, S.H., "The Role of Oesophageal Stenting in the Non-Surgical Management of Oesophageal Strictures," *British J. Radiology*, 74:891-900 (Oct. 2001).

Park, B.P. et al., Malignant Obstruction of Gastric Outlet and Duodenum: Palliation with Flexible Covered Metallic Stents, *Radiology* 219(3):679-683 (2001).

Pories, W.J., "Why Does the Gastric Bypass Control Type 2 Diabetes Mellitus?" *Obesity Surgery*, 2:303-313 (1992).

Pories, W.J., et al., "Etiology of Type II Diabetes Mellitus: Role of the Foregut," *World J. Surg.*, 25:527-531 (2001).

Rubino, F. and J. Marescaux, "Effect of Duodenal-Jejunal Exclusion in a Non-obese Animal Model of Type 2 Diabetes, A New Perspective for an Old Disease," *Annals of Surgery* 239(1):1-11, Jan. 2004.

Rubino, F., et al., "Potential of Surgery for Curing Type 2 Diabetes Mellitus," *Annals of Surgery* 236(5): 554-559 (2002).

Sandha, G. S. and Marcon, N. E., "Expandable Metal Stents for Benign Esophageal Obstruction," *Gastrointestinal Endoscopy Clinics of North America* 9:(3)437-446 (1999).

Shim, C.S., et al., "Fixation of a Modified Covered Esophageal Stent: Its Clinical Usefulness for Preventing Stent Migration," *Endoscopy*, 33(10):843-848 (Oct. 2001).

Song, H.Y., et al., "Benign and Malignant Esophageal Strictures: Treatment with a Polyurethane-Covered Retrievable Expandable Metallic Stent," *Radiology*, 203(3):747-752 (Jun. 1997).

Song, H.Y., et al., "Covered Retrievable Expandable Nitinol Stents in Patients with Benign Esophageal Strictures: Initial Experience," *Radiology*, 217:551-557 (Nov. 2000).

Song, H.Y., et al., "Tracheobronchial Strictures: Treatment with a Polyurethane-Covered Retrievable Expandable Nitinol Stent—Initial Experience," *Radiology*, 213:905-912 (Dec. 1999).

Written Opinion of the International Searching Authority from related application PCT/US2008/013540 mailed on Mar. 26, 2009.

Yates III, M. R., et al., "Palliation of Malignant Gastric and Small Intestinal Strictures With Self-Expandable Metal Stents," *Endoscopy* 30:266-272 (1998).

Yoon, C.J., et al., "Removal of Retrievable Esophageal and Gastrointestinal Stents: Experience in 113 Patients," *American J. of Roentgenology*, 183:1437-1444 (Nov. 2004).

US Office Action, dated Oct. 1, 2012, for U.S. Appl. No. 13/170,785, "Intestinal Sleeve," consisting of 9 pages.

US Office Action, dated Mar. 4, 2013, for U.S. Appl. No. 13/618,036, "Methods and Apparatus for Anchoring Within the Gastrointestinal Tract.".

Office Action dated Mar. 20, 2013 for U.S. Appl. No. 13/170,785, "Intestinal Sleeve.".

Office Action dated Jun. 7, 2013 for U.S. Appl. No. 13/618,036, "Methods and Apparatus for Anchoring Within the Gastrointestinal Tract.".

Notice of Allowance dated Jun. 14, 2013 for U.S. Appl. No. 11/635,890, "Anti-Obesity Devices.".

U.S. Office Action, dated Jan. 8, 2014, for U.S. Appl. No. 13/401,258 "Anti-Obesity Devices," consisting of 6 pages.

International Search Report and Written Opinion of the International Searching Authority from PCT/US2014/010298 entitled "Jejunal Feeding Tube and Delivery System", mailed May 27, 2014.

Final Office Action dated Aug. 6, 2014 for U.S. Appl. No. 13/401,258 "Bariatric Sleeve.".

\* cited by examiner

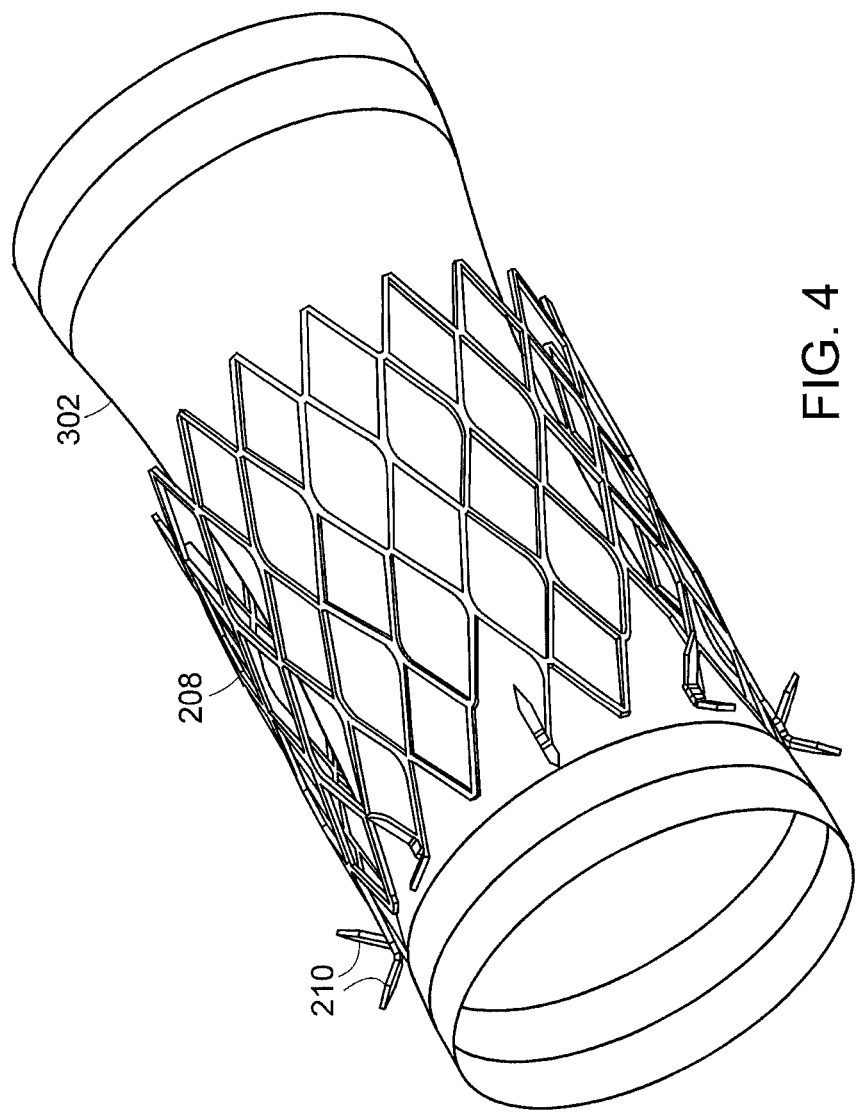

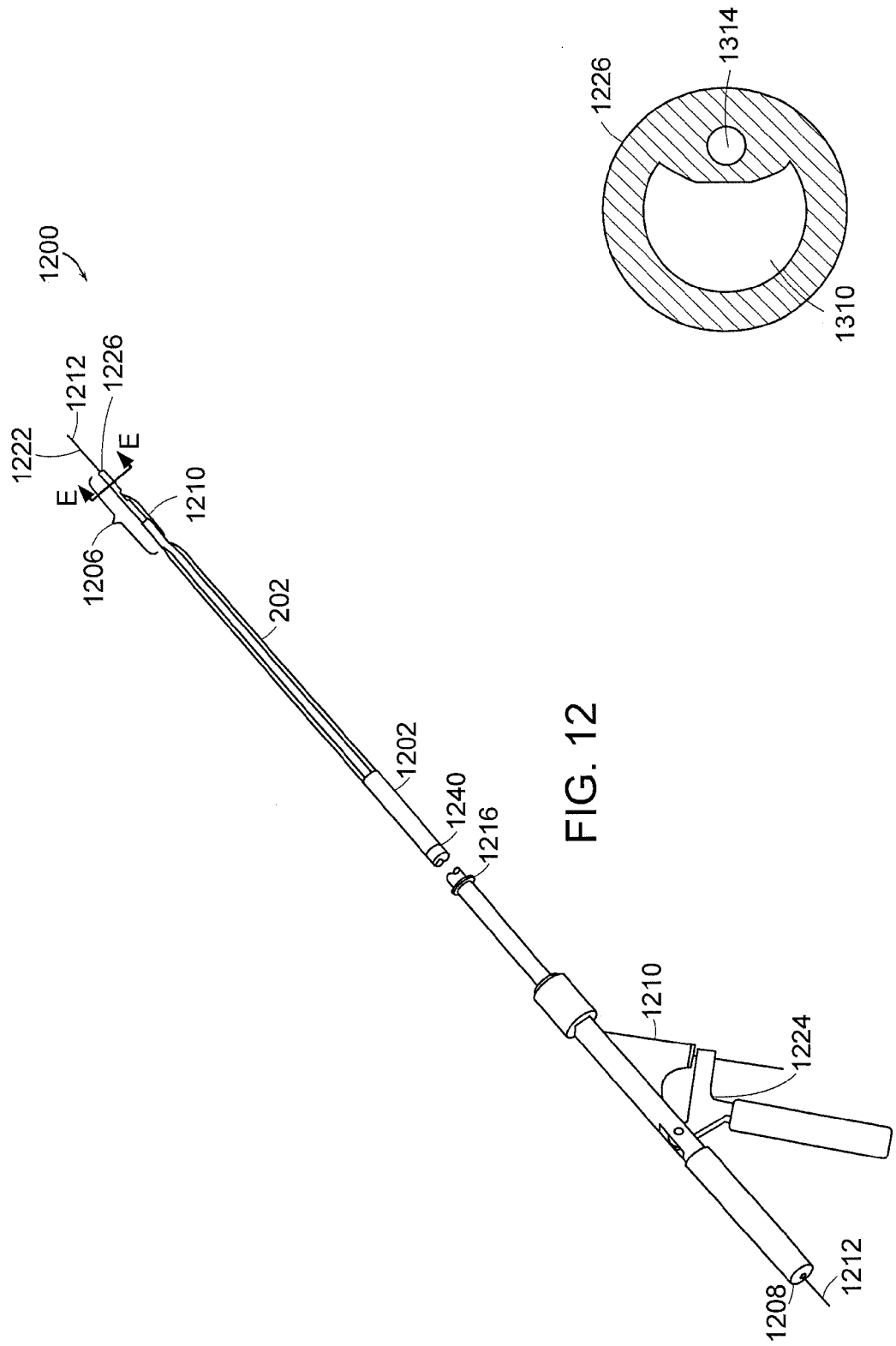

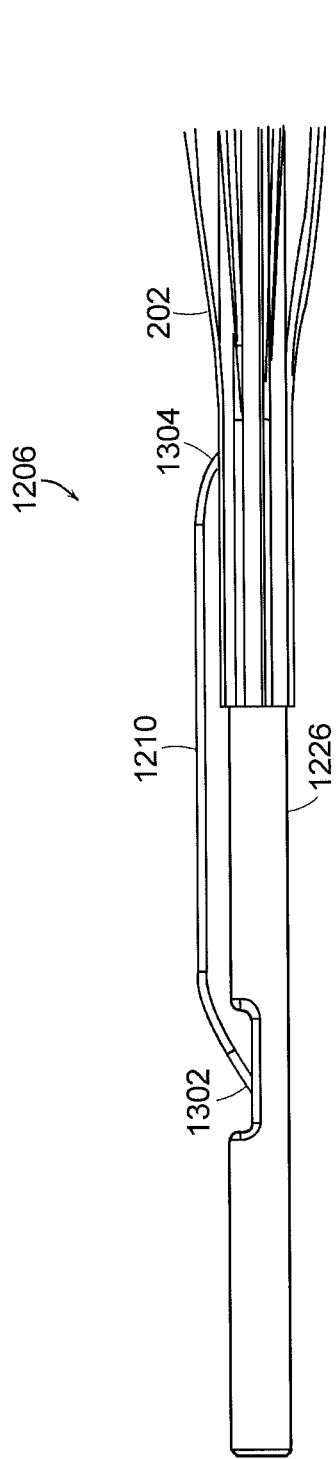
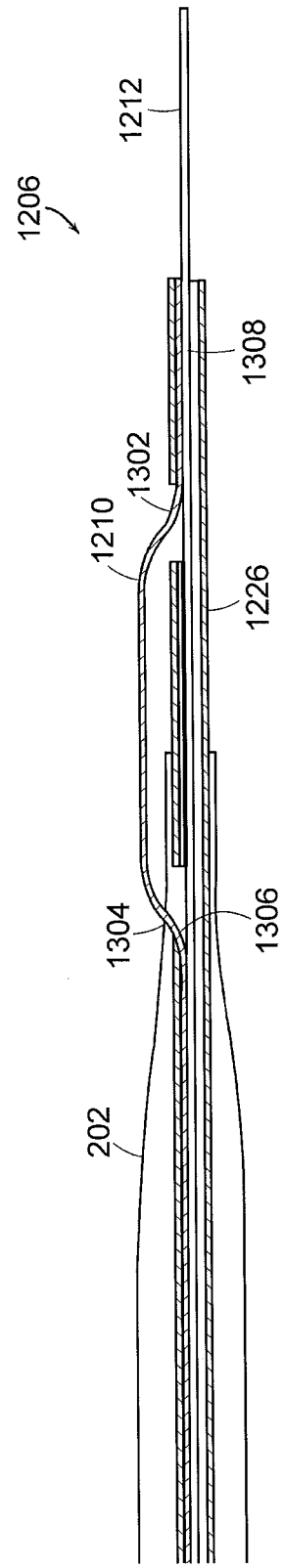
FIG. 14A
FIG. 14B

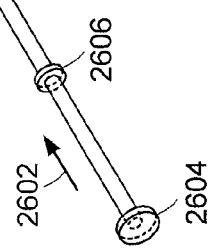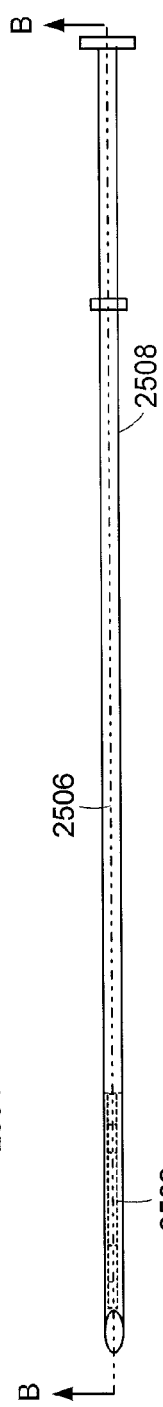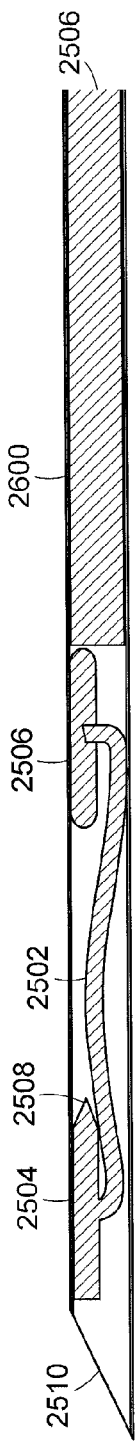

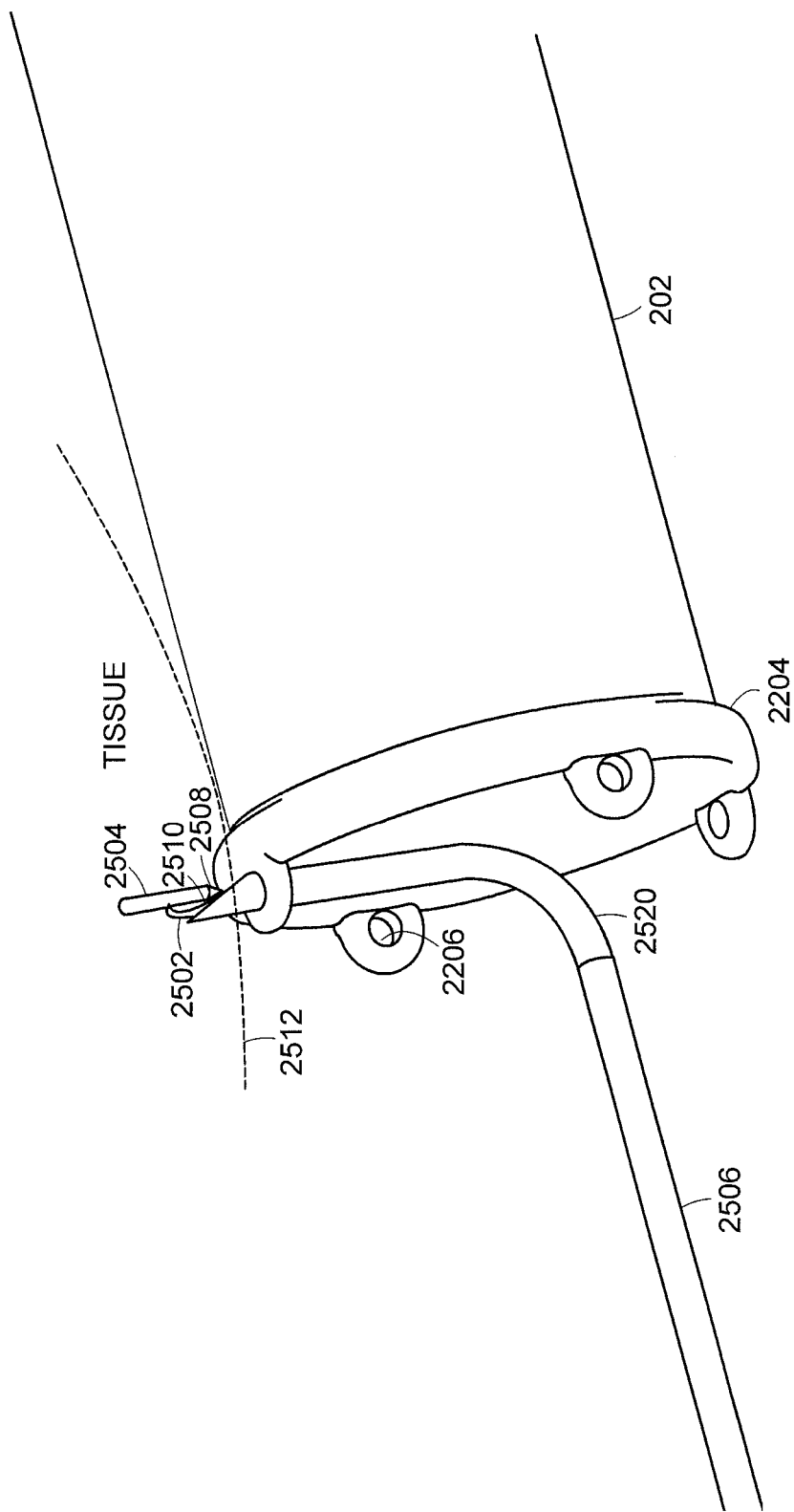

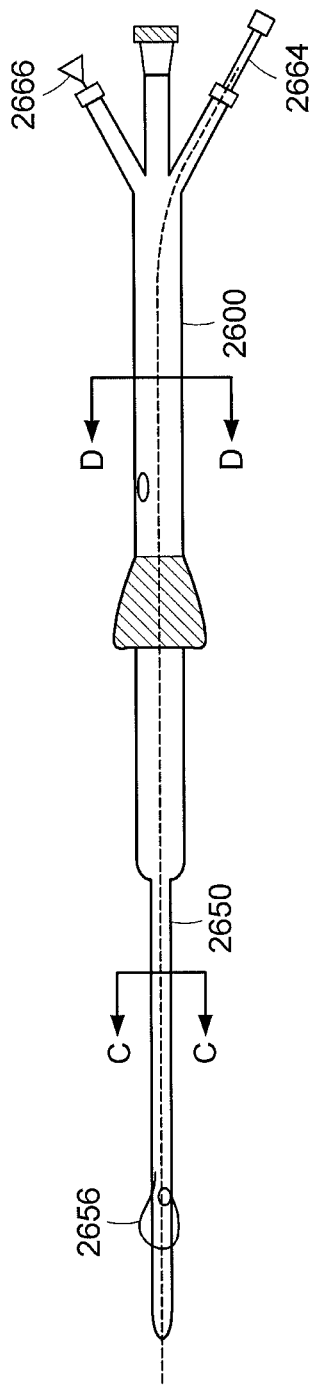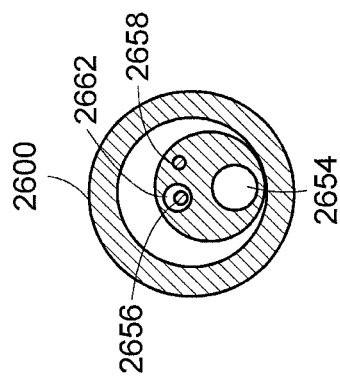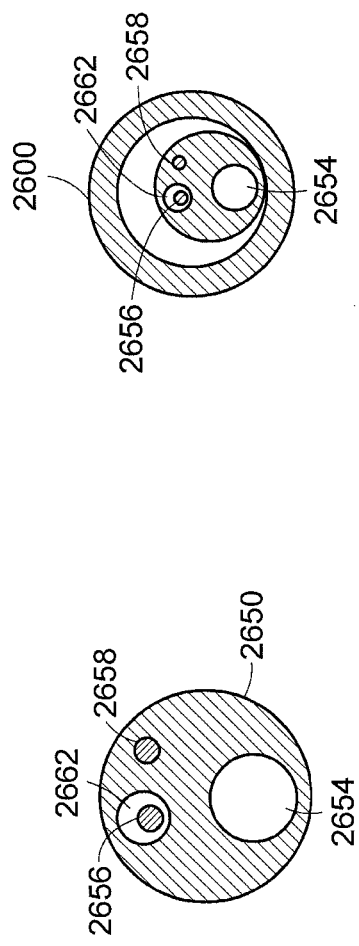
FIG. 26A
FIG. 26B
FIG. 26C

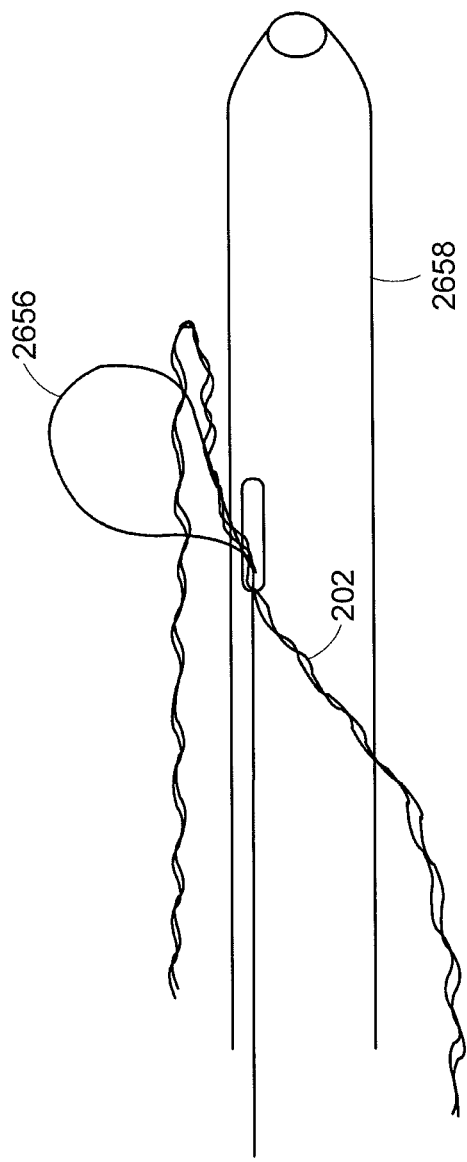
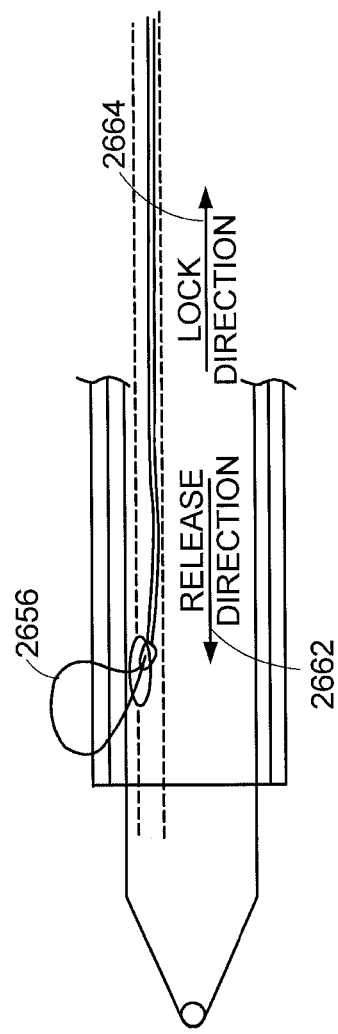

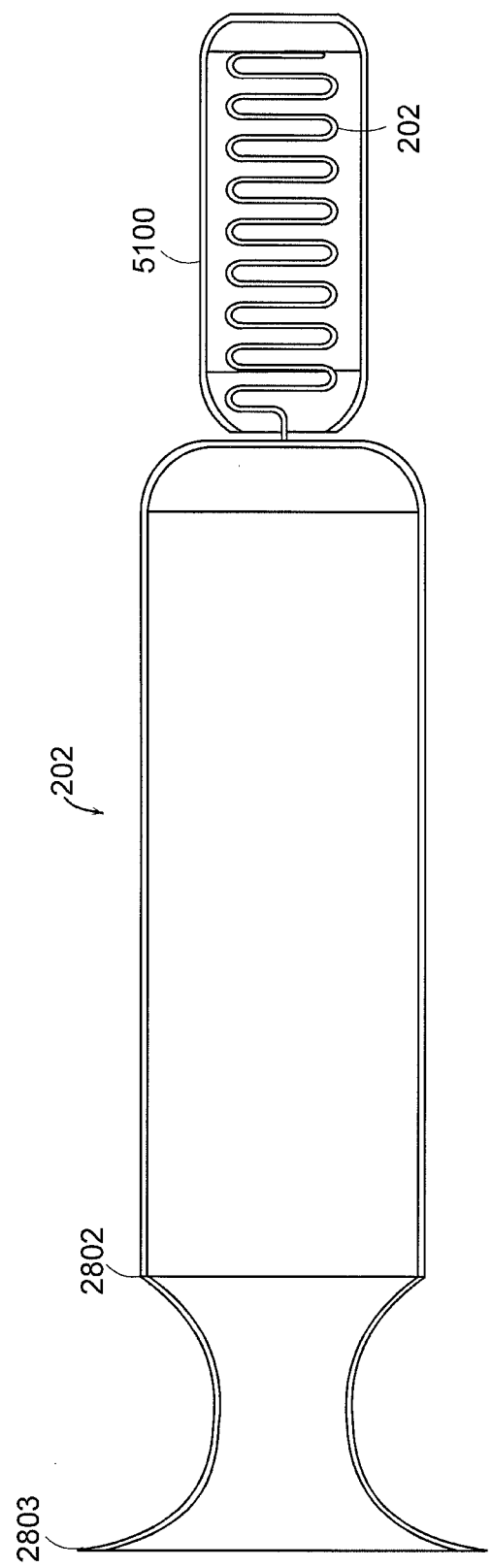

ANTI-OBESITY DEVICES

This application is a continuation of U.S. application Ser. No. 11/635,890, filed Dec. 8, 2006, now U.S. Pat. No. 8,486,153 which is a divisional of U.S. application Ser. No. 11/541,616, filed Oct. 2, 2006, now U.S. Pat. No. 7,766,861, which is a divisional of U.S. application Ser. No. 10/726,011, filed on Dec. 2, 2003, now U.S. Pat. No. 7,122,058, which claims the benefit of U.S. Provisional Application No. 60/512,145, filed on Oct. 17, 2003.

The entire teachings of the above applications are incorporated herein by reference.

BACKGROUND OF THE INVENTION

According to the Center for Disease Control (CDC), over sixty percent of the United States population is overweight, and almost twenty percent are obese. This translates into 38.8 million adults in the United States with a Body Mass Index (BMI) of 30 or above. The BMI is defined as a person's weight (in kilograms) divided by height (in meters), squared. To be considered clinically, morbidly obese, one must meet one of three criteria: BMI over 35, 100 lbs. overweight or 100% above ideal body weight. There is also a category for the super-obese for those weighing over 350 lbs.

Obesity is an overwhelming health problem. Because of the enormous strain associated with carrying this excess weight, organs are affected, as are the nervous and circulatory systems. In 2000, the National Institute of Diabetes, Digestive and Kidney Diseases (NIDDK) estimated that there were 280,000 deaths directly related to obesity. The NIDDK further estimated that the direct cost of healthcare in the US associated with obesity is $51 billion. In addition, Americans spend $33 billion per year on weight loss products. In spite of this economic cost and consumer commitment, the prevalence of obesity continues to rise at alarming rates. From 1991 to 2000, obesity in the US grew by 61%. Not exclusively a US problem, worldwide obesity ranges are also increasing dramatically.

One of the principle costs to the healthcare system stems from the co-morbidities associated with obesity. Type-2 diabetes has climbed to 7.3% of the population. Of those persons with Type-2 diabetes, almost half are clinically obese, and two thirds are approaching obese. Other co-morbidities include hypertension, coronary artery disease, hypercholesteremia, sleep apnea and pulmonary hypertension.

Although the physiology and psychology of obesity are complex, the medical consensus is that the cause is quite simple—an over intake of calories combined with a reduction in energy expenditures seen in modern society. While the treatment seems quite intuitive, the institution of a cure is a complex issue that has so far vexed the best efforts of medical science. Dieting is not an adequate long-term solution for most people. Once an individual has slipped past the BMI of 30, significant changes in lifestyle are the only solution.

There have been many attempts in the past to surgically modify patients' anatomies to attack the consumption problem by reducing the desire to eat. Stomach saplings, or gastroplasties, to reduce the volumetric size of the stomach, therein achieving faster satiety, were performed in the 1980's and early 1990's. Although able to achieve early weight loss, sustained reduction was not obtained. The reasons are not all known, but are believed related to several factors. One of which is that the stomach stretches over time increasing volume while psychological drivers motivate patients to find creative approaches to literally eat around the smaller pouch.

There are currently two surgical procedures that successfully produce long-term weight loss; the Roux-en-Y gastric bypass and the biliopancreatic diversion with duodenal switch (BPD). Both procedures reduce the size of the stomach plus shorten the effective-length of intestine available for nutrient absorption. Reduction of the stomach size reduces stomach capacity and the ability of the patient to take in food. Bypassing the duodenum makes it more difficult to digest fats, high sugar and carbohydrate rich foods. One objective of the surgery is to provide feedback to the patient by producing a dumping syndrome if they do eat these food products. Dumping occurs when carbohydrates directly enter the jejunum without being first conditioned in the duodenum. The result is that a large quantity of fluid is discharged into the food from the intestinal lining. The total effect makes the patient feel light-headed and results in severe diarrhea. For reasons that have not been determined the procedure also has an immediate therapeutic effect on diabetes.

Although the physiology seems simple, the exact mechanism of action in these procedures is not understood. Current theory is that negative feedback is provided from both regurgitation into the esophagus and dumping when large volumes of the wrong foods are eaten. Eventually, patients learn that to avoid both these issues they must be compliant with the dietary restrictions imposed by their modified anatomy. In the BPD procedure, large lengths of jejunum are bypassed resulting in malabsorption and therefore, reduced caloric uptake. In fact, the stomach is not reduced in size as much in the BPD procedure so that the patient is able to consume sufficient quantities of food to compensate for the reduced absorption. This procedure is reserved for the most morbidly obese as there are several serious side effects of prolonged malabsorption.

Unfortunately, these procedures carry a heavy toll. The morbidity rate for surgical procedures is alarmingly high with 11% requiring surgical intervention for correction. Early small bowel obstruction occurs at a rate of between 2-6% in these surgeries and mortality rates are reported to be approximately 0.5-1.5%. While surgery seems to be an effective answer, the current invasive procedures are not acceptable with these complication rates. Laparoscopic techniques applied to these surgeries provide fewer surgical complications but continue to expose these very ill patients to high operative risk in addition to requiring an enormous level of skill by the surgeon. Devices to reduce absorption in the small intestines have been proposed (See U.S. Pat. No. 5,820,584 (Crabb), U.S. Pat. No. 5,306,300 (Berry) and U.S. Pat. No. 4,315,509 (Smit)). However, these devices have not been successfully implemented.

SUMMARY OF THE INVENTION

The present invention provides a method and apparatus for the application of a barrier sleeve in the digestive tract to limit absorption of food products in specific parts of the digestive tract and to provide negative feedback to patients with morbid obesity enabling them to modify their heating habits.

A gastrointestinal implant device can be inserted endoscopically in combination with a delivery catheter. The delivery catheter includes a catheter for passage through the intestines and a spherically shaped element coupled to the distal end of the catheter. The spherically shaped element may be remotely releasable.

A delivery system for placing a gastrointestinal implant device in a body includes an outer sheath in the proximal portion of the delivery system for storing a proximal portion of the gastrointestinal implant device. The proximal portion of the gastrointestinal implant device includes an anchoring device for anchoring the device in the stomach. The delivery system includes an inner sheath within the outer sheath. The inner sheath extends beyond the outer sheath toward the distal end of the delivery system. A first lumen is within the inner sheath for passing the outer sheath over a guidewire and a second lumen is within the inner sheath for moving a moveable element to secure the distal end of a sleeve coupled to the stent to the inner sheath. The delivery system also includes a release mechanism to release the anchoring device from the outer sheath. A sleeve release mechanism is coupled to the moveable element for releasing the distal end of the sleeve. There is a spherical shaped element at the distal end of the delivery system which is held by the moveable element.

The moveable element may be a sleeve retention wire, which exits the second lumen and pierces the distal end of the sleeve. The sleeve release mechanism pulls the outer sheath toward the proximal end of the delivery system to remove the outer sheath from the anchoring device. The sleeve release mechanism pulls the moveable element toward the proximal end of the delivery system to release the distal end of the sleeve after the anchoring device has been released.

A distal portion of the sleeve may be stored in a pill for delivery and the distal portion of the sleeve is released from the pill by peristalsis. The distal portion of the sleeve may be stored in a dissolvable pill for delivery. The spherical shaped element is attached to an element retention wire which is held by the moveable element. The moveable element may be looped through the spherical shaped element, the distal end of the moveable element may be coiled and stored within the spherical shaped element or the moveable element may be held in an S-shaped track within the spherical shaped element.

The spherical shaped element at the distal end of the delivery system may be an expandable balloon. The element may be remotely releasable. The inner sheath may include a third lumen through which a fluid is passed to release the sleeve from the distal end of the delivery device. The sleeve release mechanism pulls the moveable element toward the proximal end of the delivery system to release the spherical shaped element after the anchoring device has been released.

A gastrointestinal implant device includes a flexible sleeve and a collapsible anchor coupled to a proximal end of the sleeve. The flexible sleeve is open at both ends, and adapted to extend into the duodenum to limit absorption of nutrients in the duodenum. The anchor includes two spaced apart rings of differing diameters to anchor the proximal portion of the sleeve in the stomach. The rings may be made from Nitinol and may include at least two stabilizing ears and may be formed by loosely intertwined wires. The rings may be linked with a connecting bar. The connecting bar includes extensions extending from the exterior surface of the bar for anchoring the proximal portion of the sleeve in the stomach. Extensions extending from the exterior surface of a proximal ring and extensions extending from the exterior surface of a distal ring are angled towards each other. The anchor is covered by a proximal portion of the sleeve. The interior surface of the ring is covered by the sleeve and the exterior surface of the ring is coated with polyurethane. The rings are folded in a u-shape stored in a delivery tube to insert the flexible sleeve.

The sleeve may be impregnated with an anti-hunger hormone such as peptide-YY. The sleeve may be impregnated with a drug that reduces inflammation. The distance between the rings may be selected to hold the pylorus open. The sleeve may be formed of low friction materials such as cast polytetrafluoroethylene, polytetrafluoroethylene, cast fluorinated ethylene propylene with polytetrafluoroethylene coating, extruded fluoronated ethylene propylene and extruded perfluoroalkoxy.

The gastrointestinal implant device can be used as a method for treating intestinal bowel disease. A flexible sleeve is anchored within the stomach. The sleeve is open at both ends and impregnated with a drug that reduces inflammation. The flexible sleeve is into the jejunum.

The gastrointestinal implant device can be used as a method for treating obesity. A flexible sleeve is anchored within the stomach. The sleeve is open at both ends and enhanced with anti-hunger hormones and the flexible sleeve is extended into the duodenum.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 4 is a perspective view of the gastrointestinal implant device with the second outer layer of the sleeve removed;

FIG. 12 is a perspective view of a catheter system for delivery of the gastrointestinal implant device;

FIG. 13 is a cross-sectional view of the inner shaft taken along line E-E of FIG. 12;

FIG. 14A is an expanded perspective view of the dead-bolt mechanism shown in FIG. 12;

FIG. 14B is a sectional view of the dead-bolt mechanism shown in FIG. 13A illustrating the sleeve retention wire threaded through the sleeve;

FIG. 25A is a perspective view of a delivery system for delivering the anchor after the gastrointestinal implant device has been placed in the stomach;

FIG. 25B is a plan view of the delivery system shown in FIG. 25A;

FIG. 25C is a cross-sectional view of the distal end of the catheter as taken along line B-B of FIG. 25A;

FIG. 25D is a perspective view of the gastrointestinal implant device illustrating the anchor engaged with the tissue;

FIG. 26A is a plan view of the delivery system including a snare wire for holding the distal end of the sleeve in position;

FIG. 26B is a cross-sectional view taken along line CC of FIG. 26A through the inner sheath;

FIG. 26C is a cross-sectional view taken along line DD of FIG. 26A through the outer sheath showing the inner sheath within the outer sheath;

FIG. 26D is a cross-sectional view through the distal portion of the catheter showing the snare capturing the distal end of the sleeve;

FIG. 26E is a sectional view through the distal portion of the catheter showing the snare locking mechanism;

FIG. 51 is a plan view of an alternative delivery system for delivering a gastrointestinal implant device;

DETAILED DESCRIPTION OF THE INVENTION

Figure 1:
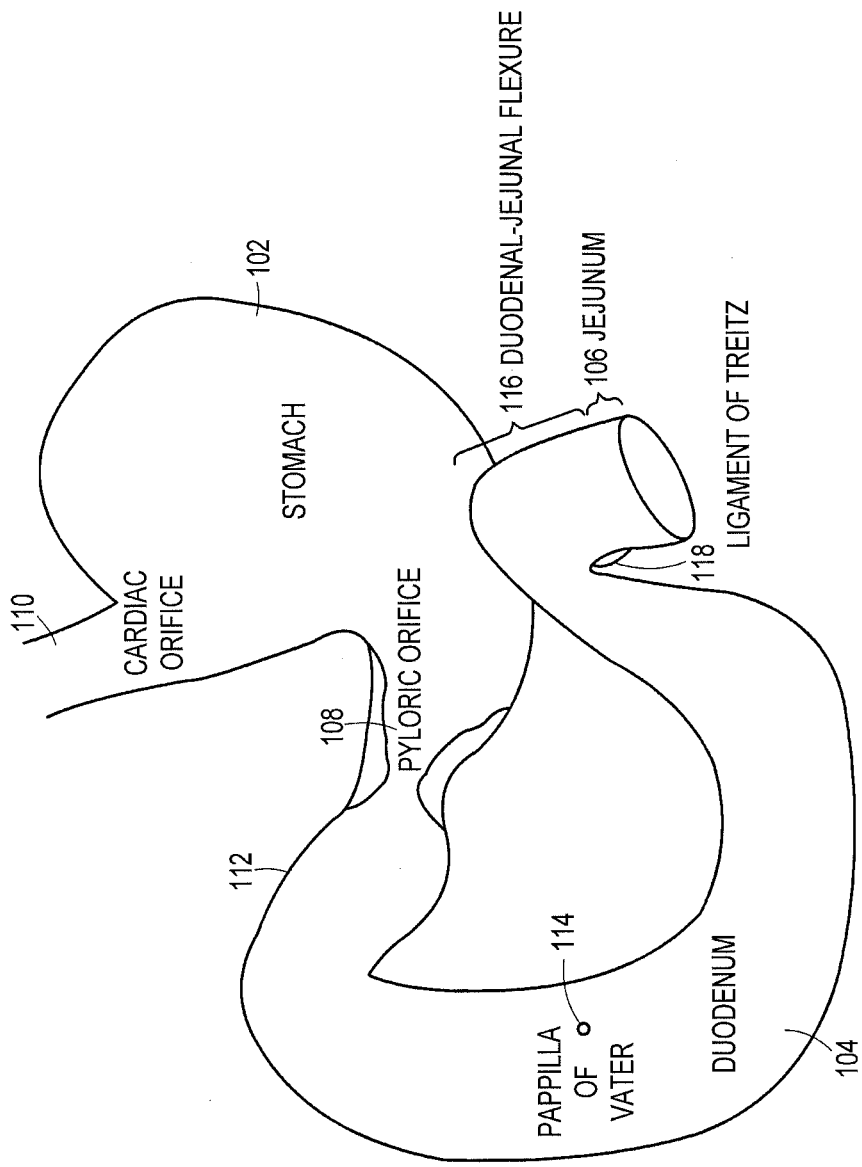
FIG. 1 is a sectional view of a portion of the digestive tract in a body.

A description of preferred embodiments of the invention follows. FIG. 1 is a sectional view of a portion of the digestive tract in a body. Food to be digested enters the stomach 102 through the cardiac orifice 110 from the esophagus. Chyme, a semi-fluid, homogeneous creamy or gruel-like material produced by gastric digestion in the stomach exits the stomach through the pyloric orifice (pylorus) 108 and enters the small intestine 112. The pylorus 108 is a distal aperture of the stomach 102 surrounded by a strong band of circular muscle. The small intestine, about nine feet in length, is a convoluted tube, extending from the pylorus to the ileo-caecal valve where it terminates in the large intestine. The small intestine has three sections, the duodenum 104, jejunum 106 and the ileum (not shown). The first eight to ten inch section of the small intestine, the duodenum, is the shortest, widest and most fixed part of the small intestine.

The duodenum has four sections: superior, descending, transverse and ascending which typically form a U-shape. The superior section is about two inches long and ends at the neck of the gall bladder. The descending section is about three to four inches long and includes a nipple shaped structure (papilla of vater) 114 through which pancreatic juice from the pancreas and bile produced by the liver and stored by the gall bladder enter the duodenum from the pancreatic duct. The pancreatic juice contains enzymes essential to protein digestion and bile dissolves the products of fat digestion. The ascending section is about two inches long and forms the duodenal-jejunal flexure 116 where it joins the jejunum 106, the next section of the small intestine. The duodenal-jejunal flexure 116 is fixed to the ligament of Treitz 118 (musculus supensionus duodeni). The juices secreted in the duodenum break the partially digested food down into particles small enough to be absorbed by the body. The digestive system is described in Gray's Anatomy ("Anatomy of the Human Body", by Henry Gray) and "Human Physiology", Vander, $3^{rd}$ ed, McGraw Hill, 1980, the contents of which are incorporated herein by reference in their entirety.

Figure 2:
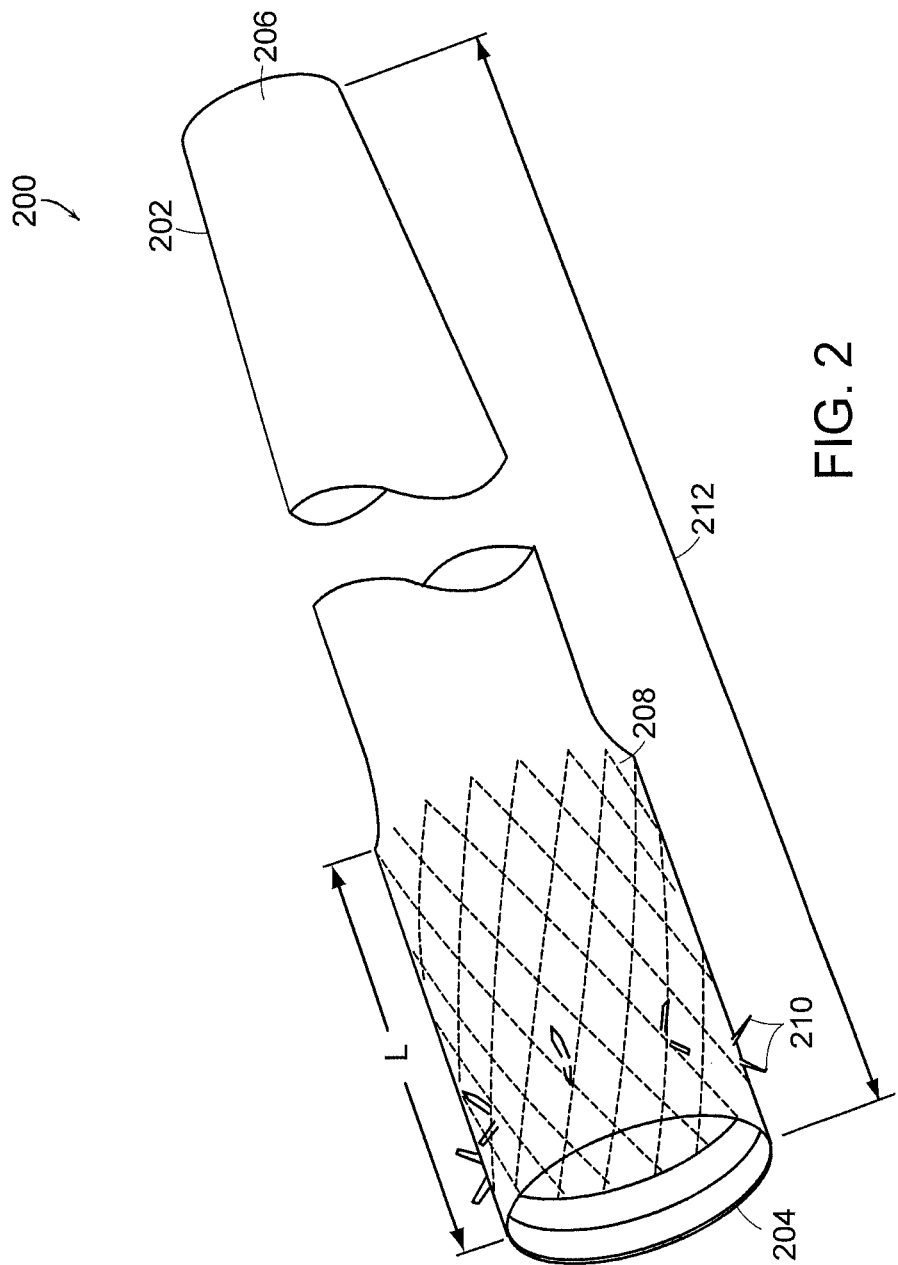
FIG. 2 is a perspective view of a gastrointestinal implant device according to the principles of the present invention.

FIG. 2 is a perspective view of a gastrointestinal implant device 200 according to the principles of the present invention. The gastrointestinal implant device 200 includes an elongated open-ended flexible sleeve or tube 202 having a first proximal opening 204 and a second distal opening 206. Within the sleeve 202 is a passageway that extends from the first proximal opening 204 to the second distal opening 206 for transporting the chyme exiting the stomach 102 (FIG. 1). The surface of the passageway (the interior surface of the implant device 200) is smooth to enable the chyme to easily pass through. The exterior surface of the implant device 200 is smooth to prevent tissue in-growth and to be non-irritating to the bowel.

Within the implant device 200 at the proximal end including the first proximal opening 204 is a collapsible self-expanding stent 208. The stent 208 includes a plurality of opposed barbs 210 for anchoring the implant device 200 to the muscular pylorus in the stomach 102. The diameter of the stent 208 is dependent on the diameter of the pyloric orifice 108 (FIG. 1) about 0.8" to 1.1" based on human anatomy variations. In one embodiment, the length l of the stent 208 is selected to extend through the pylorus 108 and keep the pylorus 108 permanently open to induce "dumping syndrome". In an alternate embodiment, a stent with a shorter length l allows the pylorus 108 to open and close normally.

The sleeve material is thin and conformable so that it collapses in the intestine to a small volume to minimize bowel irritability. It has a low coefficient of friction (<0.20) so that chyme slides easily through it and the bowel slides easily around it. It is of low permeability to fluids so that the chyme does not touch the bowel wall and the digestive enzymes do not significantly breakdown the chyme. It is biologically inert and non-irritating to the tissues. One such material is expanded polytetrafluoroethylene (ePTFE) with a wall thickness of about 0.006" and an internodal distance of 20 microns. This material is hydrophobic but is slightly porous. However, these very small pores may plug over time. The porosity may be reduced by coating the material on the inside, outside or in the pores with dilute solutions of silicone or polyurethane. Another material is polyethylene with a wall thickness of less than 0.001". Other materials include Cast PTFE (polytetrafluoroethylene, Teflon), Cast PTFE with FEP (fluoronated ethylene propylene) or PFA (Perfluoroalkoxy) coating to minimize pin holes, Extruded FEP and Extruded PFA. These materials are solid and non-porous in contrast to ePTFE which is porus, but these materials are also considered to be Teflons. Rubber-like materials typically have friction coefficients of 1-4, significantly stickier than these materials. However, in alternate embodiments other materials having similar characteristics can be used.

The sleeve 202 includes two layers of material at least at the proximal end. A first outer layer covers the exterior of the stent. The second inner layer covers the interior surface of the stent 208. The barbs 210 protrude from the exterior surface of the stent 208 through the first outer layer of the sleeve 208. The holes in the first outer layer through which the barbs 210 protrude are filled with an impervious material such as silicone or urethane to limit mixing of digestive juices with the chyme flowing through the passageway. The diameter of the sleeve 208 is selected such that the first outer layer of the sleeve 208 fits over the stent 208.

The sleeve length 212 ranges from about one foot to about five feet. The typical length of the sleeve 208 is about 1.5 feet from the anchor (barbs 210) in the pyloric region of the stomach to below the ligament of Treitz 118 (FIG. 1). The length 212 of the sleeve 202 is selected to bypass the duodenum 104 (FIG. 1) and a portion of the jejunum. The length is increased to further decrease absorption by bypassing a longer section of the jejunum 106 (FIG. 1). The length 212 of the sleeve 202 is variable and dependent on the patient's Body Mass Index (BMI). The procedure is a less invasive alternative to surgery for the treatment of obesity and morbid obesity and also provides a new treatment approach for type 2 diabetes.

The covered stent 208 can be collapsed into a sheath having a diameter less than ¼ inch to enable endoscopic delivery. Covering the exterior surface of the stent 208 with the first outer layer of the sleeve 202 permits endoscopic removal of the implant device 200 by preventing tissue in-growth on the exterior surface of the stent 208.

Markings can be added to the exterior surface of the sleeve 202 to detect the position and orientation of the sleeve on a fluoroscopic image and whether the sleeve is twisted. For example, a stripe can be painted down the length of the device 200 using tantulum impregnated ink, or tantulum bands can be bonded to the exterior surface of the device. If the sleeve 202 is twisted, the sleeve 202 can be untwisted by inserting a balloon into the proximal end of the device thereby sealing it, and then injecting water into the sleeve at low pressure.

Figure 3A:
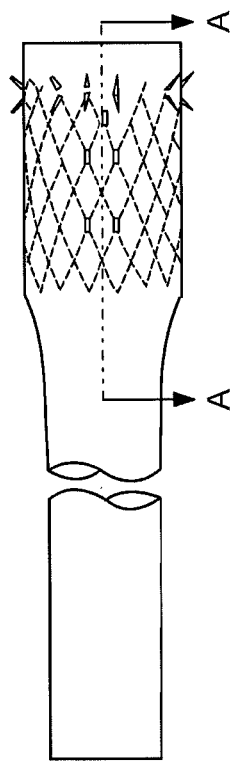
FIG. 3A is a plan view of the proximal portion of the gastrointestinal implant device shown in FIG. 2.
Figure 3B:
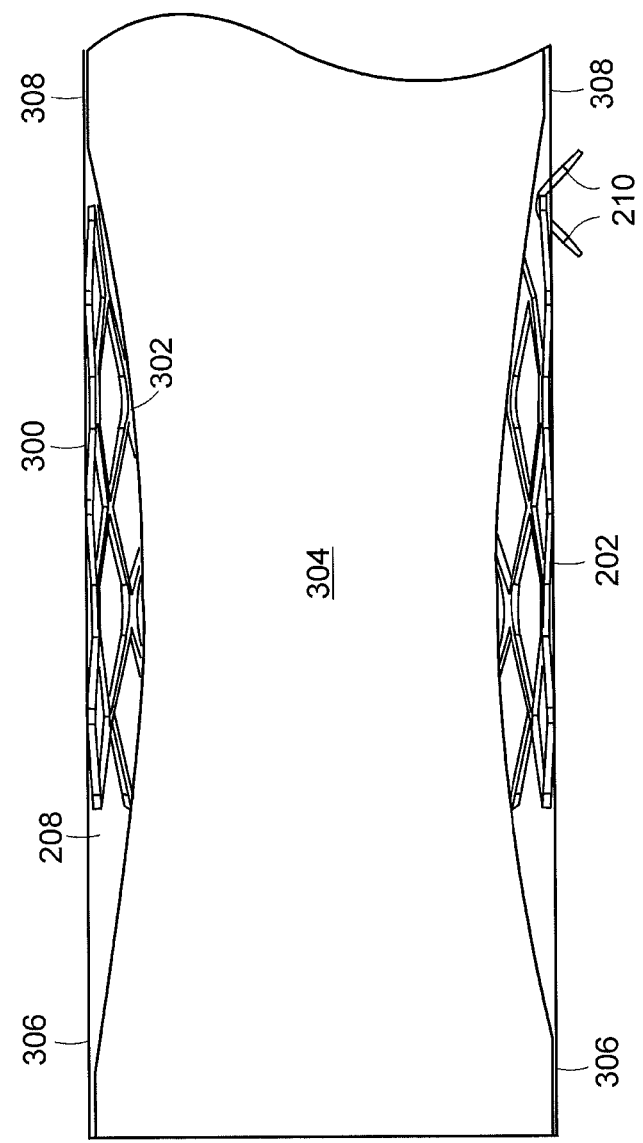
FIG. 3B is a cross-sectional view as taken along line A-A of FIG. 3A showing the stent and first inner layer and second outer layer of the sleeve shown in FIG. 2.

FIG. 3A is a plan view of the proximal portion of the gastrointestinal implant device shown in FIG. 2. FIG. 3B is a cross-sectional view as taken along line AA of FIG. 3A showing the stent 208 and the first outer layer 300 and the second inner layer 302 of the sleeve 202 shown in FIG. 2. As described in conjunction with FIG. 2, the sleeve 202 includes a first outer layer 300 and a second inner layer 302. The first outer layer 300 is bonded to the second inner layer 300 at positions 306 below the distal end of the stent 208 and at positions 308, above the proximal end of the stent 208. A passageway 304 inside the second inner layer 302 of the sleeve 202 allows passage of chyme through the sleeve 202. The stent 208 is sandwiched between the first outer layer 300 and the second inner layer 302 at the proximal end of the sleeve 202 and is free to move at the distal end within the first outer layer 300 and the second inner layer 302 of the sleeve 202. The covered exterior surface of the stent 208 prevents tissue growth to allow removal of the implant device 200. The covered interior surface of the stent 208 provides a smooth passageway for chyme to bypass the duodenum 104.

FIG. 4 is a perspective view of the gastrointestinal implant device 200 with the first outer layer 300 of the sleeve 202 removed. The interconnecting struts which form the mesh (a network of struts) with diamond spaced openings are sufficiently flexible to allow the stent to be collapsed inside a delivery catheter and have sufficient elasticity to hold the pylorus open once the catheter is withdrawn. The force needed to hold the pylorus open is about 1-2 lbs. of radial force outward when the stent is compressed from its full diameter by 25%.

Figure 5:
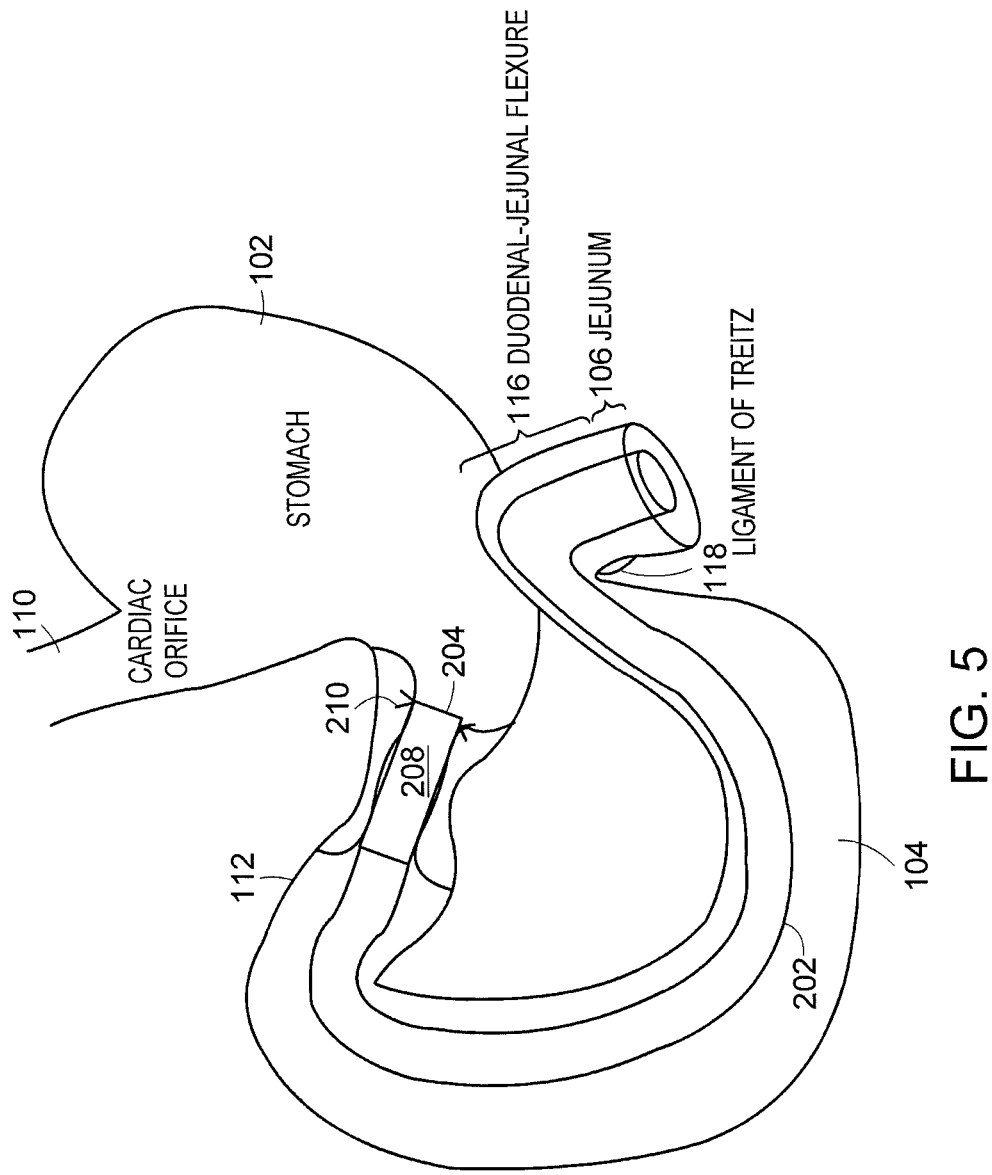
FIG. 5 is a sectional view of a body showing the gastrointestinal implant device implanted in the digestive system.

FIG. 5 is a sectional view of a body showing the gastrointestinal implant device 200 implanted in the digestive system. The first proximal end 204 of the implant device 200 is anchored to muscle in the pyloric portion of the stomach 102. The barbs 210 grip onto the muscle to anchor the implant device 200 in place so that the implant device 200 can not be dragged into the stomach or down into the intestines with movement of the stomach and the intestines.

The sleeve 202 extends over the ligament of Treitz 118 beyond the proximal jejunum. Extending the sleeve below the ligament of Treitz reduces the likelihood that the sleeve will move back through the duodenum 104 toward the stomach 102.

After the gastrointestinal implant device 200 has been placed in the body and anchored in the pyloric portion of the stomach, chyme leaving the stomach passes through passageway 304 (FIG. 3B) inside the sleeve 202 and bypasses the duodenum and proximal jejunum. By directing the chyme through the sleeve 202 the digestion and the absorption process in the duodenum is interrupted. By interrupting mixing of the chyme with juices in the duodenum, partially digested food material is not broken down into particles small enough to be absorbed by the body. Further, there is no mixing of bile with the chyme until the chyme reaches the jejunum. The absorption of fats and carbohydrates is reduced by delaying the mixing of bile with the chyme.

The pyloric valve opens periodically to allow chyme to exit the stomach 102 to the duodenum 104. In one embodiment of the invention the length of the stent 208 is selected to keep the pyloric valve permanently open to induce "dumping syndrome". By keeping the pylorus open, the chyme empties rapidly into the sleeve 202 and passes down through the sleeve and into the jejunum with minimal digestion. This results in a "dumping syndrome" which is a reaction to excessive rapid dumping of chyme into the jejunum causing the patient to feel ill, dizzy and nauseated. This syndrome is particularly enhanced when sugars and carbohydrates are eaten and passed directly into the jejunum.

To hold the pyloric valve open, the length of the stent should be at least 1.5 inches so that the stent extends from the anchoring position in the pyloric portion of the stomach through the pyloric orifice 108 (the opening from the stomach while the pyloric valve is open). The length of the stent is selected so that the distal end of the stent is above the papilla of vater 114 (FIG. 1). As shown, the stent 208 extends through the pyloric orifice 108 to hold the pyloric valve permanently open. In an alternative embodiment, the length of the stent 208 is selected such that the stent 208 ends at the stomach side of the pyloric orifice 108 allowing the pyloric valve to operate normally.

The sleeve 202 provides weight loss mechanisms by providing negative feedback, reduced fat digestion and reduced desire for food. The reduced fat digestion occurs because the sleeve 202 delays the mixing of bile and pancreatic juices with chyme from the stomach until after the chyme leaves the sleeve. The reduced desire for food may occur because the sleeve 202 blocks hormonal release from the duodenum.

After the chyme from the stomach has passed through the sleeve, the sleeve becomes extremely thin and floppy, permitting the sleeve to contour to the inner walls of the intestine. The sleeve is non-compliant and drapes away from the intestinal walls thereby permitting the pancreatic juice to flow unimpeded into the duodenum through the papilla of vater. The normal peristalsis of the bowel is used to propel the chyme through the intestines.

Figure 6:
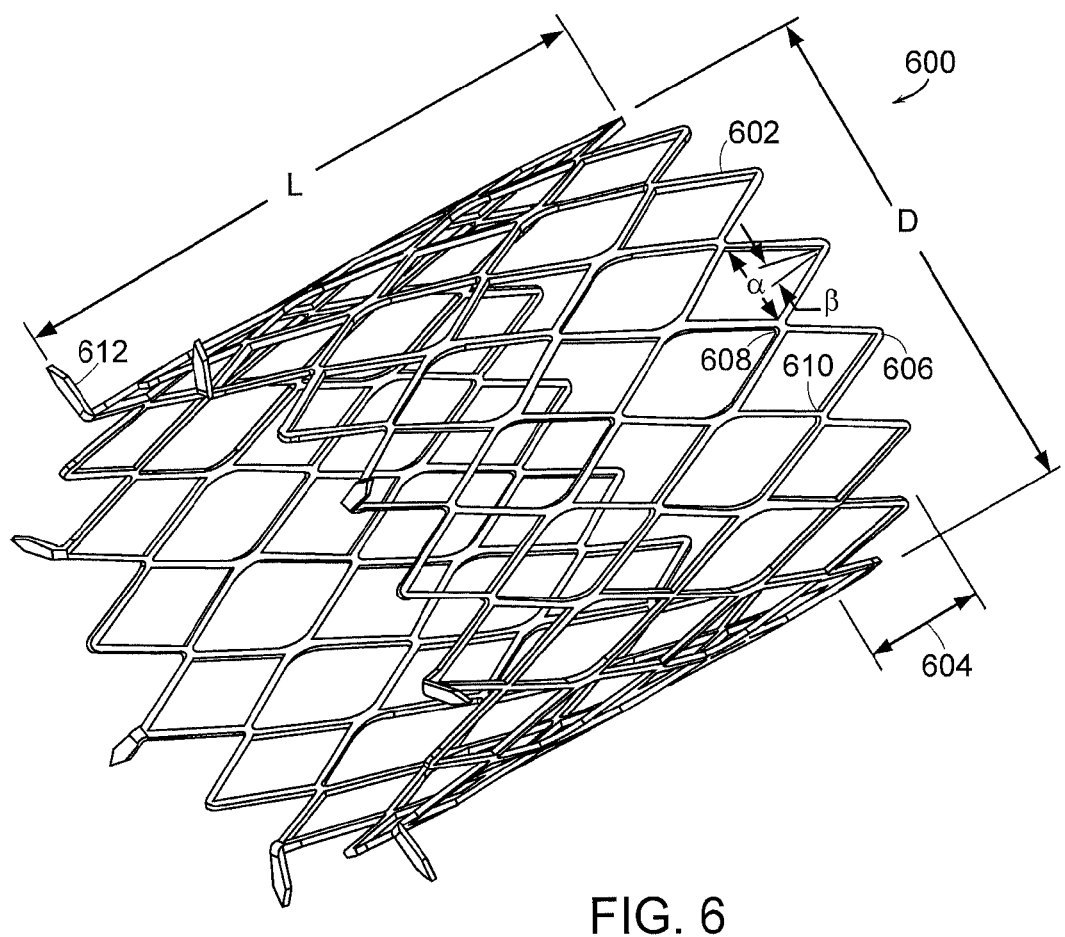
FIG. 6 is a perspective view of a collapsible self-expanding stent in the gastrointestinal implant device.

FIG. 6 is a perspective view of a collapsible self-expanding stent 600 in the gastrointestinal implant device 200 shown in FIG. 2 when expanded. The stent 600 is non-woven, collapsible and self-expanding, allowing endoscopic insertion and removal of the implant device 200. The stent 600 includes a plurality of flat struts 602 forming an open space pattern to ease collapsing while ensuring self-expansion. The open space pattern allows for collapsing into a catheter for endoscopic delivery and removal. The struts 602 may be manufactured from heat-treated spring steel such as Nitinol or MP35N.

In the embodiment shown, the stent has a length L of about 1.5 inches and has a diameter D of about 1 inch. The struts 602 are flat, about 0.010 inches wide and about 0.004 to 0.010 inches thick. The stent can be formed from a tube of material by laser cutting followed by expansion and heat setting, or other methods well known to those skilled in the art.

In an alternate embodiment, the struts 602 can be formed separately and the strut intersections can be welded or attached by other means well known to those skilled in the art. Visually the struts form sections 604 around the circumference of the stent. Each section has a series of triangles with each triangle defined by one distal strut connection 606 and two proximal strut connections 608, 610. The ratio of the collapsed diameter to the expanded diameter of the stent is roughly 1:4.

When expanded, the angle α between divergent strut sections is about 45-50 degrees and the diameter of the stent is about one inch. When compressed, the angle β between divergent strut sections is about 5-6 degrees to reduce the diameter of the stent to about 0.21 inch for endoscopic delivery and removal. The elasticity of the struts permits this compression. When the radial compression is released, the elasticity of the struts causes the stent to expand to diameter D. The stent assumes its desired diameter as the elastic restoring forces seek their minimum stress.

The ends of the struts at the proximal end of the stent 600 are elongated and shaped to provide barbs 612 to anchor to the muscle in the pyloric portion of the stomach 102.

Figure 7:
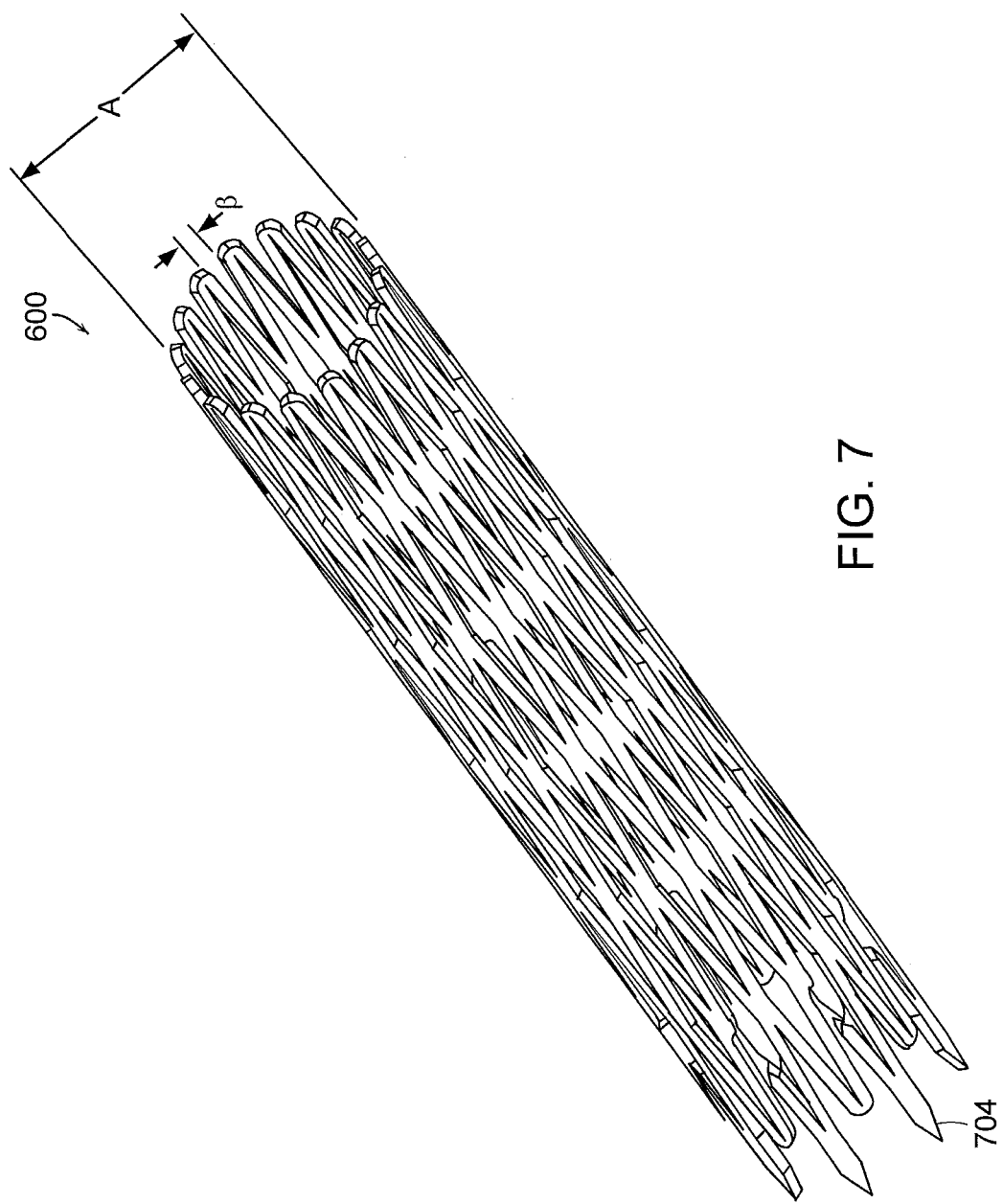
FIG. 7 is a perspective view of the stent shown in FIG. 6 when compressed.

FIG. 7 is a perspective view of the stent 600 shown in FIG. 6 when compressed. The stent 600 is compressed until the angle β between divergent strut sections is about 5-6 degrees to reduce the diameter D of the stent 600 to about 0.21 inch for endoscopic delivery and removal. The barbs 704 at the proximal end of the stent are elongated. The barbs 704 can be shaped to anchor the stent to the muscular pylorus.

Figure 8:
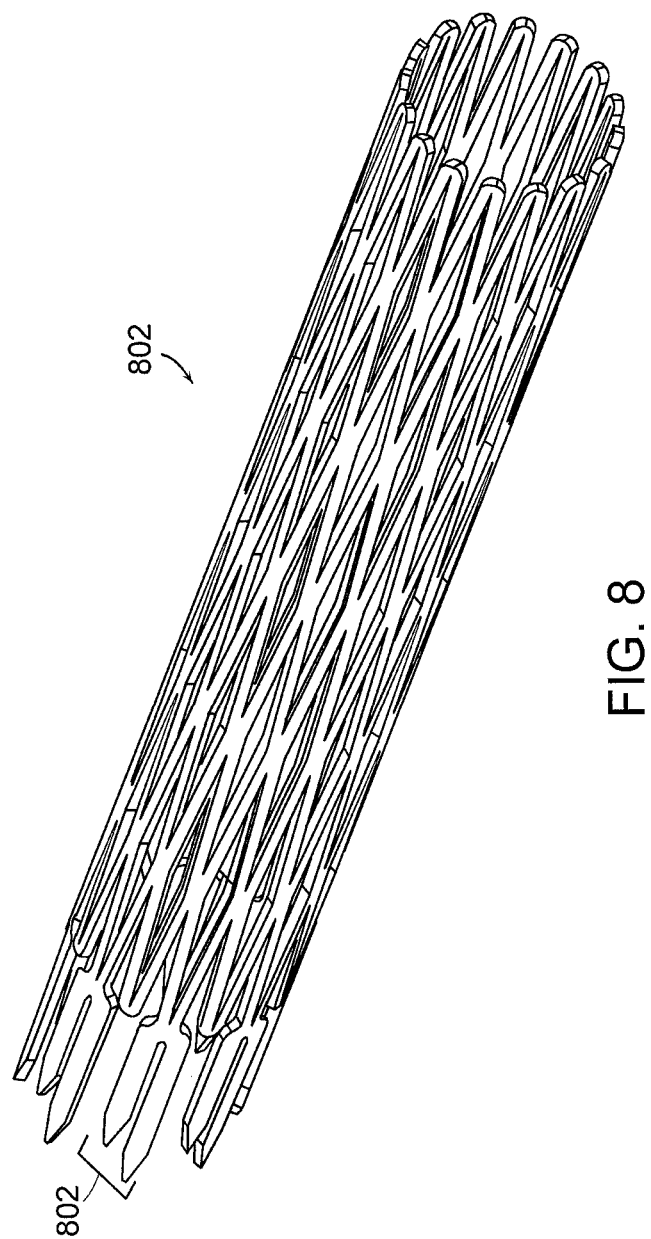
FIG. 8 is a perspective view of another embodiment of a stent when compressed.

FIG. 8 is a perspective view of another embodiment of a stent 800 when compressed. Pairs of barbs 802 at the proximal end of the stent 800 are elongated and can be shaped to provide opposed barbs to anchor the stent 800 in the muscle of the pylorus.

Figure 9:
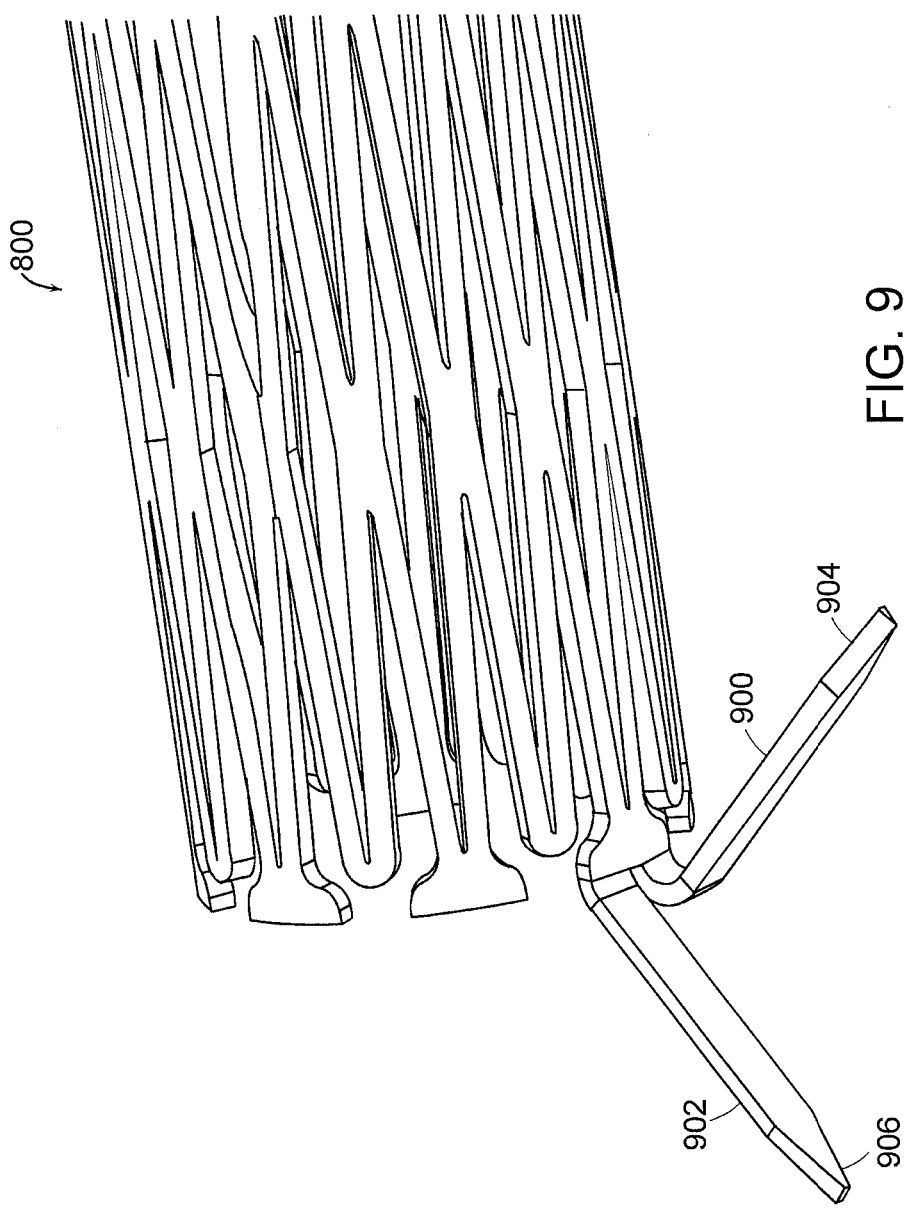
FIG. 9 is a perspective view of the stent shown in FIG. 8 with the strut ends bent to provide opposed barbs.

FIG. 9 is a perspective view of the compressed stent 800 shown in FIG. 8 with the strut ends 902, 900 bent to provide opposed barbs 904, 906. The barbs 904, 906 engage the muscle of the pylorus to anchor the gastrointestinal implant device in the pylorus portion of the stomach. As shown in FIG. 2, the strut ends 900, 902 protrude outward from the outer surface of the stent 800 in opposite directions. They may be perpendicular to each other. The barbs 904, 906 at the ends of the respective opposed strut ends 900, 902 dig into the pylorus muscle to anchor the stent. The barbs 904, 906 at the end of the protruding opposed strut ends 900, 902 prevent movement of the stent 800 in either direction; that is, they prevent movement of the stent 800 into the stomach and prevent movement of the stent 800 down through the duodenum.

Figure 10:
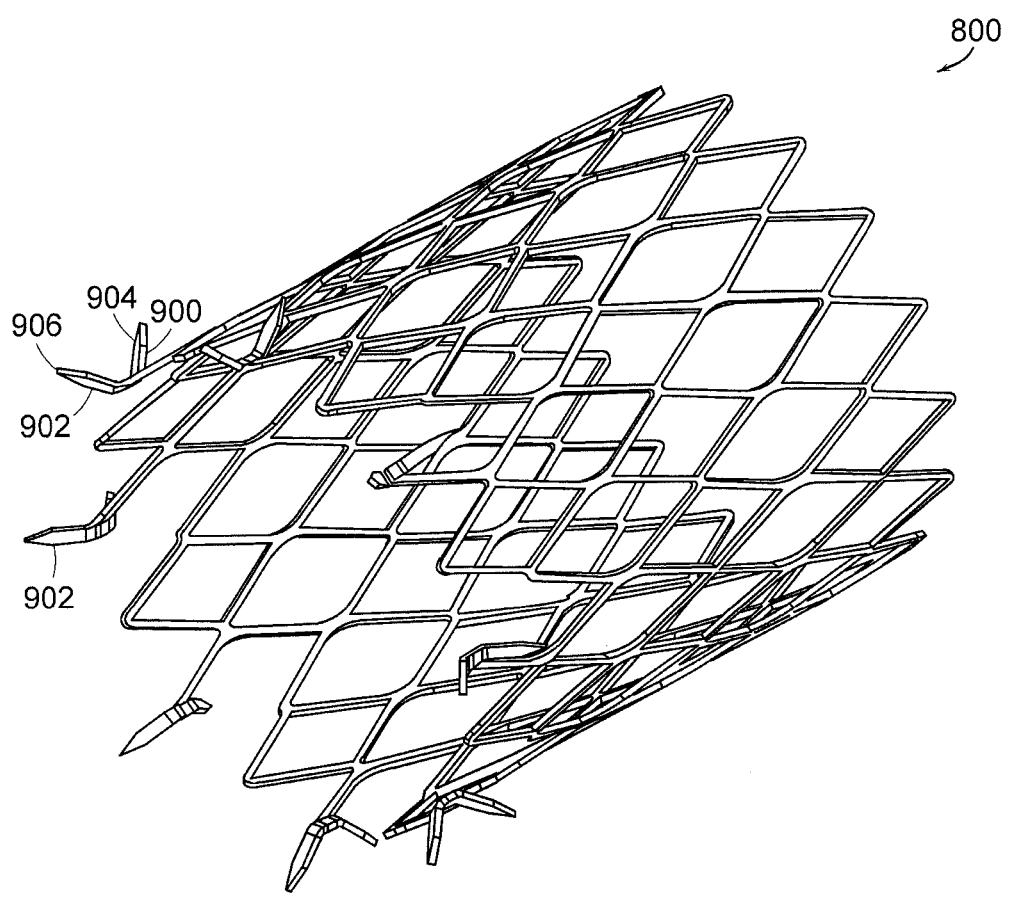
FIG. 10 is a perspective view of the stent shown in FIG. 8 when expanded.

FIG. 10 is a perspective view of the stent 800 shown in FIG. 8 when expanded. As discussed in conjunction with FIG. 9, the opposed strut ends 904, 906 engage the muscle of the pylorus while the stent 800 is expanded. In the engaged position, the barbs 904, 906 spread radially outward from the longitudinal axis of the stent 800 such that the tips of the barbs come into contact and engage the tissue.

Figure 11:
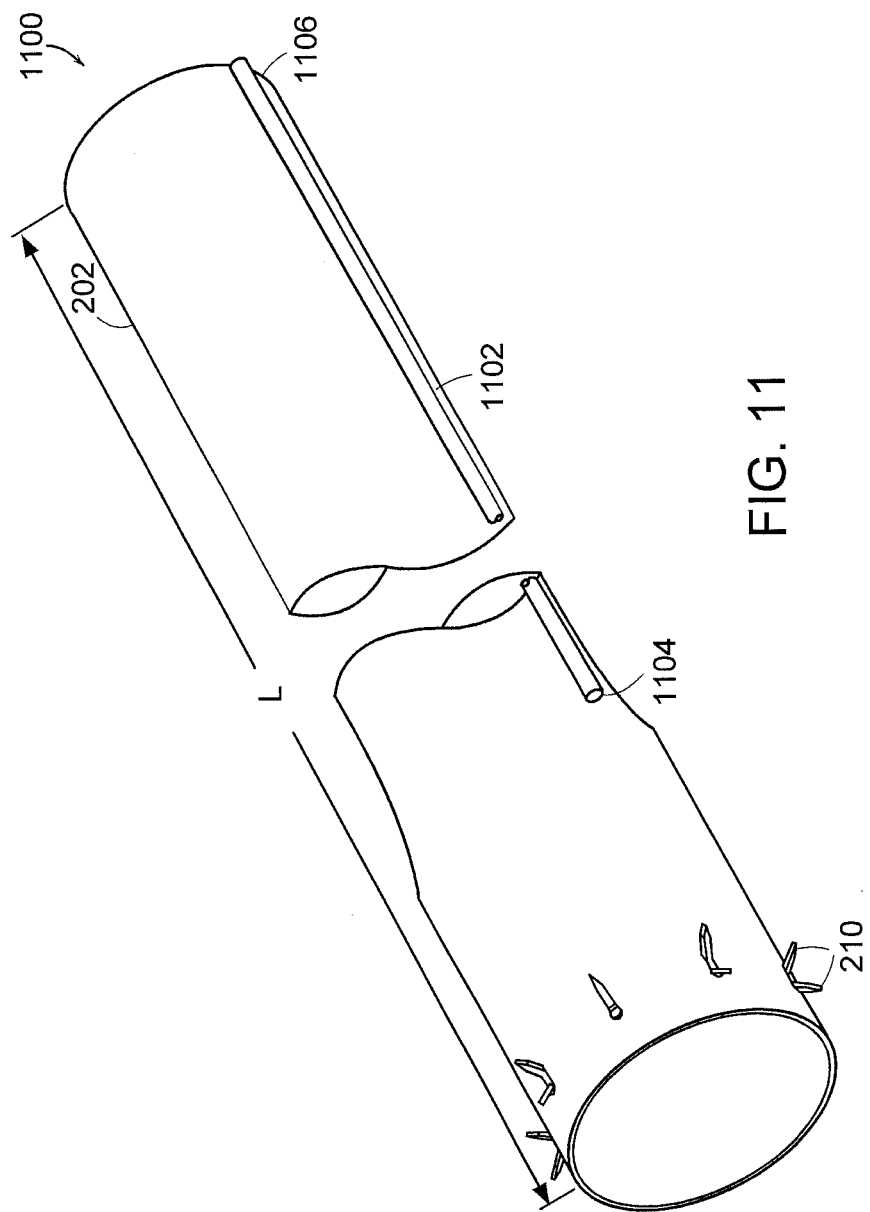
FIG. 11 illustrates the gastrointestinal device shown in FIG. 1 including an anti-buckling mechanism.

FIG. 11 illustrates the gastrointestinal device 1100 shown in FIG. 1 including an anti-buckling mechanism 1102. A flexible, anti-rotation, anti-buckling mechanism 1102 is attached to the sleeve 202 and extends from below the distal end of the stent along the length L of the sleeve to the distal end of the sleeve 202. In the embodiment shown, the anti-buckling mechanism 1102 is a guidewire device attached to the exterior surface of the outer layer of the flexible sleeve. Guidewire devices are well known to those skilled in the art. A first proximal end of the guidewire device 1104 is attached below the stent and a second distal end of the guidewire device 1106 is attached to the distal end of the flexible sleeve. The diameter of the guidewire ranges from about 0.010" to about 0.016".

The gastrointestinal implant device 200 is designed for endoscopic placement. FIG. 12 is a perspective view of a portion of a catheter system 1200 for delivery of the gastrointestinal implant device. The catheter system follows a guide wire 1212 through the esophagus and the stomach to the pylorus portion of the stomach. The guide wire 1212 enters a first inner lumen at the proximal end 1208 of the catheter system 1200 and exits the first inner lumen at the distal end 1222 of the catheter system 1200.

The catheter system 1200 includes an outer sheath 1202 for storing the stent 208 in collapsed form, a flange 1216 to pull back the outer sheath 1202 and a sleeve retention wire mechanism 1224 for releasing a sleeve retention wire 1210 from the proximal end of the flexible sleeve 202 after the stent has been released from the outer sheath 1202.

As described in conjunction with FIG. 2, the distal portion of the gastrointestinal implant device includes a flexible sleeve 202 which can negotiate the duodenum and the jejunum. A sleeve retention wire 1210 travels through a second inner lumen and exits the second inner lumen to secure the distal end of the sleeve 202 to an inner sheath 1226. The sleeve retention wire 1210 is coupled to the sleeve retention wire release mechanism 1224 for releasing the sleeve retention wire 1210 after the gastrointestinal implant device has been positioned in the pyloric section of the stomach. The release mechanism 1224 will be described later in conjunction with FIG. 16B.

The sleeve 202 is secured temporarily outside the inner sheath 1226 allowing for proper positioning of the gastrointestinal implant device and then for release. As shown, the sleeve 202 is secured by the sleeve retention wire 1210 using a dead-bolt mechanism 1206. Non-stick coatings such as Teflon on the sleeve retention wire 1210 are preferred to make release easier to accommodate tortuous anatomical pathways. The sleeve retention wire 1210 extends through the second inner lumen from the release mechanism 1224 of the catheter system 1200 to the dead-bolt mechanism 1206. The dead-bolt mechanism 1206 is described later in conjunction with FIG. 14A. The sleeve retention wire 1210 holds the sleeve in position. The distal end of the folded sleeve is released by the release mechanism 1224 by pulling the sleeve retention wire 1210 backward from the proximal end 1208 of the catheter.

As described in conjunction with FIG. 2, the proximal portion of the gastrointestinal device includes a covered stent. The covered stent does not enter the duodenum and thus is stiffer than the sleeve because it remains in the pylorus of the stomach. The stent in the gastrointestinal implant device is collapsed and stored in the outer lumen within the outer sheath 1202 between the flange 1216 and the proximal end 1208 of the outer sheath 1202. The stent is supported in a collapsed form by the outer sheath 1202. The catheter 1200 is inserted into the digestive system through the esophagus to the pyloric section of the stomach. The proximal end of the outer sheath 1202 is positioned in the stomach, in the pylorus through the use of positioning ring 1240. After the outer sheath 1202 has been positioned, the stent is retracted from the outer lumen of the catheter by pulling flange 1216 toward the proximal end of the catheter system 1200. Upon release, the stent self-expands by its own elastic restoring force to engage the anchor portion with the stomach muscle at the pyloric section of the stomach.

FIG. 13 is a cross-sectional view of the inner shaft 1226 taken along line E-E of FIG. 12. The sleeve retention wire 1210 passes through a second inner lumen 1314 in the inner sheath 1226. The sleeve retention wire 1210 exits the second inner lumen 1314 and is threaded through folds of the sleeve 202 at 1302 in FIG. 14A. The sleeve retention wire 1210 re-enters the second inner lumen 1314 at 1302 (FIG. 14A). The guidewire 1212 passes through the first inner lumen 1310.

FIG. 14A is an expanded perspective view of the dead-bolt mechanism 1206 shown in FIG. 12. The sleeve 202 has been folded for delivery. The sleeve is wrapped around the inner sheath 1226 and bunched above the inner sheath 1226. The sleeve is held in folded position around the inner sheath 1226 by threading the sleeve retention wire 1210 through the folds of the sleeve 202. The sleeve retention wire 1210 exits the second inner lumen 1314 through an opening 1304 and pierces through folds of the sleeve 202 at 1304. Threading the sleeve retention wire 1210 through the folds of the sleeve 202 results in a plurality of small holes at the distal end of the sleeve 202. The holes are reinforced with silicone or urethane to avoid tears in the material. The sleeve retention wire 1210 re-enters the second inner lumen through a second hole 1302 and advances a sufficient distance within the second inner lumen toward the distal end of the second inner lumen to resist pulling out of the second inner lumen.

FIG. 14B is a sectional view of the dead-bolt mechanism 1206 shown in FIG. 14A illustrating the sleeve retention wire 1210 threaded through the sleeve. The sleeve retention wire 1210 exits the second inner lumen at 1306 and pierces through folds in the sleeve 202 at 104. The sleeve retention wire 1210 re-enters the second inner lumen at 1302.

Figure 15:
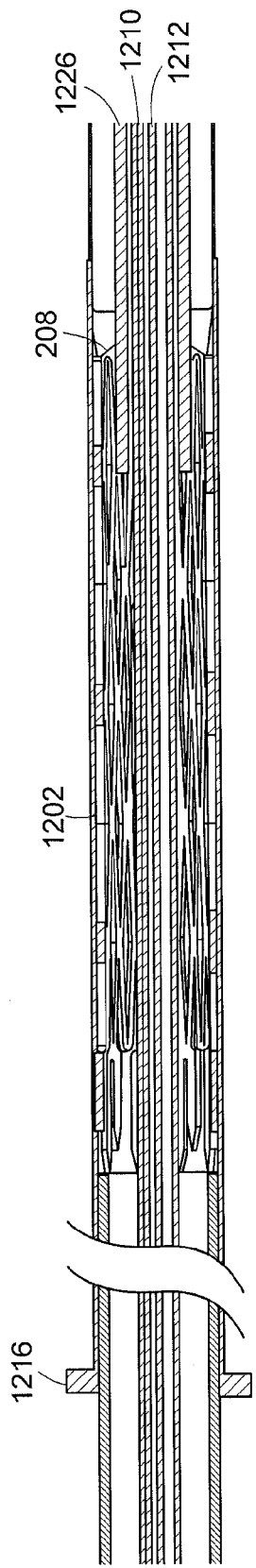
FIG. 15 is sectional view of a portion of the catheter system illustrating the collapsed stent stored inside the outer sheath.

FIG. 15 is a sectional view of a portion of the catheter system shown in FIG. 12 illustrating the collapsed stent 208 stored inside the outer sheath 1202. The stent 208 is pre-compressed and held in a collapsed form inside the outer sheath 1202 of the catheter. The outer sheath 1202 is pulled back by the flange 1216 toward the proximal end of the catheter system 1200 to release the self-expanding stent 208. The stent radially expands under its own elastic restoring force. The guidewire 1212 is directed through the first inner lumen and the sleeve retention wire 1210 is directed through the second inner lumen in the inner sheath 1226. The inner sheath includes a first lumen through which the guidewire passes and a second lumen through which the sleeve retention wire passes.

Figure 16A:
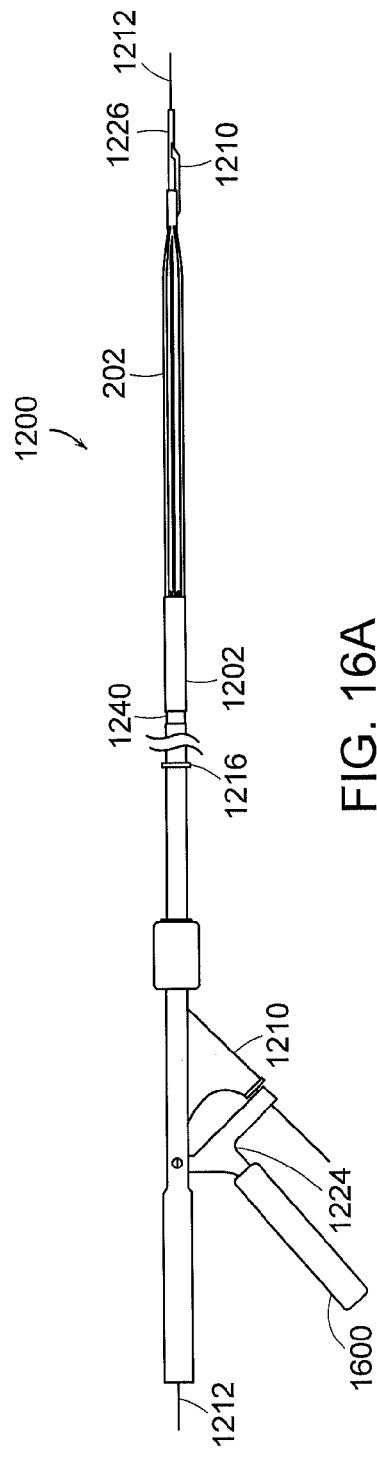
FIG. 16A is a plan view of the catheter system illustrating the collapsed stent stored inside the outer sheath of the gastrointestinal implant device.
Figure 16B:
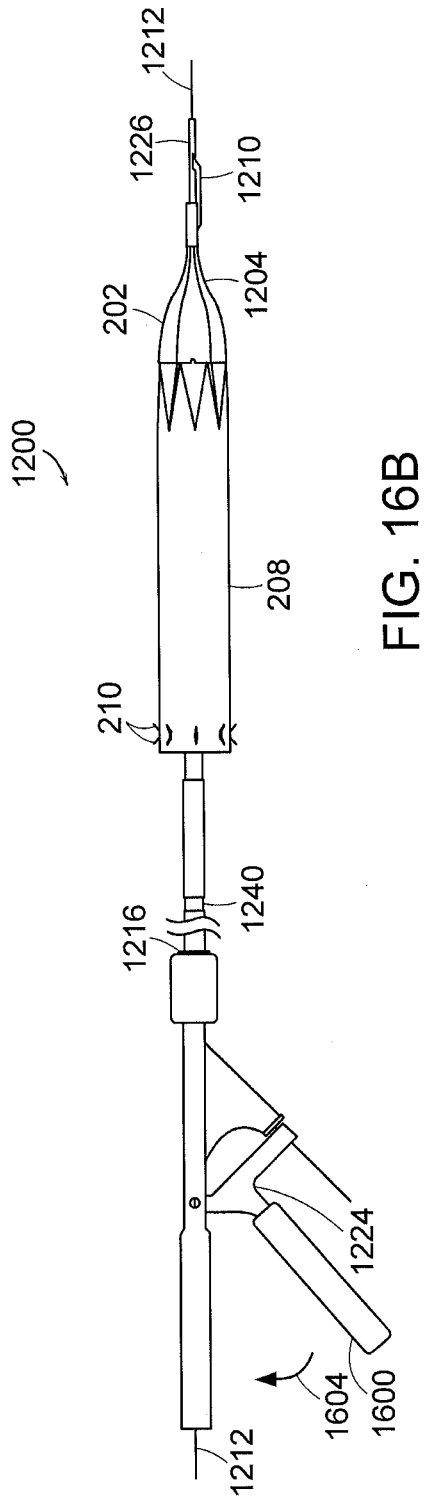
FIG. 16B is a plan view of the catheter system illustrating the gastrointestinal implant device after release of the stent from the outer sheath.
Figure 16C:
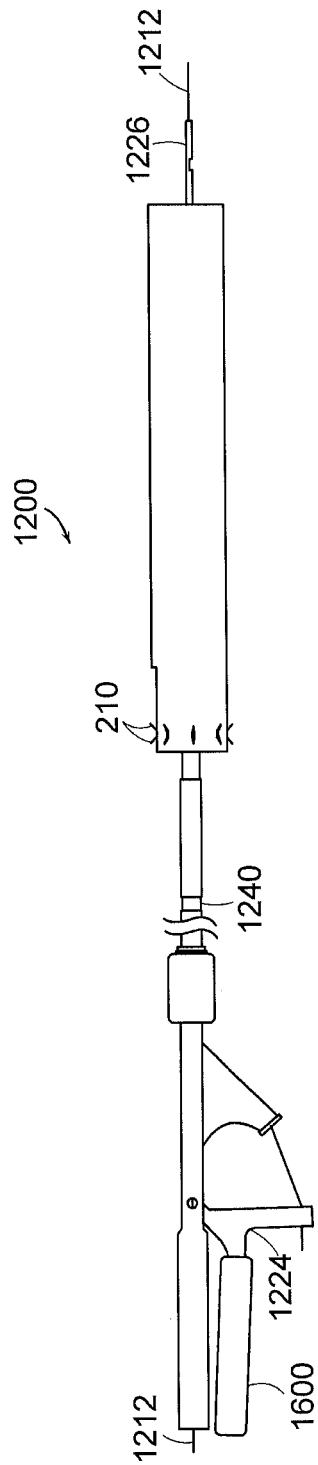
FIG. 16C is a plan view of the catheter system illustrating the expanded gastrointestinal implant device after the sleeve retention wire has been released.

FIGS. 16A-C illustrate a method for delivery of the gastrointestinal implant device. FIG. 16A is a plan view of the catheter system illustrating the collapsed stent stored inside the outer sheath 1202 of the gastrointestinal implant device. As described in conjunction with FIG. 12, the stent 202 is stored inside the outer sheath and the distal end of the sleeve 202 is secured outside the inner sheath 1226 by a sleeve retention wire 1210.

FIG. 16B is a plan view of the catheter system illustrating the gastrointestinal implant device after release of the stent from the outer sheath. The flange 1216 has been pulled back toward the proximal end of the catheter system 1200 to pull back the outer sheath 1202 from the stent and the stent 208 has self-expanded. The sleeve retention wire 1210 holds the distal end of the sleeve 202.

Once in place, the sleeve retention wire 1210 can be removed. As described previously in conjunction with FIG. 12, the sleeve retention 1210 is coupled to locking mechanism 1224. Handle 1600 in the locking mechanism 1224 acts as a pivot device to pull the sleeve retention wire 1210 from the dead-bolt mechanism 1206. The distal end of the gastrointestinal implant device is released by moving handle 1600 in a clockwise direction 1604. As the handle 1600 is moved in direction 1604, the sleeve retention wire 1210 threaded through the folds of the sleeve is pulled back through the second inner lumen 1314 and disengages from the sleeve at the distal end of the gastrointestinal implant device. The sleeve retention wire 1206 extends from the distal end of the gastrointestinal implant device through the second inner lumen 1314. The wire is connected to the handle 1600 at the proximal end of the catheter.

FIG. 16C is a plan view of the catheter system illustrating the expanded gastrointestinal implant device after the sleeve retention wire has been released. The handle 1600 has been moved in a clockwise direction and the sleeve retention wire 1210 pulled back through the second inner lumen 1314 to release the distal end of the sleeve 202.

Figure 17:
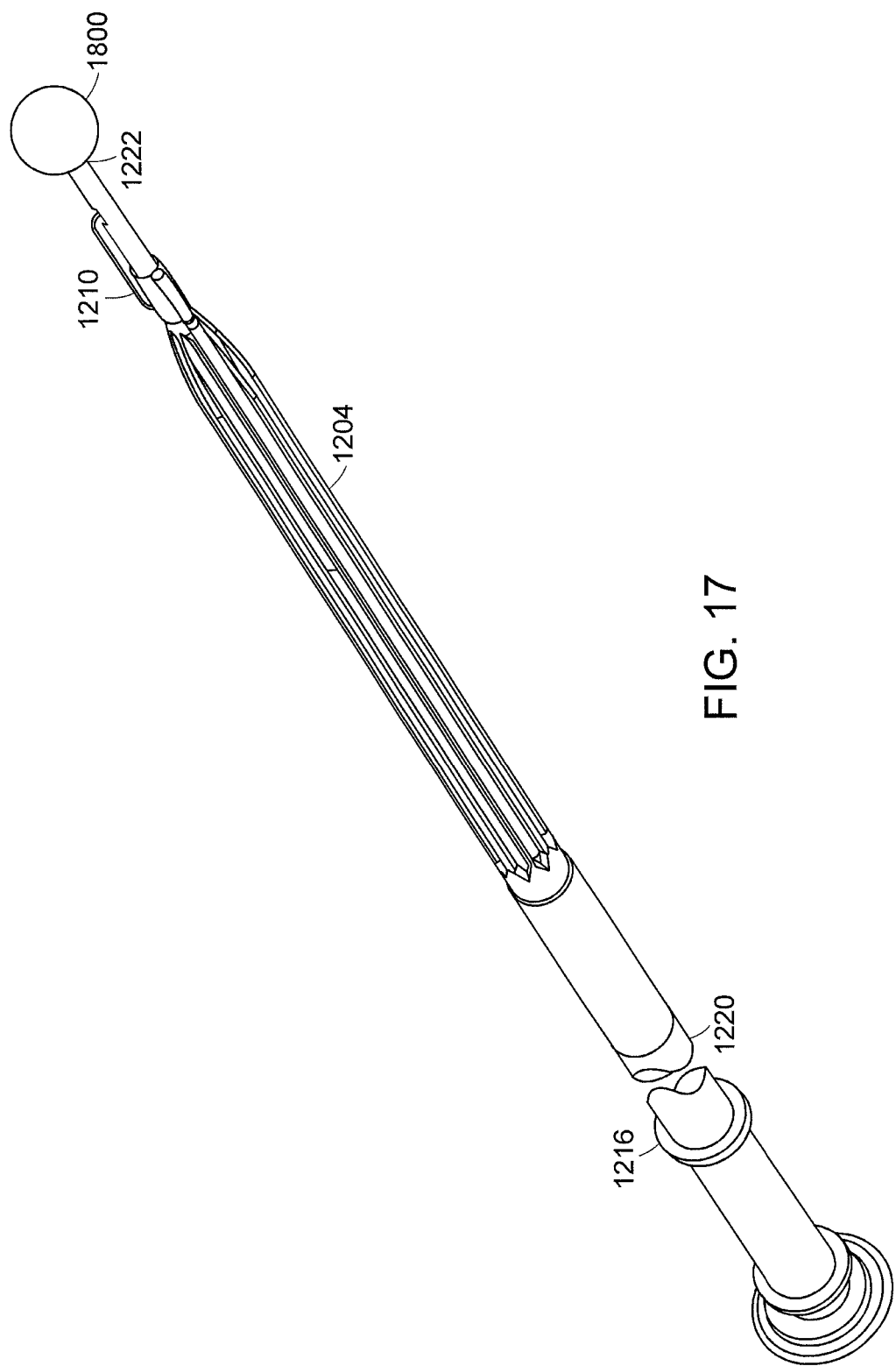
FIG. 17 is a perspective view of another embodiment of the catheter system shown in FIG. 12.

FIG. 17 is a perspective view of another embodiment of the catheter system shown in FIG. 16. The catheter includes a ball 1800 coupled to the distal end 1222 of the inner sheath 1226 for guiding the catheter through the alimentary canal to the pyloric portion of the stomach. The ball 1800 is small enough so that it can be pulled back through the gastrointestinal implant device after the gastrointestinal device has been delivered, the stent expanded and the sleeve retention wire 1210 has been released. The sleeve is shown uniformly folded. However, the sleeve may not necessarily be uniformly folded.

Figure 18:
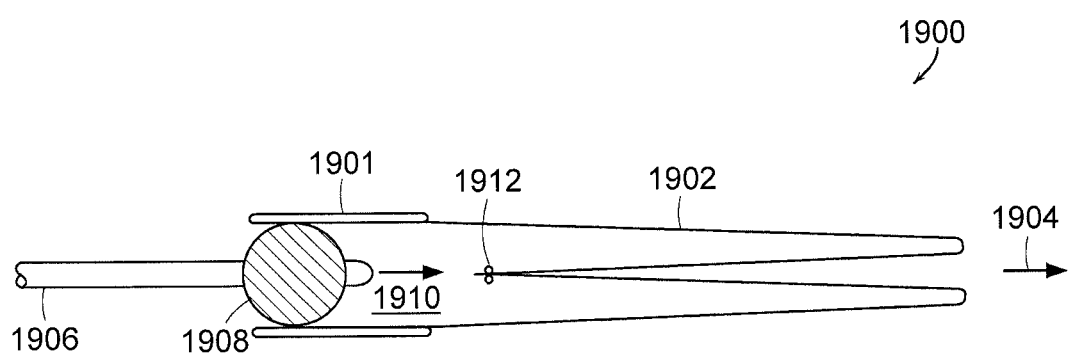
FIG. 18 is a sectional view of an everting catheter system for delivery of a longer length sleeve.

FIG. 18 is a cross-section of an everting catheter system 1900 for delivery of a longer flexible sleeve. The gastrointestinal implant device 200 is shown with the stent sleeve anchor 1901 and the attached sleeve 1902 shown as delivered into the anatomy. The delivery catheter previously described is then removed. A balloon catheter 1906 is introduced into the stent sleeve anchor 1901 and the balloon 1908 inflated to seal the lumen of the stent 1901. The sleeve 1902 is folded inside itself and an elastic band 1912 is used to seal the end of the sleeve. Fluid is then injected through the balloon catheter shaft 1906 into the sleeve lumen 1910, filling the lumen and pressurizing it. The pressure of the fluid is used to push the inner sleeve distally towards 1904. When the sleeve 1902 has fully deployed distally, the elastic band 1912 falls off of the closed end of the sleeve 1902 and passes distally in the intestine until it is excreted. This mechanism permits deployment of a sleeve that is double the length of the delivered device. This may be needed as it is difficult to access the distal parts of the intestine with guidewires. This everting catheter system enables delivery of longer sleeves than are possible using only the delivery catheter described in conjunction with FIG. 12.

Figure 19:
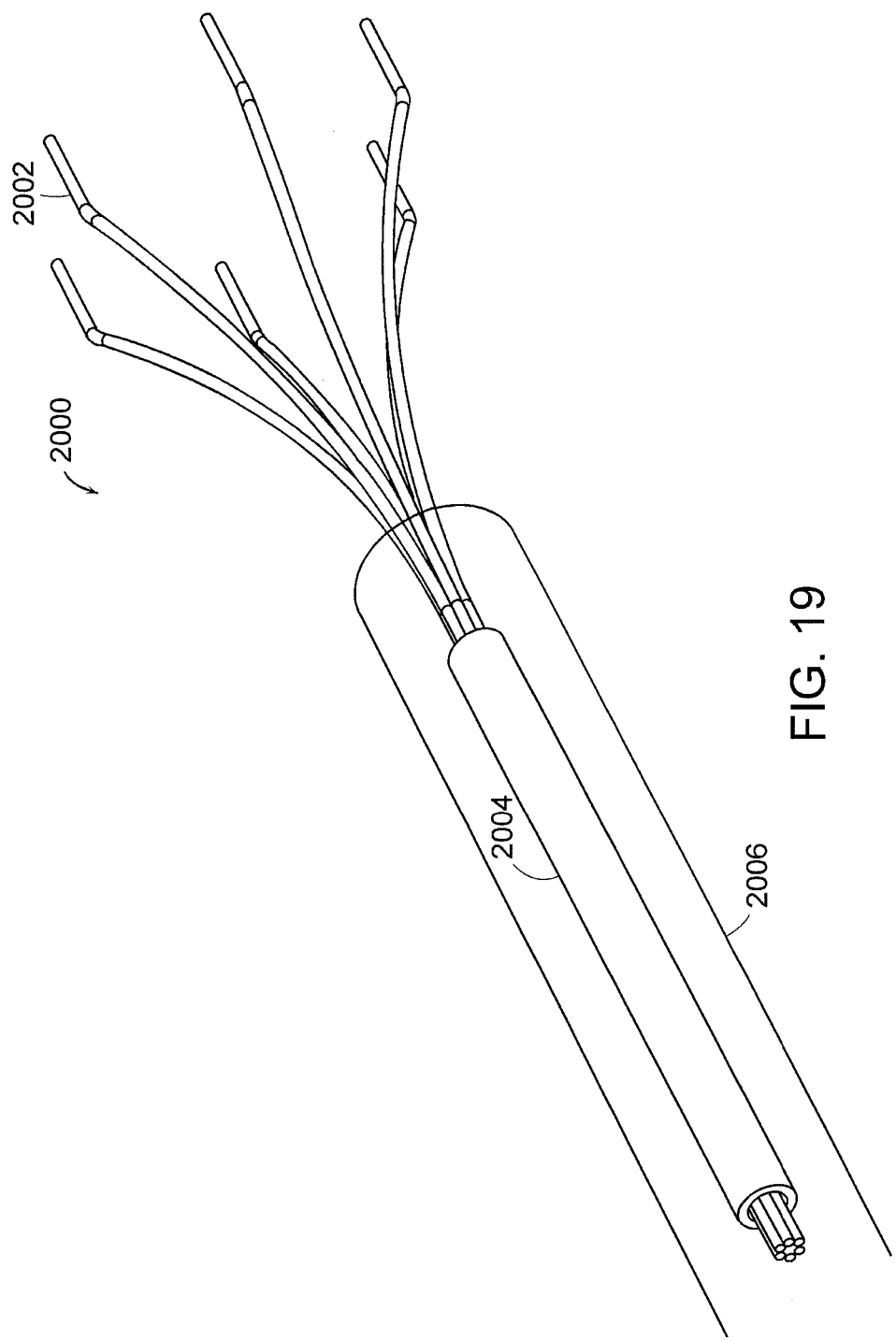
FIG. 19 is a perspective view of a retrieval device for removing the gastrointestinal implant device from the digestive tract.

FIG. 19 is a perspective view of a retrieval device 2000 for removing the gastrointestinal implant device 200 from the digestive tract. As already described, the exterior surface of the stent 208 is covered with a material that prevents cellular in-growth allowing the stent 208 to be easily removed. The retrieval device 2000 includes an inner sheath 2004 and an outer sheath 2006. A plurality of fingers 2002 extend from the proximal end of the inner sheath 2004. The fingers 2002 engage the exterior surface of the gastrointestinal device. As the inner sheath 2004 is moved down over the fingers, the fingers 2002 pull radially inward to reduce the proximal stent diameter and pull the collapsed device into the outer sheath 2006.

Figure 20:
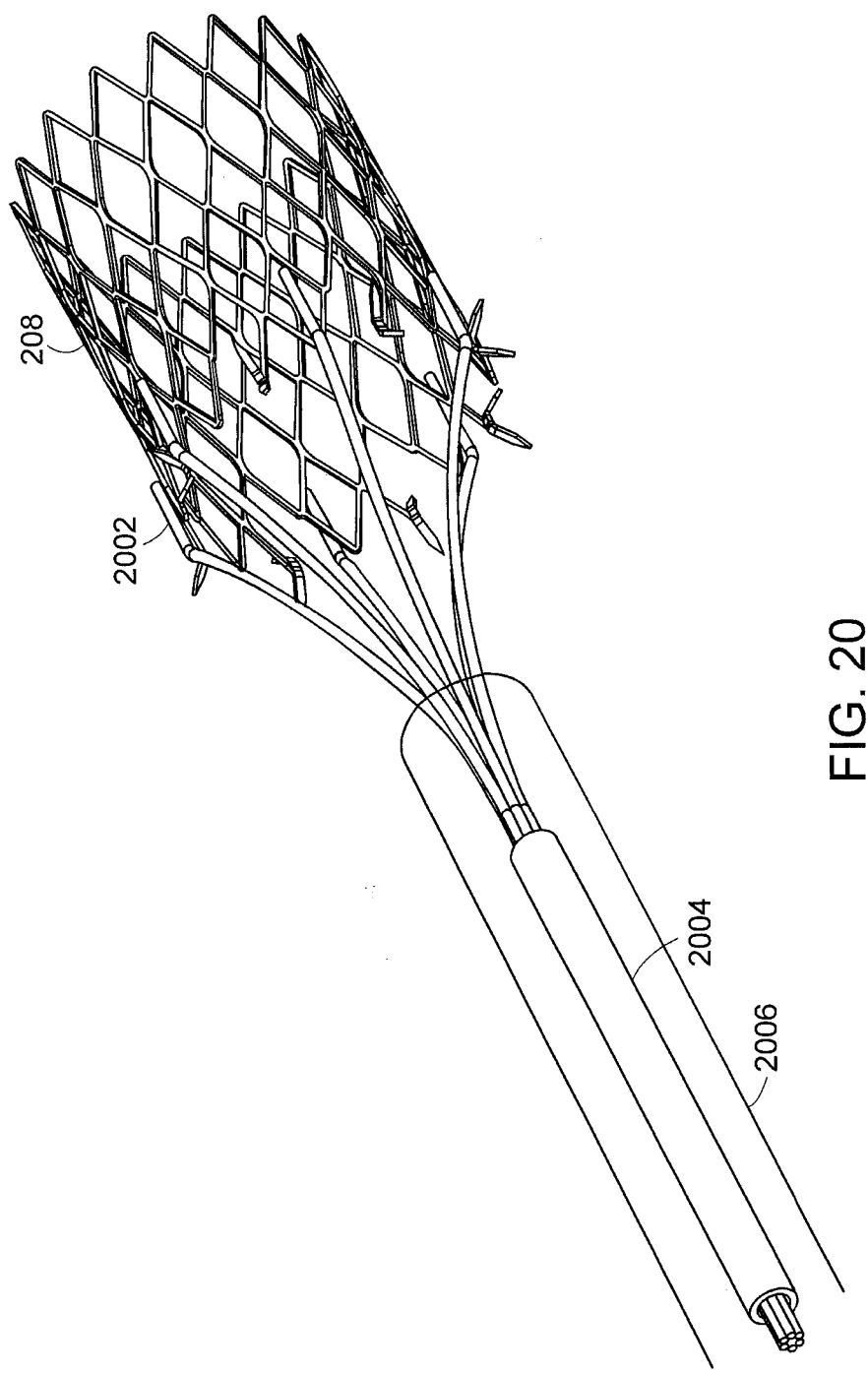
FIG. 20 is a perspective view of the removal device engaged with the stent.

FIG. 20 is a perspective view of the retrieval device 2000 engaged with the stent 208. The fingers 2002 of the retrieval device are positioned around the stent 208. As the inner sheath 2004 is pushed over the fingers 2002, the fingers pull radially inward on the proximal end of the stent 208 and the proximal end of the stent 208 is collapsed. After the stent 208 has been collapsed sufficiently such that the proximal stent diameter is less than the diameter of the outer sheath 2006, the stent is drawn into the outer sheath 2006. The entire gastrointestinal implant device can then easily be removed from the patient by pulling retrieval device 2000 through the stomach and the esophagus.

Figure 21:
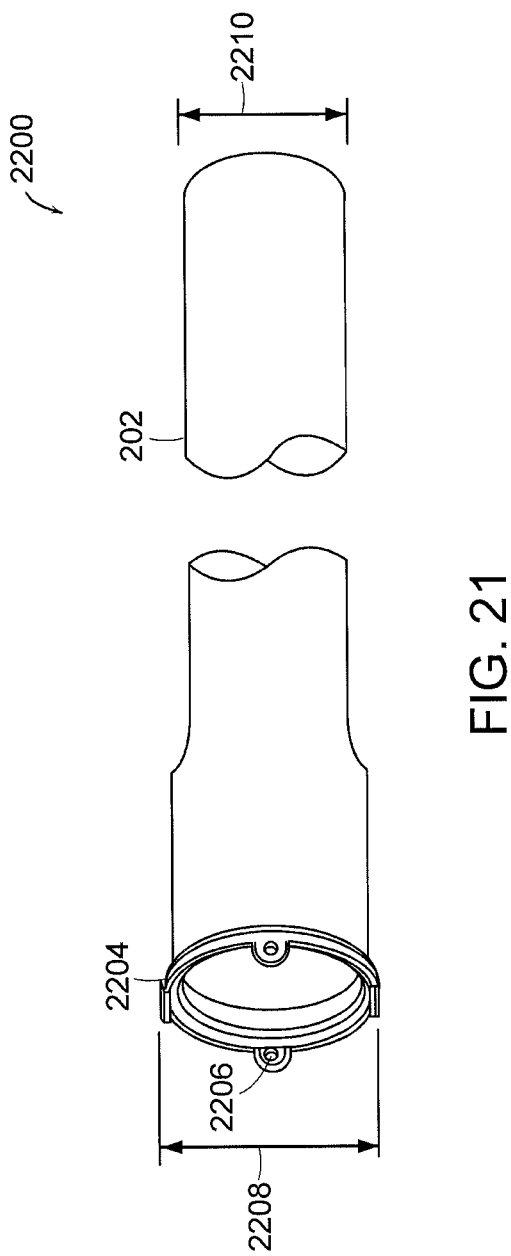
FIG. 21 is a perspective view of another embodiment of a gastrointestinal implant device.

FIG. 21 is a perspective view of another embodiment of a gastrointestinal implant device 2200. The gastrointestinal implant device 2200 includes a sleeve 202 and an anchoring ring 2204. The distal end of the anchoring ring 2204 is bonded to the proximal end of the sleeve 202. A plurality of eyelets 2206 are distributed around the circumference of the proximal end of the ring for anchoring the device to the pyloric muscle using anchors shown in FIG. 24. The anchoring ring 2204 is made from a flexible material such as silicone allowing the ring 2204 to be collapsed for endoscopic insertion and removal.

The anchoring ring 2204 does not hold the pylorus open. However, in an alternate embodiment, the anchoring ring 2204 can be bonded to a stent with sufficient length and diameter to hold the pylorus open as described in conjunction with FIG. 2. The anchoring ring 2204 anchors the device and the stent holds the pylorus open.

Figure 22:
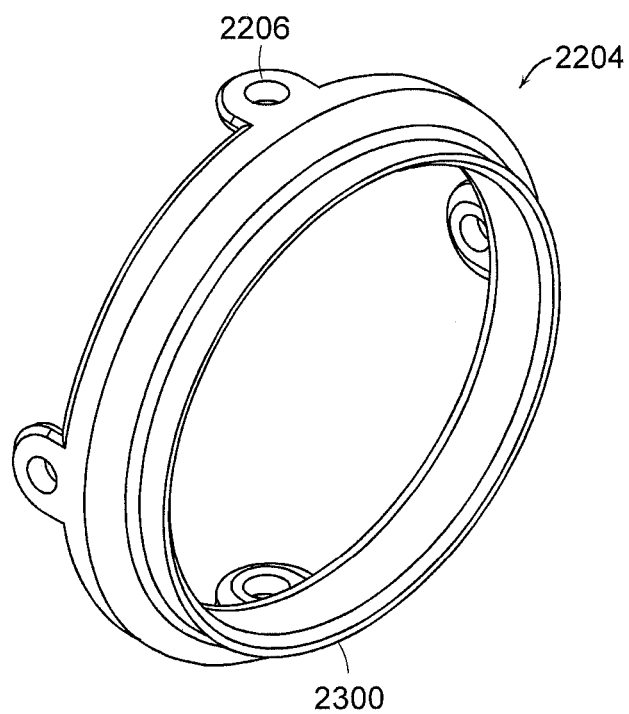
FIG. 22 is a perspective view of the anchoring ring shown in FIG. 21.

FIG. 22 is a perspective view of the anchoring ring 2204 shown in FIG. 21 in the expanded position. The sleeve is bonded to the outer surface 2300 of the proximal end of the anchoring ring whose diameter is 0.8" or about the same as the diameter of the sleeve. The anchoring ring 2204 includes at least four eyelets to anchor the device in place. The outer most diameter of the ring is about one inch. In an alternate embodiment there can be more than four eyelets.

Figure 23:
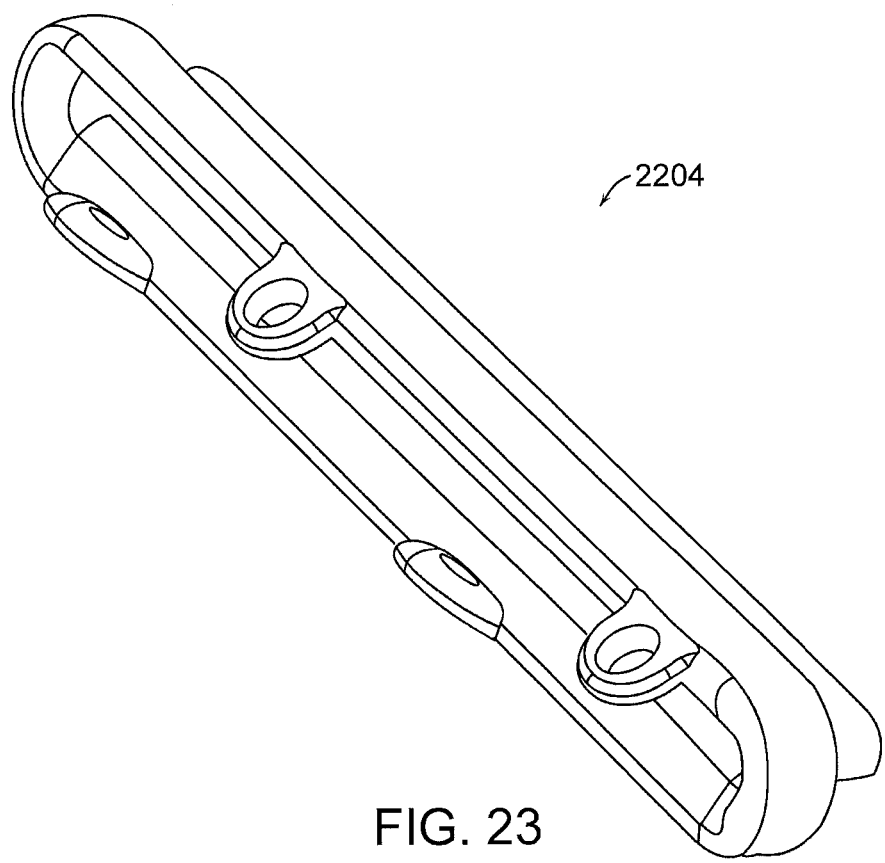
FIG. 23 is a perspective view of the anchoring ring shown in FIG. 21 in a collapsed position for insertion and removal.

FIG. 23 is a perspective view of the anchoring ring 2204 shown in FIG. 21 in a collapsed position for insertion and removal. The circular ring 2204 shown in FIG. 21 has been compressed to an oval shape allowing the anchoring ring to be inserted into the lumen of a catheter for delivery.

Figure 24:
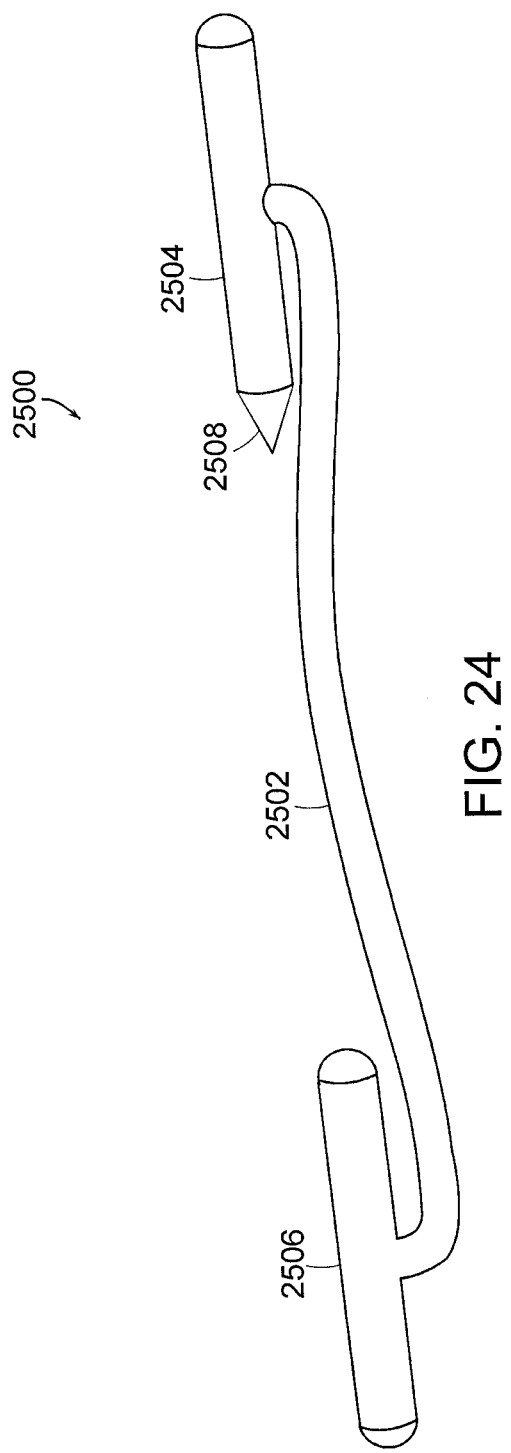
FIG. 24 is a perspective view of an anchor for anchoring the collapsible ring shown in FIG. 23 to the muscular tissue of the pyloric section of the stomach.

FIG. 24 is a perspective view of an anchor 2500 for anchoring the collapsible ring shown in FIG. 23 to the muscular tissue of the pyloric orifice. The anchor 2500 includes an anchor pin 2504 coupled to a second pin 2506 by a flexible shaft 2502. The anchor pin 2504 includes a shaped barb 2508 for locking the anchor 2500 into the tissue. The anchor 2500 is delivered after the collapsible ring has been positioned in the pyloric orifice. The anchor is guided so that the anchor pin 2504 is directed through a respective eyelet with the barbed portion of the anchor pin 2504 guided toward the tissue. After the barb 2508 has been locked into the tissue, the second pin 2506 sits inside the gastrointestinal implant device while the barbed portion 2508 of the anchor pin 2504 sits inside the pylorus muscle tissue. For removal of the gastrointestinal implant device from the body, the flexible shaft 2502 of the anchor 2500 is cut.

FIG. 25A is a perspective view of a delivery system 2600 for delivering the anchor 2500 after the gastrointestinal implant device has been placed in the pyloric orifice. The anchor 2500 is loaded in the distal end of a catheter having a single lumen tube 2600. The hollow, distal end of the delivery device is a sharp needle made to penetrate the pylorus muscle. In an alternate embodiment, the distal end of the delivery device can be formed in an arc to improve access to the eyelets through an endoscopic approach. The catheter 2600 includes a pusher 2604 for releasing the anchor 2500. The pusher 2504 is moved in a longitudinal direction 2602 to release the anchor 2500 from the lumen.

FIG. 25B is a plan view of the delivery system 2600 shown in FIG. 25A. FIG. 25C is a cross-sectional view of the distal end of the catheter 2600 as taken along line B-B of FIG. 25B. As described in conjunction with FIG. 24, the anchor 2500 includes pins 2504, 2506 coupled by a flexible shaft 2502. The anchor 2500 is loaded in the lumen at the distal end of the catheter 2600. The anchor pin 2504 is placed in the distal end of the tube 2600 and the second pin 2506 in the proximal end. The barb 2508 on the anchor pin 2504 is pointed toward the proximal end of the tube 2506 to engage with the tissue upon release in the muscle tissue. The catheter is advanced to the center of the ring positioned in the pyloric orifice. The sharp end 2510 is then pushed through an eyelet and into the muscle tissue. The pusher 2506 is pushed in longitudinal direction 2602 to release the distal anchor 2506. Once the distal anchor is released, the delivery system is pulled back, dragging the proximal part of the anchor out of the delivery device with the flexible shaft going through the eyelet, and the proximal anchor portion resting on the inside of the device. In the embodiment of the ring shown in FIG. 22, four anchors 2506 are delivered to anchor the gastrointestinal implant device through the four eyelets.

FIG. 25D is an isometric view illustrating the sharp end 2510 of the needle inserted through an eyelet 2206 for delivery of the anchor 2500 to the tissue 2512. The distal end of the catheter is formed in an arc 2520 to improve access the eyelets 2206. The sharp end 2510 of the catheter is inserted through the eyelet 2206 into the tissue 2516. The anchor pin 2504 of the anchor has been pushed out from the lumen into the tissue 2512.

Figure 25E:
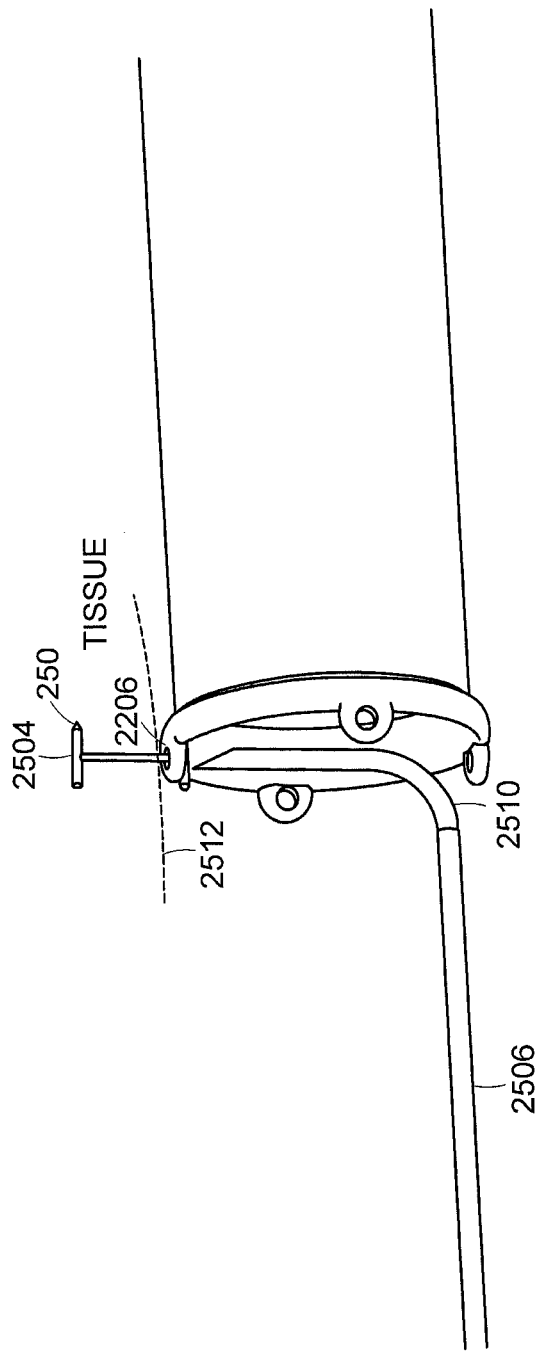
FIG. 25E is an isometric view illustrating the barb engaging the tissue after delivery.

FIG. 25E is an isometric view illustrating the barb 2508 engaging the tissue 2512 after delivery. The catheter has been removed from the eyelet 2206 leaving the anchor pin 2504 engaging the tissue 2516.

FIGS. 26A-E illustrate an alternative embodiment of a locking mechanism for holding the distal end of the sleeve 202 in position during delivery of the gastrointestinal implant device. The snare wire 2650 is passed through one of the lumens of the catheter to the distal end. At the distal end, the end of the snare wire 2650 is looped back and attached to or anchored inside the catheter. The folds of the sleeve 202 are advanced through this snare loop. The snare handle 2664 pulls and releases the snare wire 2656 to lock and release the distal end of the sleeve 202. The delivery system includes a pull tap 2666 for releasing a drawstring holding the stent in a collapsed position.

FIG. 26B is cross-sectional view taken along line C-C of FIG. 26A through the inner sheath 2650. The inner sheath has two lumens 2654, 2656 and has a diameter of about 0.078 inches. The first inner lumen 2564 is for passing a guidewire through the inner sheath and is about 0.04 inches in diameter. The second inner lumen 2656 is for passing the snare wire through the inner sheath is about 0.02 inches in diameter. The end of the snare wire 2658 is anchored inside the inner sheath.

FIG. 26C is a cross-sectional view taken along line DD of FIG. 26A through the outer sheath 2600 showing the inner sheath within the outer sheath. The outer sheath has an inner diameter of about 0.1 inches and an outer diameter of about 0.143 inches. The open space inside the outer sheath can be used for passing a drawstring through the outer sheath.

FIG. 26D is a cross-sectional view through the distal portion of the catheter showing the snare capturing the distal end of the sleeve. The distal end of the sleeve 202 is captured by the snare wire 2656 by pulling the distal end of the sleeve through a loop formed by the snare wire 2656.

FIG. 26E is a sectional view through the distal portion of the catheter showing the snare locking mechanism. The distal end of the sleeve is locked by pulling the snare wire 2656 in a longitudinal direction 2664 toward the proximal end of the delivery system to capture the sleeve folds against the inner shaft. After the gastrointestinal implant device is properly positioned in the body, the snare wire is advanced in a longitudinal direction 2662 toward the distal end of the delivery system. This opens the snare wire 2656 and releases the sleeve 202.

Figure 27:
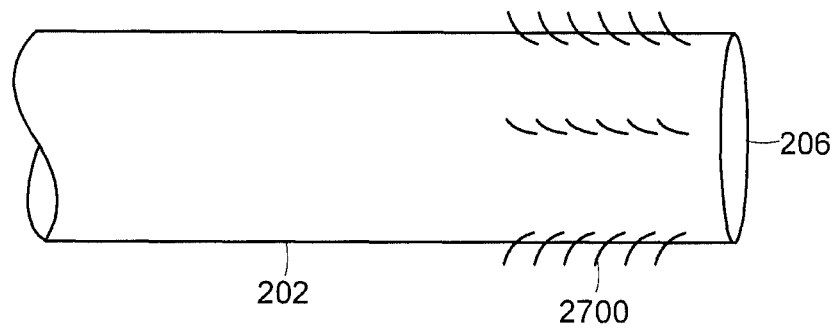
FIG. 27 is a perspective view of the distal portion of the gastrointestinal implant device including texturing at the distal end.

FIG. 27 is a perspective view of the distal portion of the gastrointestinal implant device including texturing 2700. Texturing of the distal end of the sleeve can be added to ensure that the actions of peristalsis do not advance the sleeve proximally, towards the stomach, but keep the sleeve pulled taught in the intestine. At the distal end of the sleeve, texturing 2700 is added with a directional aspect to it. The texturing 2700 can be molded into the sleeve material or added by adhesive or thermal bonding methods. The texturing material includes fibril shapes that are directed proximally so that any peristaltic waves that travel proximally will have less force on the sleeve than distal peristaltic waves.

The gastrointestinal implant device offers a new alternative where other means of weight loss and efforts at behavior modification have failed. Because the gastrointestinal implant device is endoscopically introduced, there is a reduced risk at insertion compared to surgery. The procedure is also completely reversible, making this approach the ideal solution for patients who are desperate to reverse behavioral patterns that have led to weight gain.

When inserted in the body, the gastrointestinal implant device mimics the duodenal bypass of the Roux-en-Y procedure. The implanted device reduces caloric absorption by delaying enzyme mixing with food and provides the feedback produced by the Roux-en-Y procedure by producing dumping syndrome when high sugar meals are ingested. Rapid stomach emptying is encouraged by inserting a stent in the pylorus to hold the pylorus open and all food bypasses the duodenum and passes rapidly into the jejunum. The implant device is an improvement on the Roux-en-Y procedure because it is minimally invasive and reversible. In the treatment of the super-obese where aggressive weight loss is not achieved, the length of the implant device below the stent can be further increased to drive the patient close to the point of malabsorption.

Placement of the gastrointestinal implant device effectively provides that ingested food does not digest in a normal manner and the gut hormones that are normally triggered are modified. These hormones result in several physiology changes that impact hunger and digestion. Gut hormones include peptide YY (PYY), cholecystokinin (CCK) and ghrelin.

As under digested food enters the ileum or distal part of the small intestine, a hormone called peptide YY or PYY is released. This hormone has been shown to have a direct effect on appetite, reducing it when released. Undigested food in the ileum indicates that too much food has been ingested. Thus, dependent on the length of the sleeve, the gastrointestinal device can promote deposition of undigested or partially digested food to the distal bowel. Therefore, the placement of a sleeve in the intestine promotes the delivery of undigested food to the ileum, which in turn promotes the release of PYY and reduces appetite in humans.

The hormone cholecystokinin (CCK) is released when food contacts the duodenum. CCK triggers the release of bile from the gallbladder. Therefore, placing a sleeve in the duodenum reduces the release of CCK and thus reduces bile output resulting in reduction in the digestion of food.

Some ghrelin is released when food contacts the duodenum. Ghrelin has been shown to be a factor in the control of appetite. This device will reduce ghrelin output and thereby reduce appetite due to the bypass of the duodenum.

Type 2 diabetes is a disease of obesity that occurs when patients cannot adequately use the insulin they produce. Usually, it is not that the patient cannot make enough insulin, but rather that the patient's body cannot effectively use the insulin produced. A particularly dangerous result of type 2 diabetes is that blood sugar spikes after a meal. This is called post-prandial hyperglycemia. This spike in blood glucose causes cardiovascular and microvascular damage. One class of drugs used to control post-prandial hyperglycemia is the alpha-glucosidase inhibitors. These work by reducing the breakdown and absorption of carbohydrates to sugars. The sleeve has a similar function because it reduces bile and delays the breakdown and absorption of the carbohydrates, which are normally readily absorbed in the duodenum, but are less likely to be absorbed in the jejunum and ileum. Therefore, type 2 diabetes can be controlled by placing a sleeve in the proximal intestine to delay the digestion of carbohydrates which reduces post-prandial hyperglycemia.

The gastrointestinal implant device can be used to reduce Type 2 diabetes symptoms by bypassing the duodenum. Following gastric bypass surgery, patients commonly experience complete reversal of Type 2 diabetes. While the exact mechanism of this remarkable effect is not understood, the clinical result is reported in a high percentage of cases. Reversal of Type 2 diabetes after gastric bypass is described in "Potential of Surgery for Curing Type 2 Diabetes Mellitus" by Rubino et al. incorporated herein by reference in its entirety. Since the gastrointestinal implant device provides equivalent blockage of duodenal processes, a similar effect is elicited but without the trauma of surgery. In patients who are not obese but suffer Type 2 diabetes, a modified gastrointestinal implant device is inserted. This gastrointestinal implant device provides the necessary effect to hinder pancreatic processes and receptors without blocking absorption.

In the embodiment of the gastrointestinal implant device for treating diabetes, the length of the stent may be selected to allow the pylorus to operate normally. The length of the sleeve may be reduced to mimic the duodenum bypass. The sleeve extends to just below the ligament of Treitz but does not extend further into the jejunum, thus allowing absorption to occur in the jejunum.

The gastrointestinal implant device can be placed temporarily in the stomach and duodenum to allow tissues to heal. For example, the sleeve can be placed temporarily to promote healing of ulcers in the stomach and duodenum. Ulcers are lesions that form in tissues of the stomach and duodenum. If they bleed, they are typically cauterized with electrosurgery. For ulcers to heal, they must be protected from the acidic environment. Placement of a sleeve for a short time period, for example, for one to two weeks, promotes healing of ulcers in the stomach and duodenum by eliminating the acidic environment and allows the tissues to heal.

Intestinal anastomoses are performed to remove sections of diseased bowel. The stapled or sewn connection is prone to leakage until it heals. The placement of the gastrointestinal implant device temporarily in the bowel can be used to promote healing of small bowel anastomoses by protecting the area from chyme and minimizing leaks.

The gastrointestinal implant device can be used to deliver drugs, hormones and other active agents directly to the intestine. To deliver the agents, the sleeve is either coated or impregnated with the agents.

The two most common intestinal bowel diseases are Crohn's disease and ulcerative colitis. Crohn's disease may occur in any part of the digestive tract. Although the exact cause of the disease is unknown, it appears to be an abnormal immune response in the patient, which leads to chronic inflammation of the intestinal lining.

Crohn's disease is treated with drugs intended to reduce inflammation. These include aminosalicylates, corticosteroids, immune modifiers such as azathioprine and methotrexate and antibiotics including ampicillin and cipro. These drugs have negative effects when given systemically. Since the drug is really only needed locally, smaller amounts of drug can be used if delivered directly to the tissues.

The intestinal sleeve is coated with polymers that are impregnated with these drugs. Coatings may include polyurethanes, silicones and hydrophilic polymers like Hydromer. These coatings may be applied to the sleeve material by dipping or spraying techniques. If a porous sleeve material such as ePTFE is used, the drug filled polymer may be driven into the pores using internal pressure inside the sleeve. This increases the amount of drug that is available.

The sleeve material can also be a polymer that permits the incorporation of the drug directly into the wall. Such polymers include Ethylene Vinyl Acetate (EVA) and polyurethane. A greater amount of the drug may be incorporated in this case compared to a coating since there is more material in the wall than simply in coatings, thereby providing longer release times. The drug is compounded into the polymer and then extruded as is normally done to form the tubing or sheet from which the sleeve is made.

The sleeve is deployed transesophageally into the duodenum and proximal jejunum. When the sleeve comes in contact with the tissues, the drugs in the coating are released directly into the tissues. Also, the sleeve may act to block the contact of the food to the mucosa, thereby reducing irritation caused by the chyme. Once the drug has fully eluted from the material, the sleeve is removed and a new one is placed.

The control of appetite in the human is a complex function of hormonal interactions. Several hormones have been implicated in its control including Ghrelin, PeptideYY, Leptin, Glucagon-Like Peptide-1 (GLP-1), Cholecystokinin (CCK), insulin and others. These hormones are either released or suppressed by the presence of food in the duodenum. For example, PYY acts as an anti-hunger hormone as injections of PYY have been shown to decrease food intake in both rats and humans and decreases in leptin have been shown to stimulate hunger.

Sleeves that are located in the duodenum where many of these hormones are released may be impregnated with these hormones. When implanted, the hormones elute from the sleeve into the surrounding tissue where they activate the various satiety mechanisms.

Figure 28:
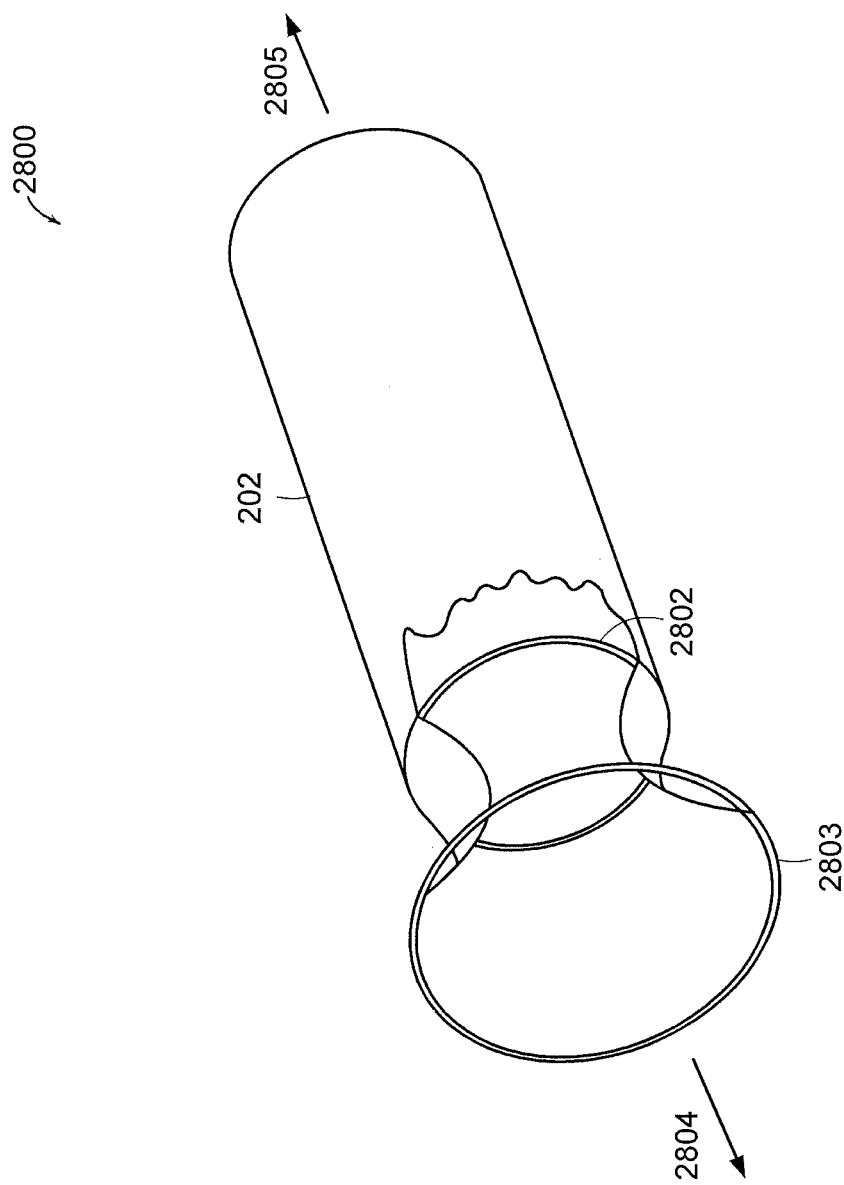
FIG. 28 is a perspective view of a gastrointestinal implant device with another embodiment of an anchoring device.

FIG. 28 is a perspective view of a gastrointestinal implant device with another embodiment of a collapsible self-expanding anchoring device. The gastrointestinal implant device 2800 includes a sleeve 202 and an anchoring device for anchoring the gastrointestinal implant device in the pylorus. The anchoring device includes two rings 2803, 2802 of differing diameters. A portion 2806 has been cut off to show the rings 2803, 2802. The rings are made from a metal such as heat treated spring steel. In one embodiment the rings are made from Nitinol.

The rings are spaced apart and are covered by the sleeve 202. The distal end of the proximal ring 2803 is bonded to the proximal end of the sleeve 202. The distal ring 2802 is also bonded to the sleeve distal to the proximal ring. The rings are spaced apart such that when the gastrointestinal device is positioned in the body, the proximal ring is located in the stomach and the distal ring is located in the duodenum.

The proximal ring 2803 serves to prevent the device from moving in the distal direction 2805 into the duodenum. The distal ring 2802 serves to resist motion in the proximal direction 2804. The diameter of each of the rings is variable with the diameter of the proximal ring greater than the diameter of the distal ring. In one embodiment, the diameter of the proximal ring 2803 is about 1.4" (35.6 mm) and the diameter of the distal ring 2802 is about 1.0" (25.4 mm). The diameters of the rings are dependent on the anatomy. The diameter of the proximal ring 2803 is selected to be greater than the pyloric orifice which is typically about 1" in diameter to prevent the ring from being pulled through the pyloric orifice to the intestines. The diameter of the distal ring 2802 is selected so that the ring is less than the diameter of the duodenum. The distance between the rings is dependent on the length of the pyloric orifice. This distance is selected so that when the proximal ring 2803 is positioned in the stomach, the distal ring 2802 is positioned at the distal end of the pyloric orifice in the duodenum. The distance between the rings also determines whether the pylorus is held open. If the distance between the rings is equal to the length of the pylorus, the pylorus is held open. If the distance between the rings is greater than the length of the pylorus, the sleeve material between the rings is loose allowing the pylorus to operate normally.

Figure 29:
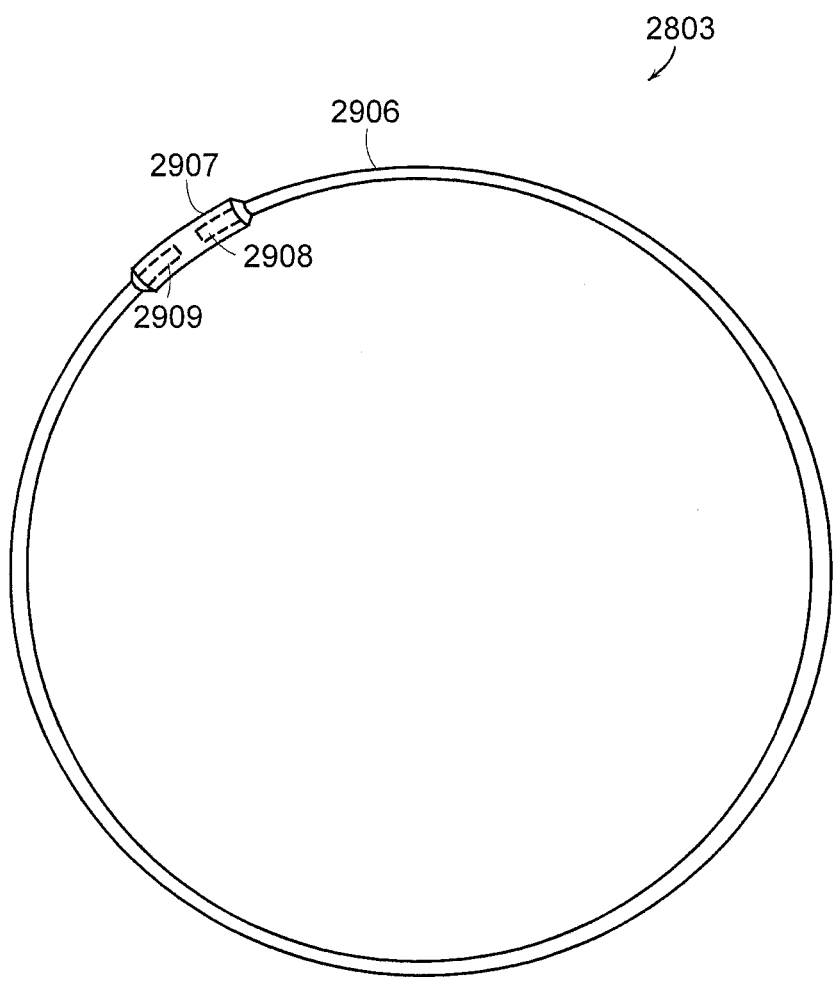
FIG. 29 is a plan view of one of the rings in the gastrointestinal implant device shown in FIG. 28.

FIG. 29 is a plan view of one of the rings 2803 in the gastrointestinal implant device shown in FIG. 28. The ring 2803 includes a wire 2906 and a crimp connector 2907. The ends of the wire 2908, 2909 are connected through the crimp connector 2907 to form the ring 2803. The anchoring device can be collapsed into a sheath to enable endoscopic delivery.

The wire is made from a Nitinol material and is heat treated to provide a super elastic state at a range of temperatures from room temperature through body temperature. The wire 2906 is about 0.020"-0.027" in diameter. The diameter of the wire is selected to provide sufficient radial stiffness to resist collapse by forces in the body, but to permit collapse into a delivery device.

Figure 30:
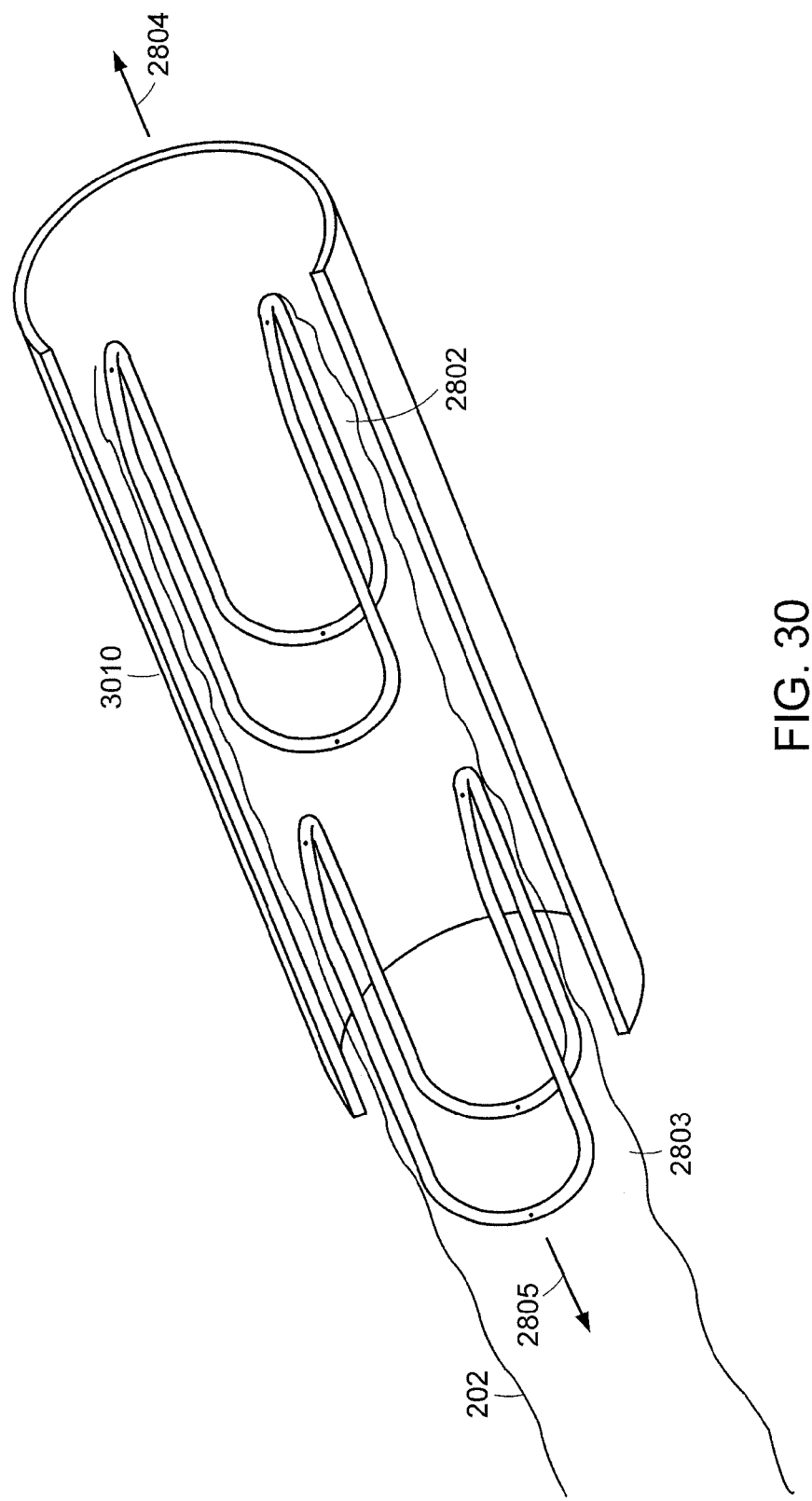
FIG. 30 is a perspective view of the gastrointestinal implant device shown in Fig. in a collapsed position in a delivery tube for delivery into the body.

FIG. 30 is a perspective view of the anchoring device in the gastrointestinal implant device shown in FIG. 28 in a collapsed position in a delivery tube 3010 for delivery into the body. The anchoring device is delivered to the stomach by folding each of the rings 2803, 2802 in a double U shape to reduce their diameter and length, so that the rings fit inside the delivery tube 3010 for endoscopic delivery and to permit deployment of the rings in a serial manner.

The delivery tube 3010 has a diameter of about 0.394"-0.591" (10-15 mm) and is about 2 inches in length. The rings 2803, 2804 are folded such that they fit inside the delivery tube 3010 and do not exceed the elastic limit of Nitinol. The folding into a double U shape also permits the rings 2802, 2803 to be pushed out of the delivery tube 3010 in distal direction 2805 in an orderly manner for delivery into the body. After delivery of the gastrointestinal device, the delivery tube 3010 is removed from the body through the stomach in proximal direction 2804.

Figure 31:
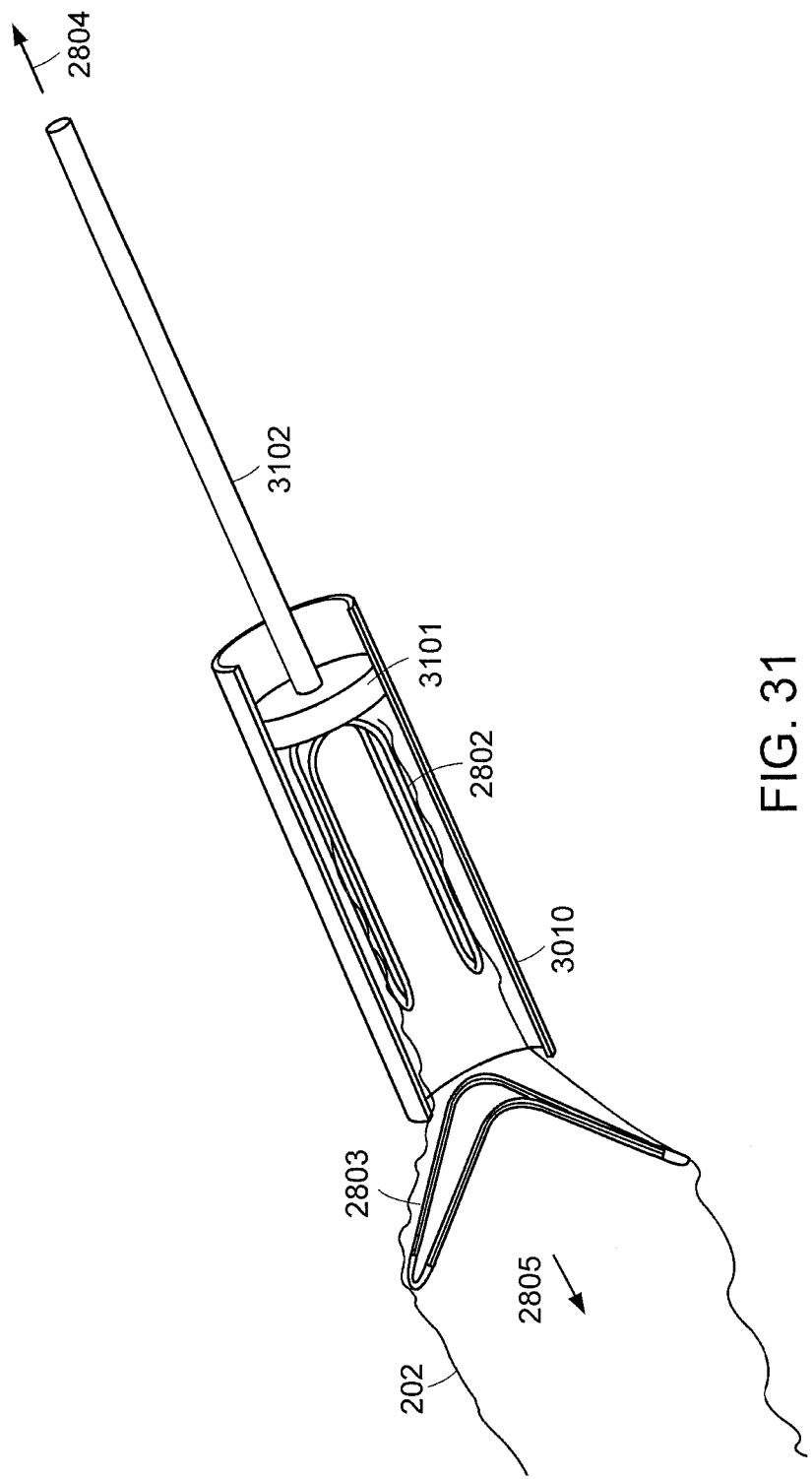
FIG. 31 is a perspective view of the gastrointestinal implant device illustrating the deployment of the distal ring from the delivery tube shown in FIG. 30.

FIG. 31 is a perspective view of the gastrointestinal device illustrating the deployment of the distal ring from the delivery tube 3010 shown in FIG. 30. As described in conjunction with FIG. 30, the rings 2803, 2302 are folded in a double U shape and are loaded into delivery tube 3010. A piston 3101 and proximal shaft 3102 are moveable with respect to delivery tube 3010 such that as the delivery tube 3010 is pulled in proximal direction 2804, or the shaft 3102 is pushed in distal direction 2805, the distal ring 2803 is first deployed in the duodenum, and then the proximal ring 2802 is deployed proximal in the stomach.

Figure 32:
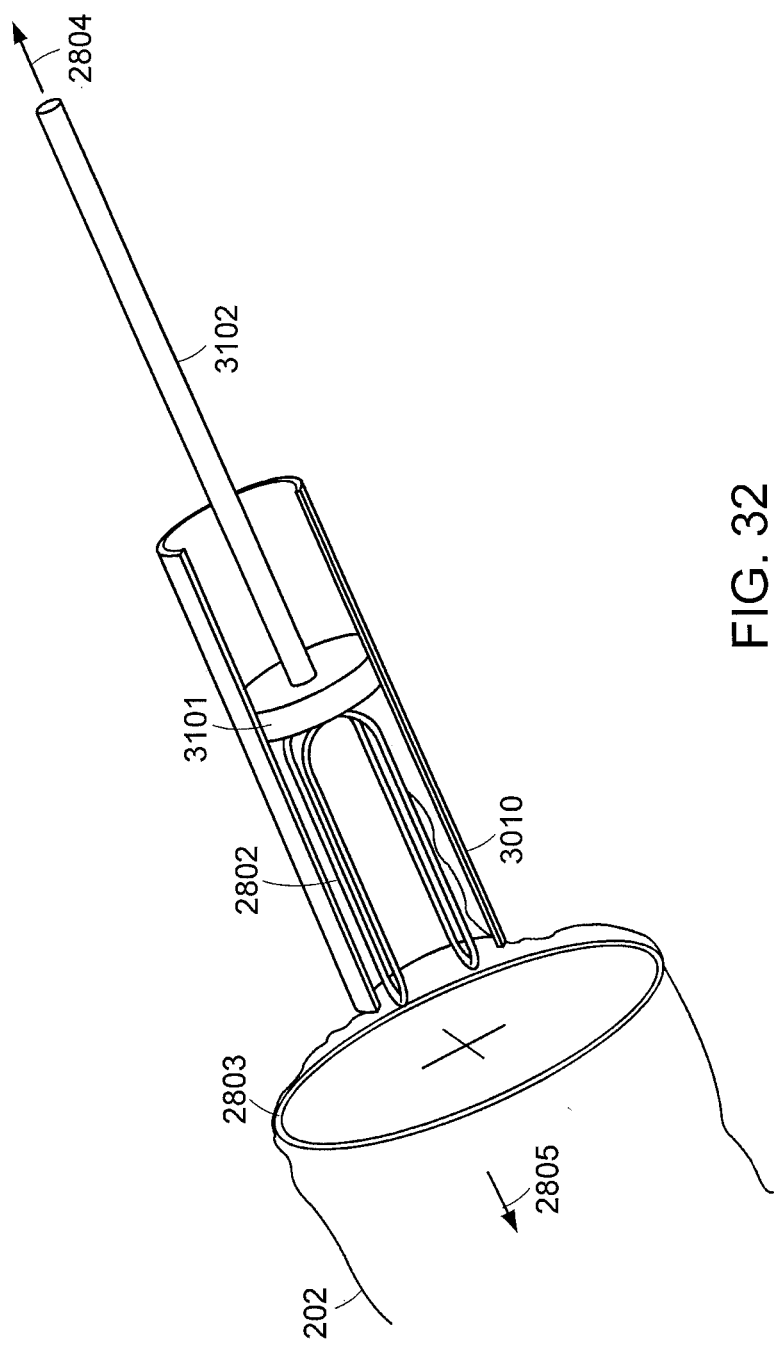
FIG. 32 is a perspective view of the gastrointestinal implant device after the deployment of the distal ring prior to deployment of the proximal ring.

FIG. 32 is a perspective view of the gastrointestinal device after the deployment of the distal ring 2803 prior to deployment of the proximal ring 2802. After deployment, the distal ring 2803 expands under its own elastic force and is positioned in the duodenum. The portion of the sleeve 202 between the rings is then pulled in proximal direction 2804. As the second proximal ring 2802 is released, it is positioned in the stomach.

Figure 33:
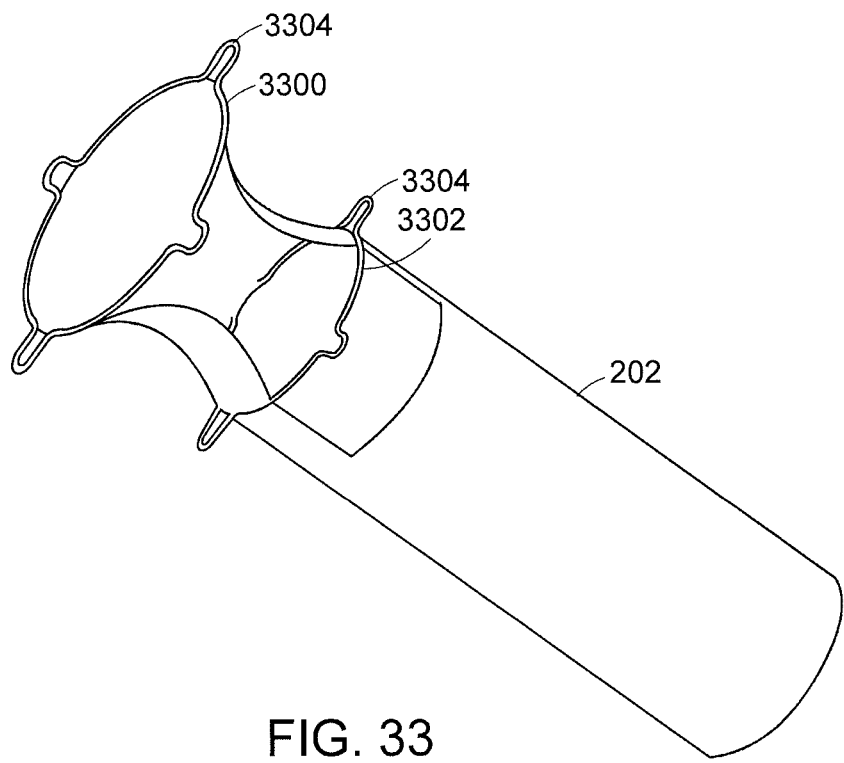
FIG. 33 is a perspective view of the gastrointestinal implant device shown in FIG. 28 with an alternative embodiment of an anchoring device.

FIG. 33 is a perspective view of the gastrointestinal implant device shown in FIG. 28 with an alternative embodiment of an anchoring device. The anchoring device includes two nitinol rings 3300, 3302 of differing diameters where the rings are shaped with stabilizing ears 3304 to prevent the rings from twisting.

Each of the rings 3300, 3302 is fabricated from nitinol wire as previously described. Each ring contains loops (stabilizing ears) 3304 that protrude beyond the diameter of the ring. These loops 3304 serve to provide additional anchoring into the tissues and especially to limit rotation of the rings in place. The addition of the loops to each ring permits reduction of the wire diameter and/or the ring diameter while maintaining similar anchoring ability. This also reduces trauma to the anchoring tissues. The number of loops 3304 is variable. There can be two, three or four loops. In the embodiment shown, each ring has four loops. As the gastrointestinal device is a removable, tissue in-growth into the anchoring device is not desired. Therefore, each loop 3304 is coated with a polymer such as polyurethane in a dipping process to fully cover the openings.

Figure 34:
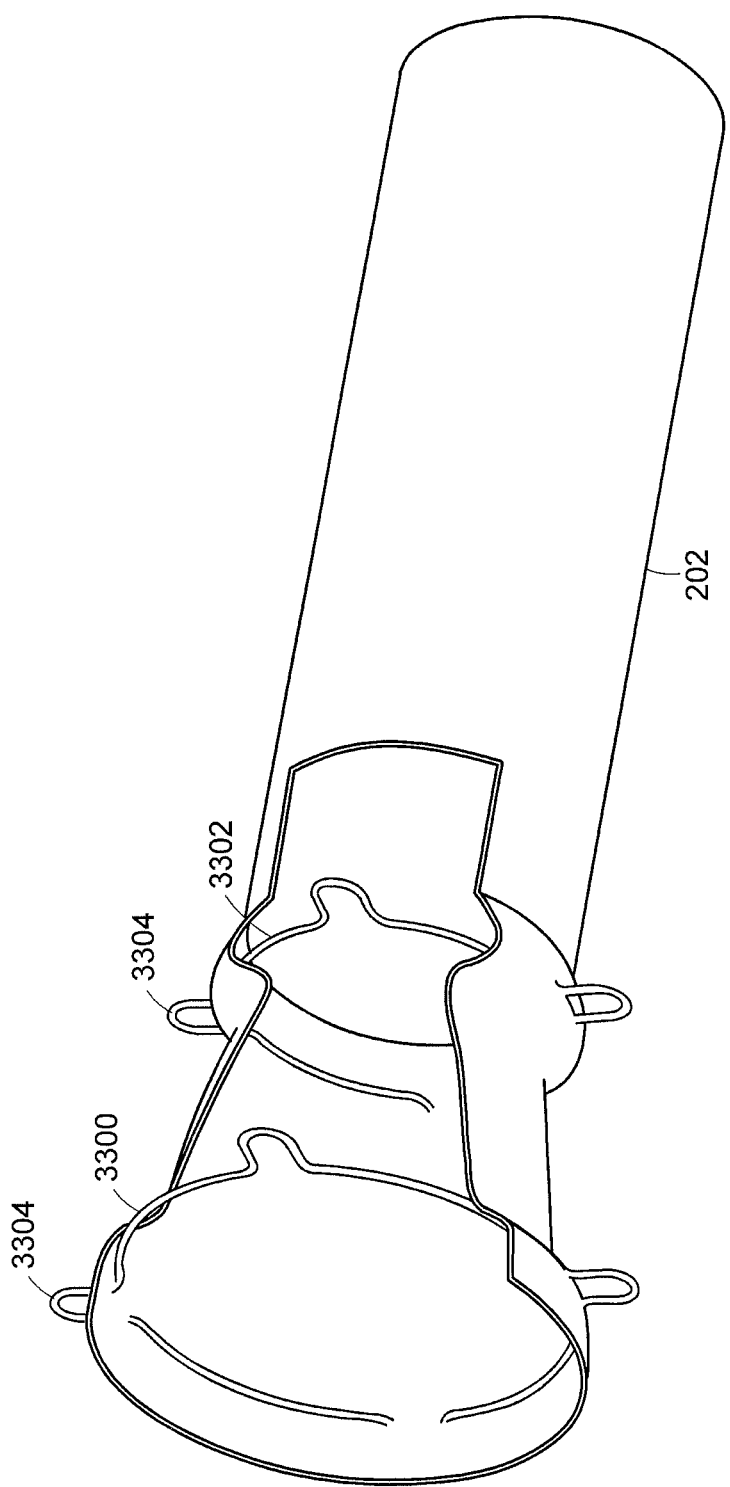
FIG. 34 is a plan view of the gastrointestinal implant device shown in FIG. 33.

FIG. 34 is a plan view of the gastrointestinal implant device shown in FIG. 33. The loops on each of the rings protrude through the exterior surface of the sleeve to push against the tissue to anchor the gastrointestinal implant device in the pyloric region of the stomach. The non-loop portions of each of the rings are encapsulated by the sleeve.

Figure 35:
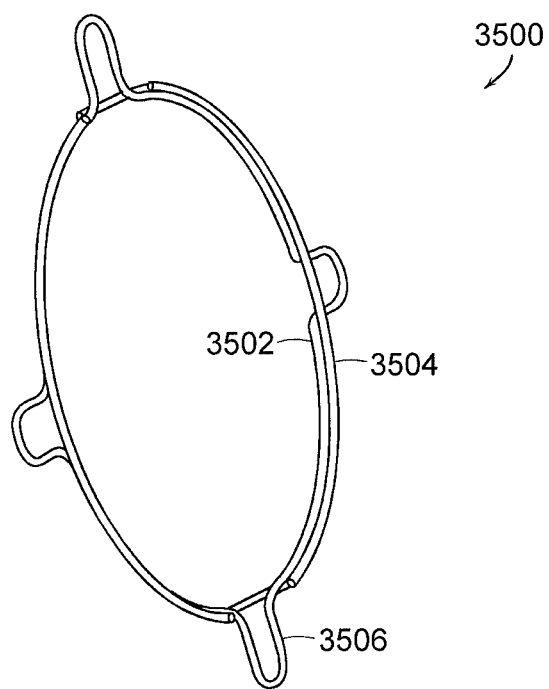
FIG. 35 is a perspective view of another embodiment of one of the anchoring rings shown in FIG. 28.

FIG. 35 is a perspective view of another embodiment of one of the anchoring rings shown in FIG. 28. In the embodiment shown, a ring 3500 is formed from multiple wires. In this case, two wire loops 3502, 3504 are loosely intertwined to form a single anchoring ring 3500. By forming the ring from multiple wires, the diameter of the wire can be reduced. Therefore, the rings can be folded into a smaller delivery device and still maintain the same the radial force on the tissue as the single wire embodiment to hold the ring in place when deployed. Additional wires can be used to further reduce the diameter of the wires. Wire 3502 contains loops 3506 that protrude beyond the diameter of the ring 3500 to provide additional anchoring into the tissues.

Figure 36:
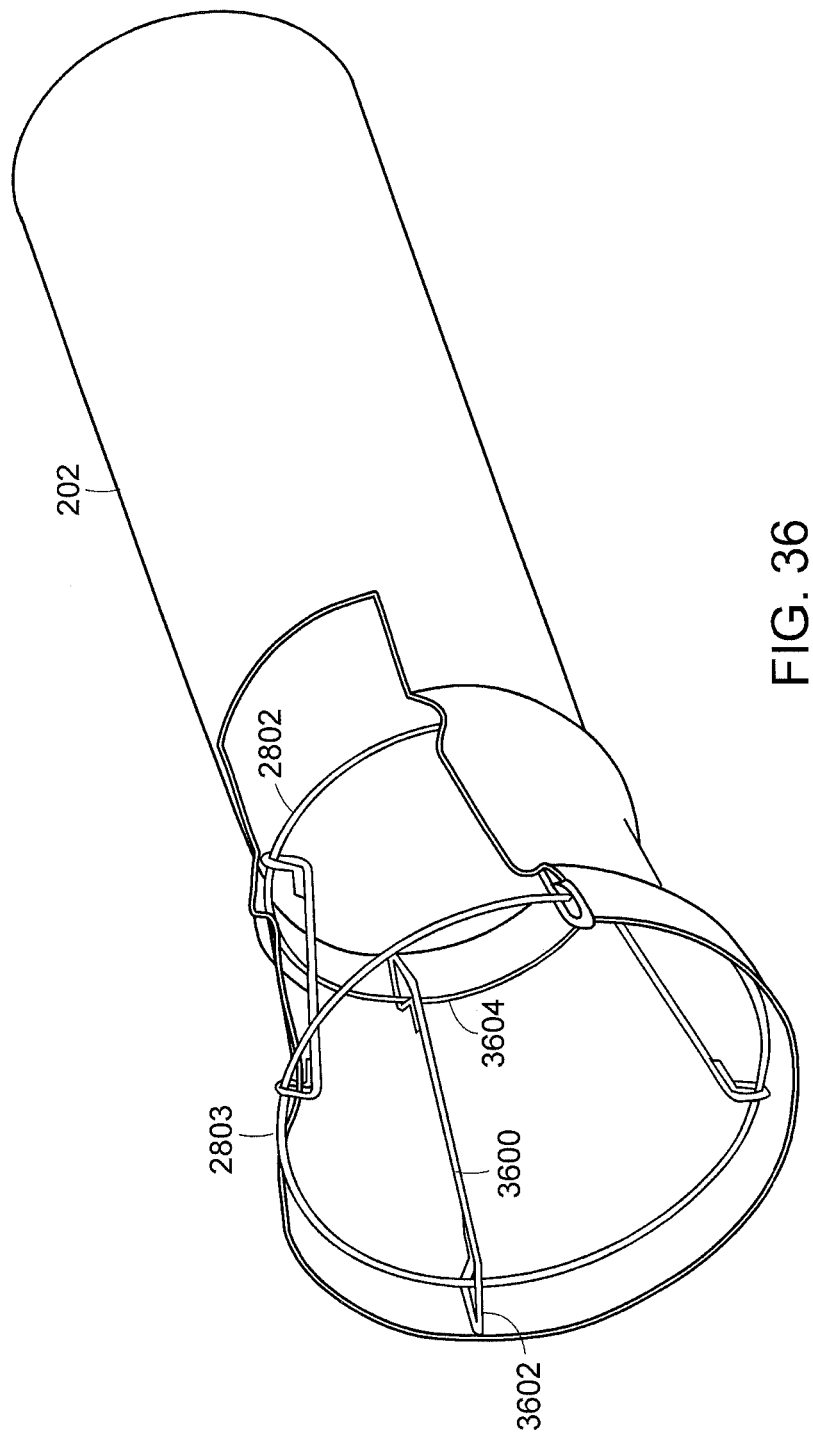
FIG. 36 is a perspective view of a gastrointestinal implant device with yet another embodiment of an anchor.

FIG. 36 is a perspective view of a gastrointestinal implant device with yet another embodiment of an anchor. The device includes two nitinol rings of differing diameters that are linked together with connecting rods 3600 to stabilize the rings 2803, 2802. The connecting rods 3660 stabilize the anchor by limiting motion of the rings.

The anchor is formed by proximal ring 2803 and distal ring 2802 loosely connected by at least one connecting bar 3600. There are loops 3602, 3604 at the end of each connecting bar 3600, each loop 3602, 3604 engages a respective one of the rings 2803 and 2802. The sleeve 202 encapsulates the entire assembly.

Figure 37:
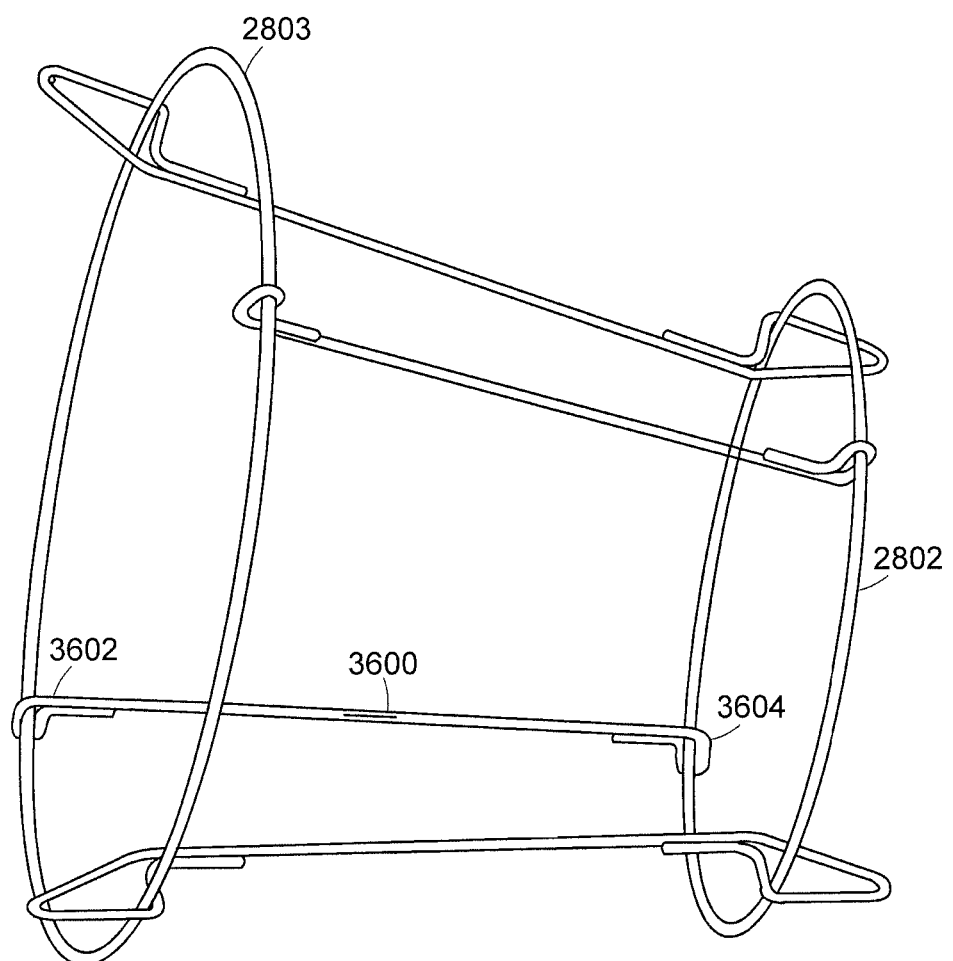
FIG. 37 is a perspective view of the anchor shown in FIG. 36 with the sleeve removed.

FIG. 37 is a perspective view of the anchor shown in FIG. 36 with the sleeve 202 removed. There are four interconnecting bars 3600 spaced apart from each other around the diameter of the rings 2803, 2802. The interconnecting bars 3600 serve multiple functions. First, when the anchor is in position in the body with the proximal ring 2803 in the stomach and the distal ring 2802 in the duodenum, the interconnecting bars 3600 serve to stent open the pylorus. Second, the interconnecting bars 3600 serve to stabilize each of the rings 2803, 2802 and limit the twisting or translational motion of the rings with respect to each other.

Figure 38:
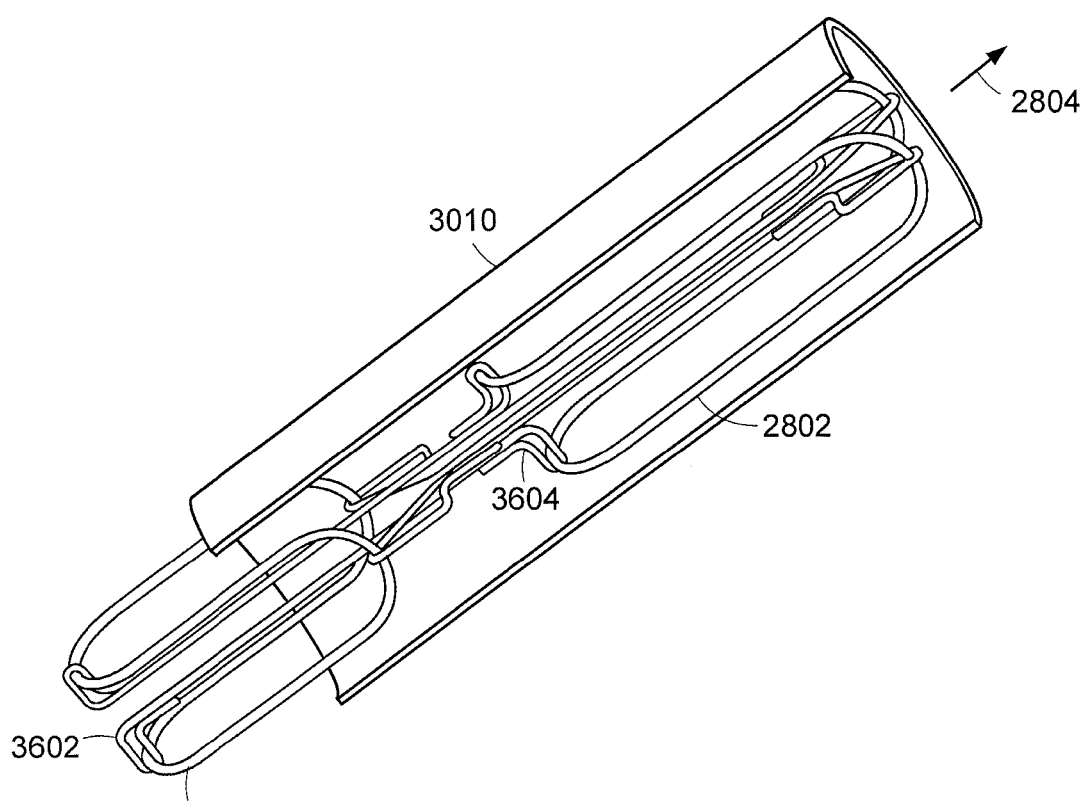
FIG. 38 is a perspective view of the gastrointestinal device shown in FIG. 36 in a collapsed position in a delivery tube for delivery into the body.

FIG. 38 is a perspective view of the anchor shown in FIG. 37 in a collapsed position in a delivery tube 3010 for delivery into the body. The rings 2803, 2804 connected by connecting bars 3600 are folded in a double U shape and placed inside the delivery tube 3010. As described in conjunction with FIG. 30, after delivery of the gastrointestinal device, the delivery tube 3010 is removed from the body through the stomach in proximal direction 2804.

Figure 39:
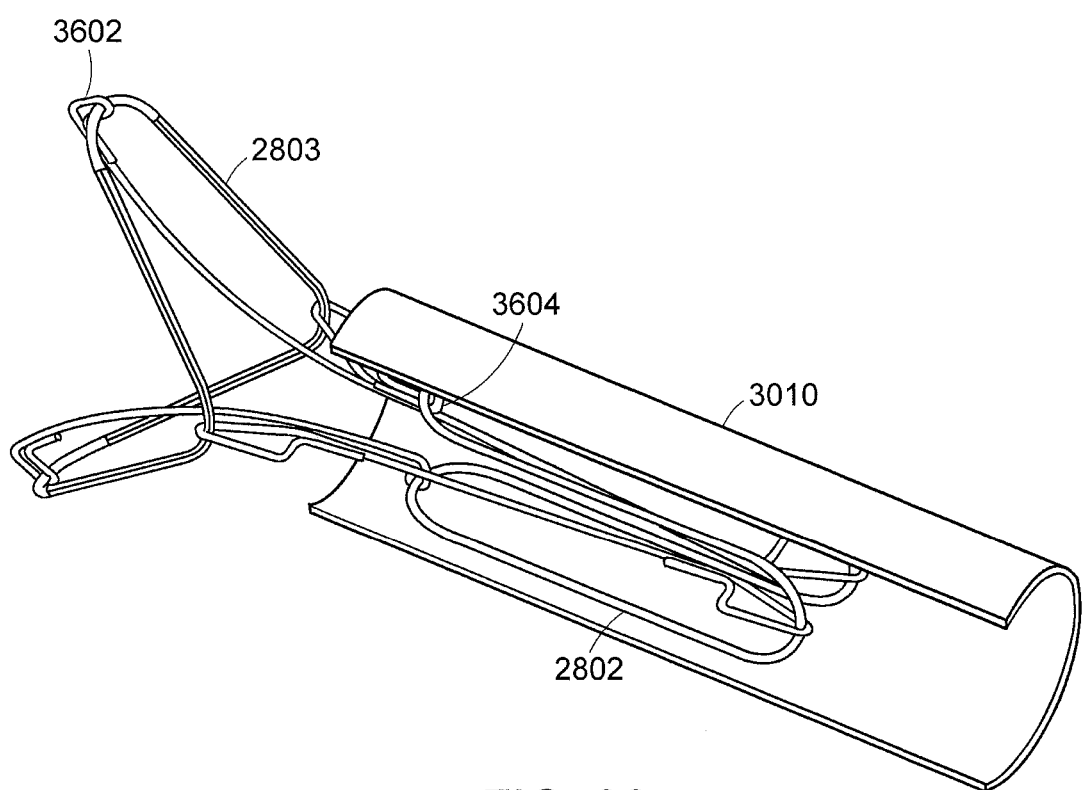
FIG. 39 is a perspective view of a delivery system illustrating the deployment of the distal ring 2803 from the delivery tube.

FIG. 39 is a perspective view of the anchor shown in FIG. 37 illustrating the deployment of the distal ring 2803 from the delivery tube 3010 shown in FIG. 38. As described in conjunction with FIG. 31, the distal ring 2803 is first deployed distal to the pylorus in the duodenum, and then the proximal ring 2802 is deployed proximal to the pylorus in the stomach.

Figure 40A:
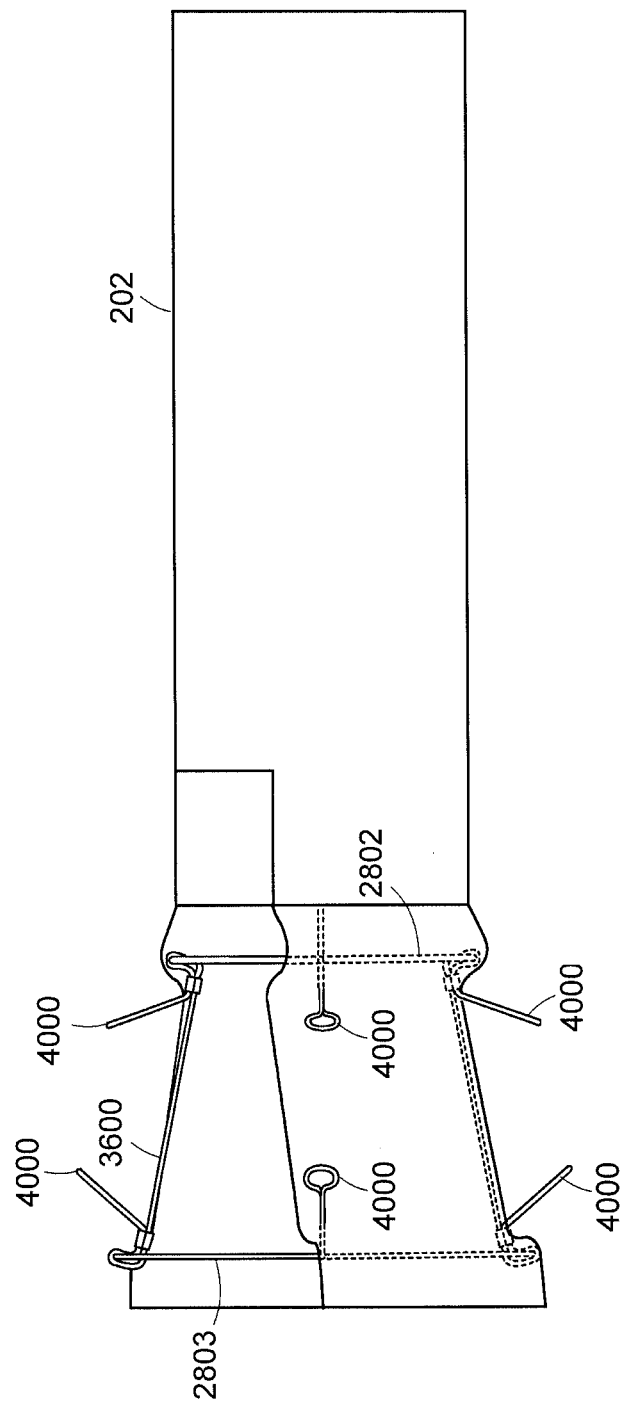
FIG. 40A is a plan view of the gastrointestinal device shown in FIG. 38 with additional anti-rotation and locking features.

FIG. 40A is a plan view of the gastrointestinal device shown in FIG. 38 with additional anti-rotation and locking features. The connecting rods 3600 are further formed with loop extensions 4000. The loop extensions 4000 on each connecting rod 3600 are angled towards each other. These loop extensions 4000 press against the muscle of the pylorus to anchor the gastrointestinal implant device in the pylorus portion of the stomach and serve to prevent any linear motion of the device. Rotation of the device is also reduced. The loop extensions 4000 are coated with polyurethane to prevent tissue in growth.

Figure 40B:
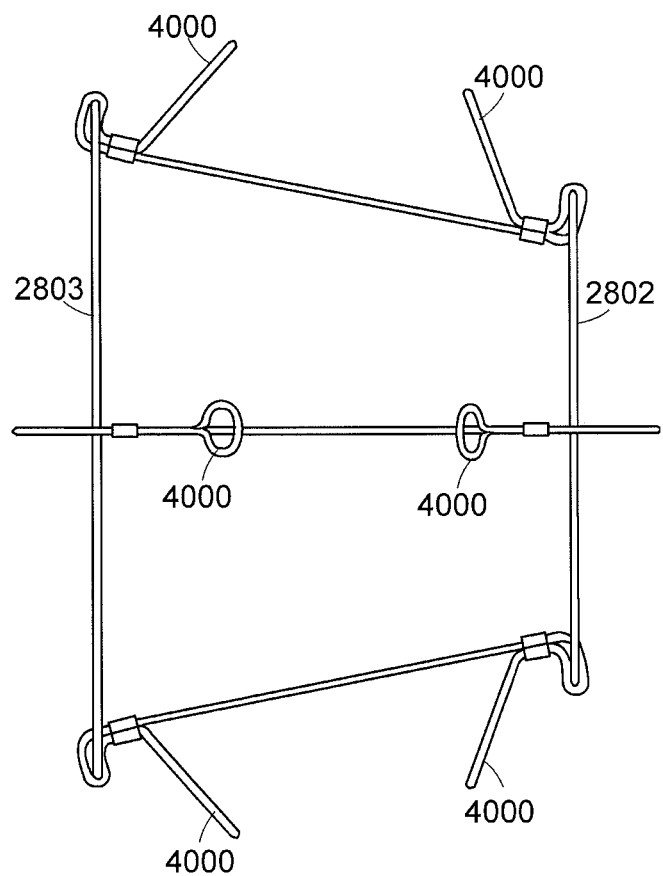
FIG. 40B is a perspective view of the anchor shown in FIG. 40A without the sleeve.

FIG. 40B is a perspective view of the anchor shown in FIG. 40A without the sleeve. The loop extensions 4000 on a connecting bar 3600 are angled towards each other to prevent linear motion. The loop extensions on the proximal end of the connecting bar 3600 are angled in a distal direction and the loop extensions on the distal end of the connecting bar are angled in a proximal direction.

Figure 41:
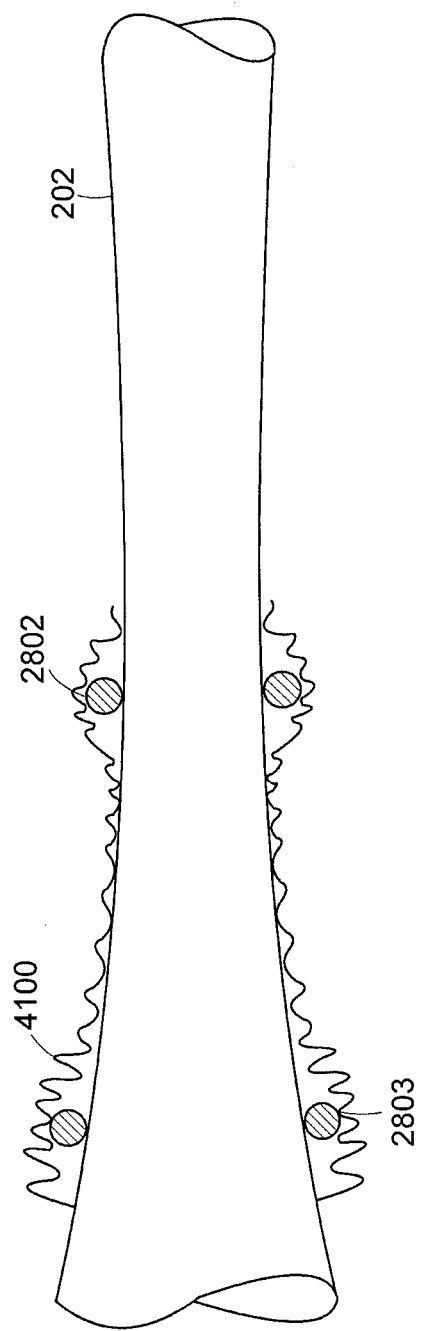
FIG. 41 is a perspective view of an alternative embodiment of a gastrointestinal implant device shown in FIG. 28.

FIG. 41 is a plan view of an alternative embodiment of a gastrointestinal implant device shown in FIG. 28. The gastrointestinal device includes two nitinol rings 2802, 2803 of differing diameters as described in conjunction with the embodiment described in conjunction with FIG. 28. The gastrointestinal implant device has sleeve material 202 on the inside and the sleeve material and rings are coated with a polymer such as polyurethane 4100 on the outside.

Figure 42:
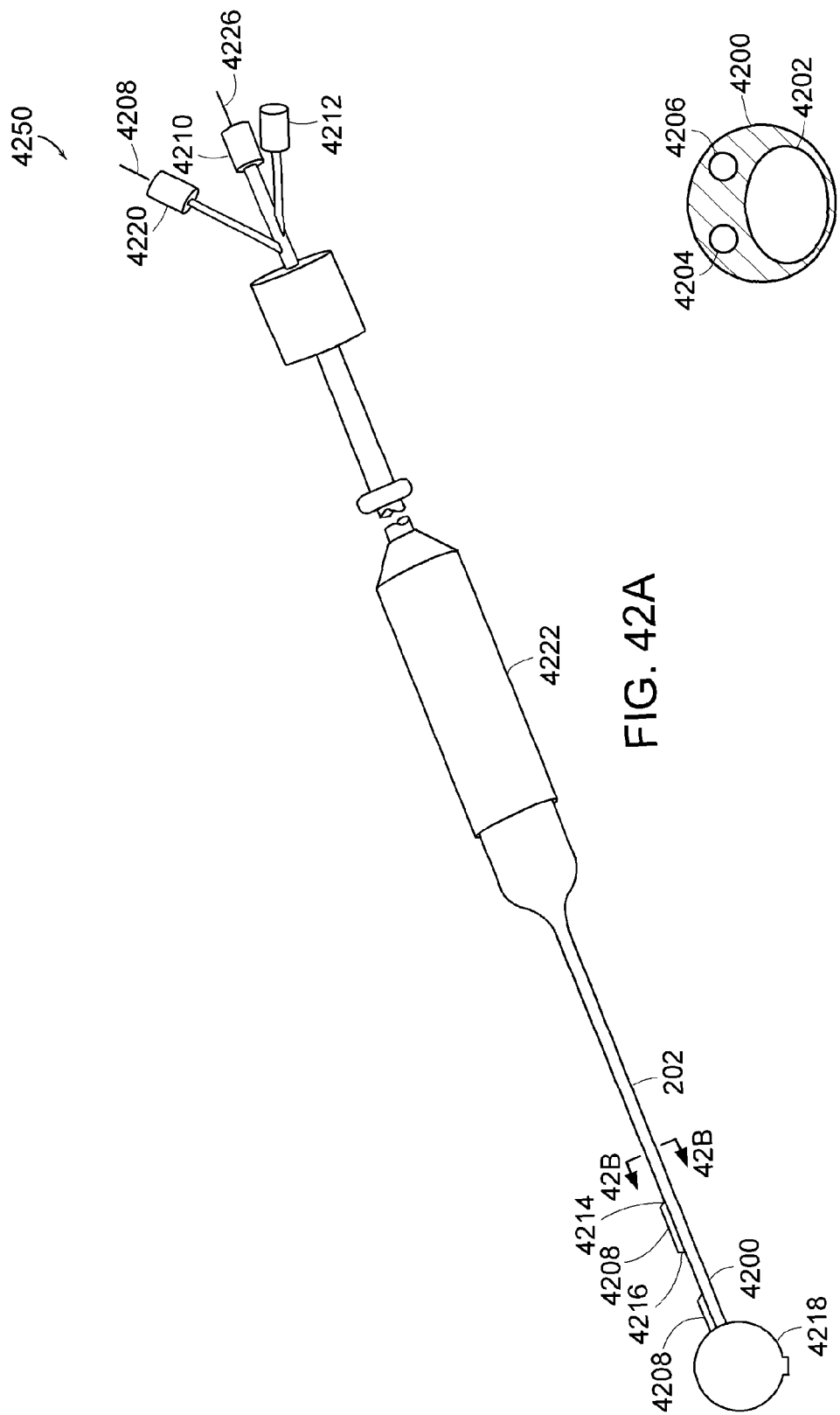
FIG. 42A is a perspective view of a portion of a catheter system for delivery of a gastrointestinal implant device.
FIG. 42B is a cross-sectional view of the catheter shaft taken along line 42B-42B of FIG. 42A.

FIG. 42A is a perspective view of a portion of a low profile catheter system 4250 for delivery of a gastrointestinal implant device. The low profile catheter has a detachable generally spherical shaped element 4218 coupled to the distal end of an inner shaft 4200 to aid the delivery of the catheter through the alimentary canal to the intestines. After the gastrointestinal implant device has been delivered, the spherical shaped element (ball) 4218 is detached and the zero profile catheter is removed through the gastrointestinal implant device. The normal peristalsis of the bowel is used to move the released ball through the intestines.

The catheter system 4250 includes an outer sheath 4222 for storing the collapsible anchor portion of the gastrointestinal implant device in collapsed form. Collapsible anchoring devices have already been described in conjunction with FIGS. 7, 23 and 30. The sleeve 202 is secured temporarily outside an inner sheath 4200 allowing for proper positioning of the gastrointestinal implant device and then for release.

FIG. 42B is a cross-sectional view of the inner shaft 4200 of the catheter system as taken along line 42B-42B of FIG. 42A. In one embodiment, the inner shaft 4200 is a three-lumen extrusion of Pebax 7233 with an outer diameter of 0.080" and round inner lumens 4202, 4204, 4206 having respective diameters of 0.040", 0.020" and 0.020". This material is selected to maintain a low profile, a small minimum bend radius; that is less than 0.5" without kinking, good column strength when fortified with an inner guide wire stylet, and a low coefficient of friction in a material with good thermoplastic and bonding properties.

A first lumen 4202 is used to pass a guide wire or mandrel 4226 through the catheter shaft to increase the rigidity of the catheter shaft during introduction of the catheter into the intestines. The first lumen 4202 is also used to inject fluid to lift the sleeve material 202 away from the inner shaft 4200 after the gastrointestinal device has been delivered to the intestine. A second lumen 4204 is used to pass a sleeve retention wire 4208 to the distal end of the gastrointestinal implant device. The sleeve retention wire is used to hold the distal end of the sleeve 202 to the outside of the inner shaft 4200. A third lumen 4206 is used to inject fluid at the tip of the catheter to lift the distal end of the sleeve 202 off the inner shaft 4200 prior to removal of the catheter system 4250 from the body.

Returning to FIG. 42A, the guide wire 4226 is passed through fitting 4210 connected to the first lumen 4202. The sleeve 202 is located concentrically over the catheter inner shaft 4200. It is held at its distal end to the inner shaft 4200 with the sleeve retention wire 4208. The sleeve retention wire 4208 holds the sleeve 202 in place during delivery.

Proximal fitting 4220 is connected to the second lumen and proximal fitting 4212 is connected to the third lumen 4206. During delivery of the gastrointestinal implant device, the first lumen 4202 is filled with a 0.035" Teflon coated guide wire 4226 that provides column strength for the appropriate amount of pushability without compromising the flexibility of the catheter inner shaft 4200. A 0.015" diameter Teflon-coated steel wire is placed in the second lumen 4204 to serve as the distal sleeve retention wire. The second lumen 4204 has 2 skive holes 4214, 4216 near the distal end of the catheter shaft 4200. The distal sleeve retention wire 4208 exits the second lumen 4204 through a proximal skive hole 4214 feeds through the sleeve material 202, which is wrapped tightly around the distal outer diameter of the catheter shaft, and re-enters the second lumen 4204 through a distal skive hole 4216. This creates a dead bolt style lock holding the sleeve 202 to the shaft 4200 until ready to be released similar to the dead bolt style lock described in conjunction with the two lumen catheter shaft shown in FIGS. 14A and 14B.

The distal end of the shaft terminates with a spherical shaped element 4218 that is either solid, or inflatable to form an atraumatic tip. In the embodiment shown, the spherical shaped element is a solid ball, similar to the ball described in conjunction with FIG. 17. In the embodiment shown, the diameter of the ball is about 0.5" (12.7 mm), however the range of diameters is about 0.25" (6.4 mm) to about 0.75" (19.2 mm). An embodiment of an inflatable spherical shaped element is described later in conjunction with FIGS. 50A-50B. The ball 4218 at the end of the catheter shaft is held onto the shaft 4200 with the sleeve retention wire 4208 maintaining tension on the ball 4302 which will be described later in conjunction with FIG. 46.

The collapsed anchor assembly is located in outer sheath 4222. The ball 4218 at the end of the catheter is released to withdraw the catheter. The release mechanism pulls the sleeve retention wire to release the ball end and release the end of the sleeve. The anchor assembly is then released from the outer sheath as previously described The catheter can be used any time access to the intestinal tract is desired. For example, the catheter can be used to pass an endoscope into the intestine. This catheter device can be used to rapidly run the intestines, place a guide wire and then use the placed guide wire as a track for an endoscope.

Figure 43:
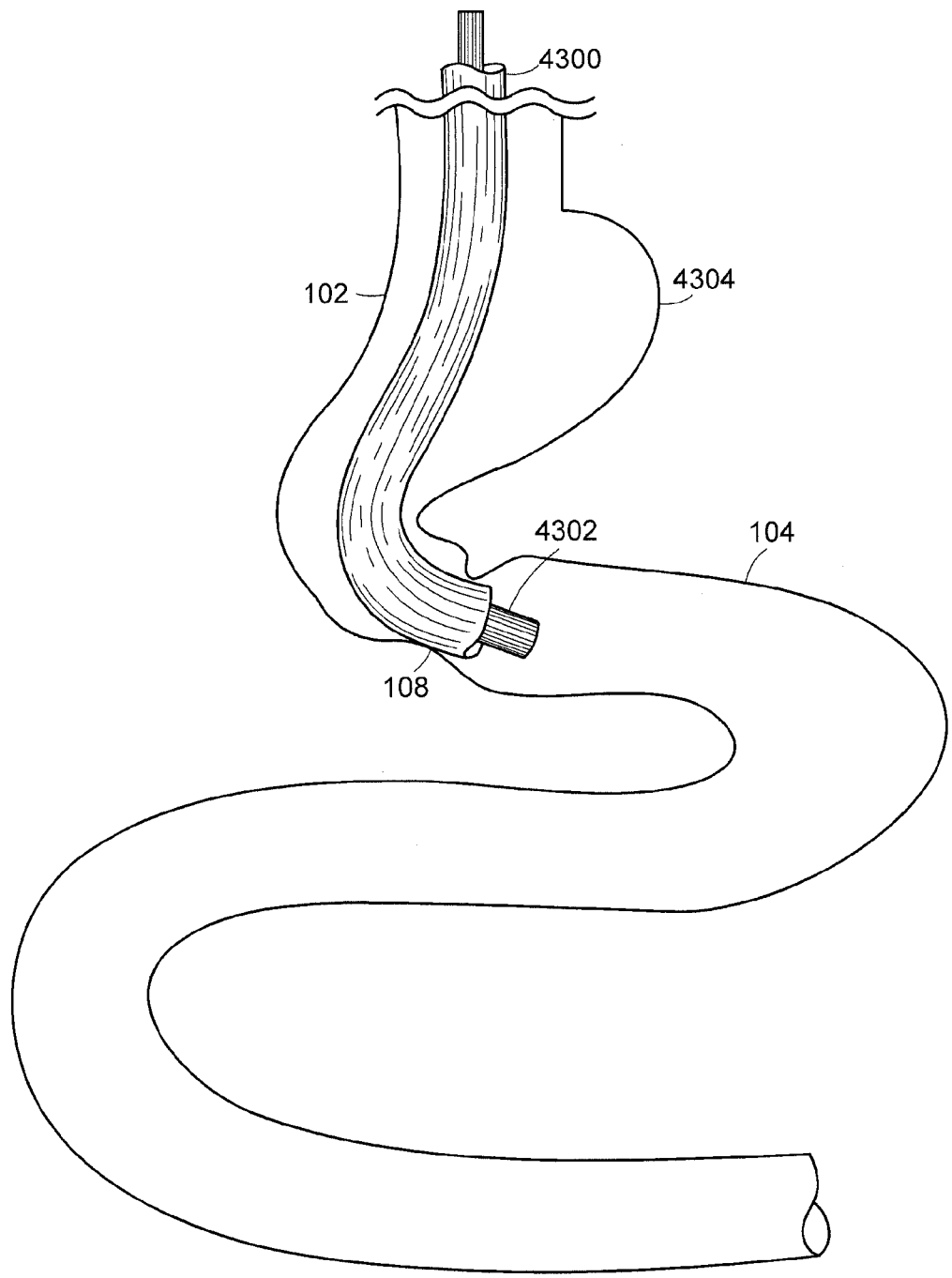
FIG. 43 is a sectional view of a portion of the digestive tract in a body illustrating the position of a gastroscope/guide tube assembly.
Figure 44:
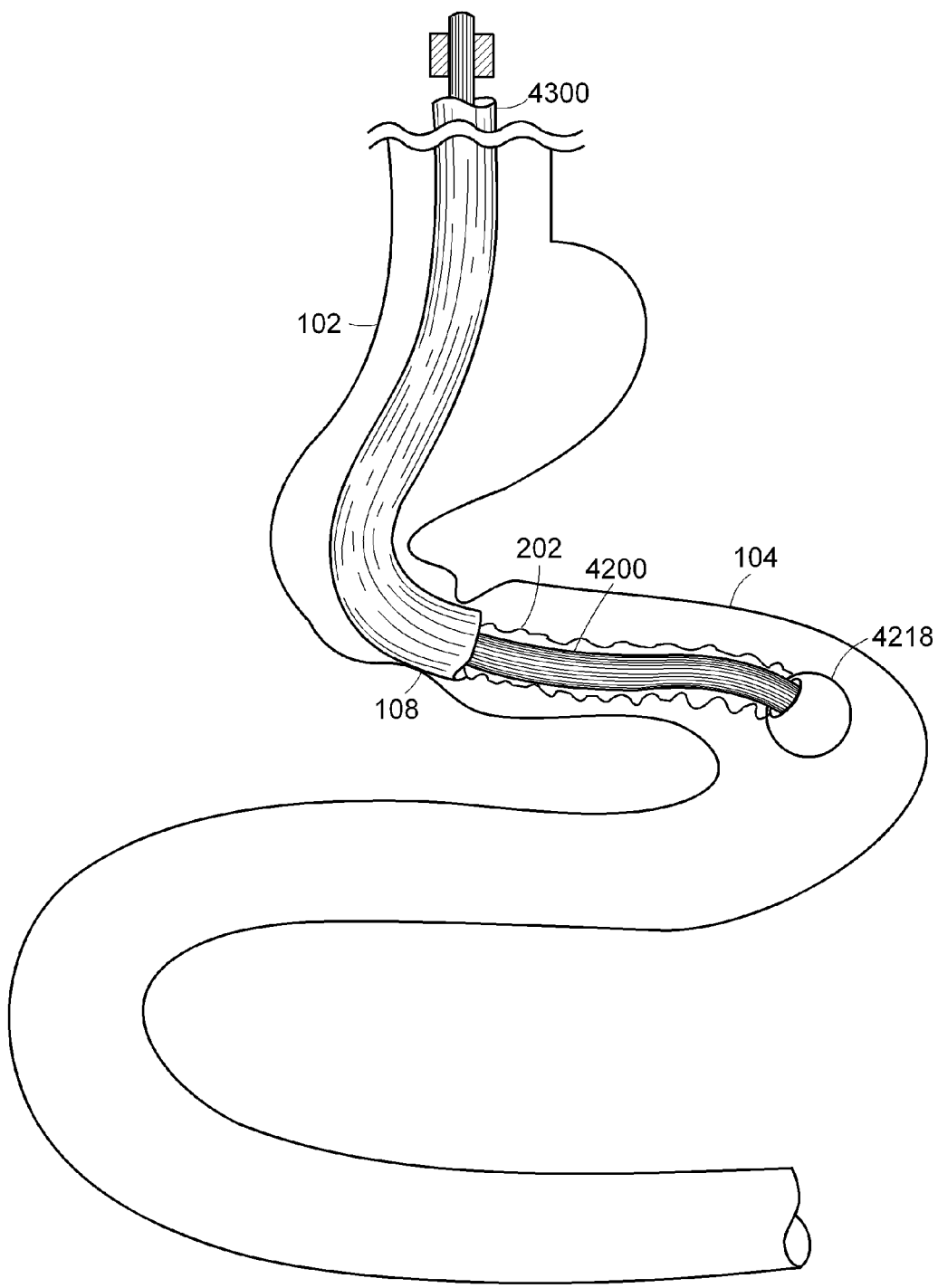
FIG. 44 is a sectional view of a portion of the digestive tract in a body illustrating the distal end of the catheter extending from the distal end of the guide tube 4300.
Figure 45:
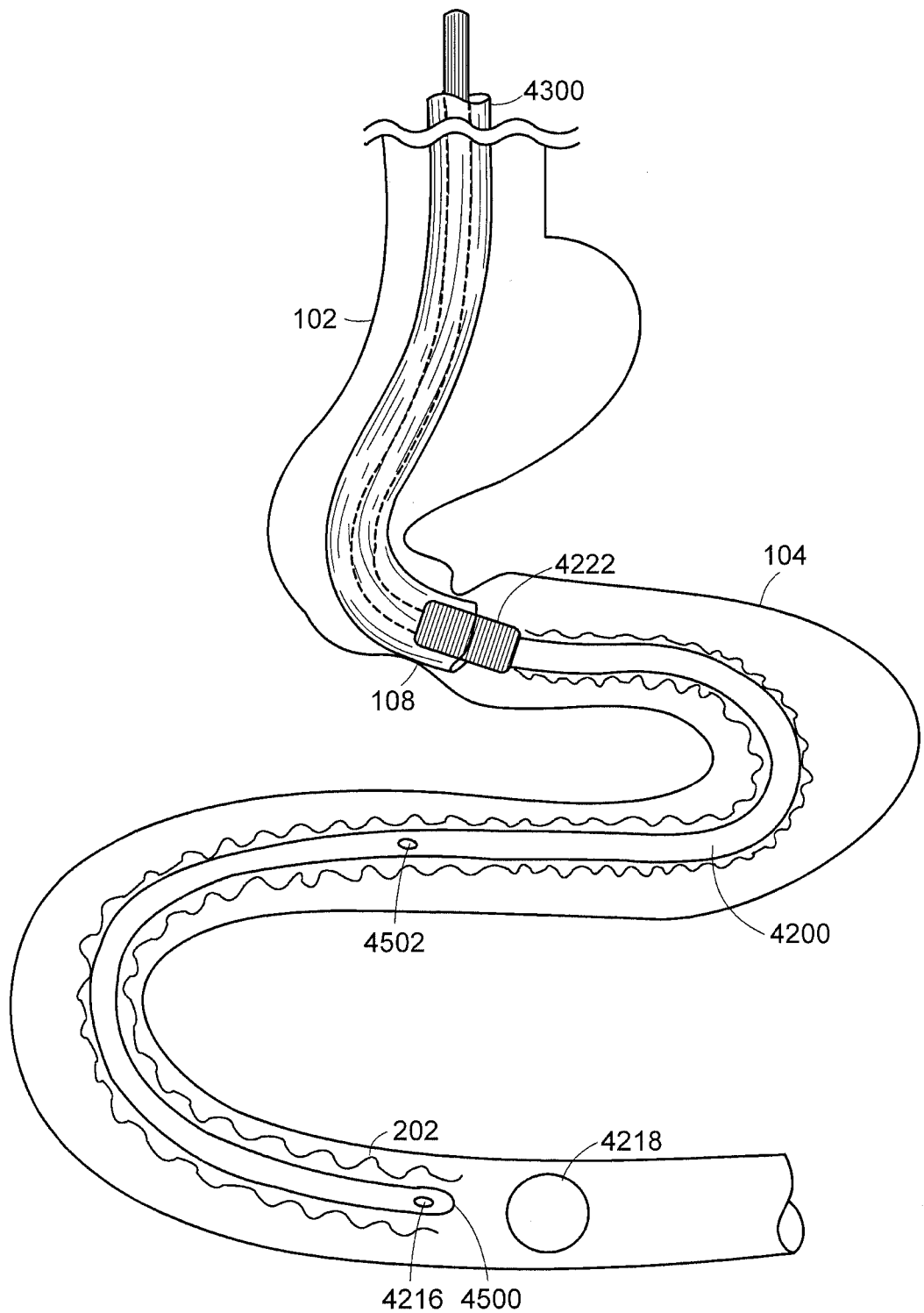
FIG. 45 is a sectional view of a portion of the digestive tract in a body after the gastrointestinal implant device of FIG. 28 has been delivered.

FIGS. 43-45 illustrate the steps for delivery of the gastrointestinal implant device using the low profile catheter described in conjunction with FIGS. 42A-42B. FIG. 43 is a sectional view of a portion of the digestive tract in a body illustrating the position of a gastroscope/guide tube assembly.

The small bowel is accessed endoscopically by passing a semi-rigid tube into the stomach and into the pylorus and proximal duodenum, inflating the bowel with a fluid, preferably water, and then passing a thin, flexible catheter with a large, atraumatic ball tip through the bowel.

A guide tube 4300 is placed over the end of a gastroscope 4302. The guide tube/gastroscope assembly is then placed through the patient's mouth, down the esophagus and into the stomach 102. The assembly is then passed into the pylorus 108 and the duodenum 104.

The guide tube 4300 has an inner diameter of approximately 0.63" (16 mm) and an outer diameter of approximately 0.70" (18 mm). It is approximately 30" (76.2 cm) in length and is made of a flexible polymer such as urethane with a flat wire wrap to provide kink resistance and pushability. The distal end of the guide tube 4300 can have a short, flexible end to minimize trauma to the pylorus 108.

Once in place, fluid is introduced through the channel of the gastroscope 4302 to inflate the intestine distally. Saline or water are preferred but air or carbon dioxide ($CO_2$) can also be used. About 500-1000 cc of fluid is introduced for delivery of a 4' length of sleeve. Shorter sleeves require less fluid because the length of intestine to distend is less. After the fluid is introduced, the gastroscope is removed from the guide tube.

If desired, the gastroscope 4302 can be removed from the guide tube 4300 and a balloon catheter can be introduced to deliver the fluid. The balloon catheter is delivered to the pylorus and inflated to roughly 0.394"-0.591"(10-15 mm) to seal the intestine. A balloon catheter has already been described in conjunction with FIG. 18.

FIG. 44 is a sectional view of a portion of the digestive tract in a body illustrating the distal portion of the catheter assembly extending from the distal portion of the guide tube 4300. The catheter assembly 4250 is advanced through the guide tube 4300 after the gastroscope 4302 has been removed from the guide tube. The ball 4218 at the end of the catheter assembly 4250 provides an atraumatic, leading tip to the catheter such that the catheter follows the contour of the intestines.

FIG. 45 is a sectional view of a portion of the digestive tract in a body after the gastroinstestinal implant device of FIG. 28 has been delivered. The anchor of the gastrointestinal implant device is located inside the delivery tube 4222, which is located in the pylorus 108. A marker on the proximal end of the catheter 4200 aligns with a corresponding marker on the guide tube 4300 when the catheter is fully inserted. Once the gastrointestinal device is in place, the sleeve retention wire 4208 in the catheter 4302 which holds the sleeve 202 in place and also holds the ball 4218 to the distal tip of the catheter can be removed as discussed in conjunction with the catheter system shown in FIGS. 16A-16C. As the sleeve retention wire is pulled back in a distal direction, both the ball 4400 and the distal end of the sleeve 4500 are released. Fluid is then introduced through the third lumen 4206 in the catheter to open the sleeve 202 and expand the sleeve away from the catheter shaft 4200. Water or saline are preferred fluids although air or $CO_2$ can be used. Approximately 100-200 cc is injected. The fluid exits the catheter at a mid point skive hole 4502 and travels in both a distal and proximal direction. Approximately 20 cc of fluid is then injected through the second lumen 4204 and exits the distal skive hole 4216. This fluid lifts the distal end of the sleeve 202 off the inner catheter shaft 4200.

The guide tube 4300 is then removed and the gastroscope re-introduced into the stomach to view the pylorus 108. The proximal anchor is then deployed by pulling back on the delivery tube 4222, which is connected to the proximal end of the catheter. After the anchor is deployed as described in conjunction with FIGS. 31 and 32, the catheter system 4250 is withdrawn from the patient. The catheter 4302 has no edges that could catch on the sleeve 202 as it is pulled back through the stomach 102 and the esophagus because the ball is left behind. This zero profile catheter design is important since it is typically very difficult to withdraw devices from the gastrointestinal tract while leaving catheters or other devices behind.

A method for accessing the small bowel by passing a catheter through the mouth has been described in conjunction with FIGS. 43-45. The low profile catheter can also be used for accessing the small bowel through an incision in the stomach. Instead of delivering the catheter through the top of the stomach as shown in FIG. 43, the catheter is delivered through the stomach, for example, through an incision at position 4304 in FIG. 43. The bowel is filled with a fluid, preferably water, and then the thin, flexible catheter with a large, atraumatic ball tip through the bowel is passed through the bowel as described in conjunction with FIG. 43-45.

Figure 46:
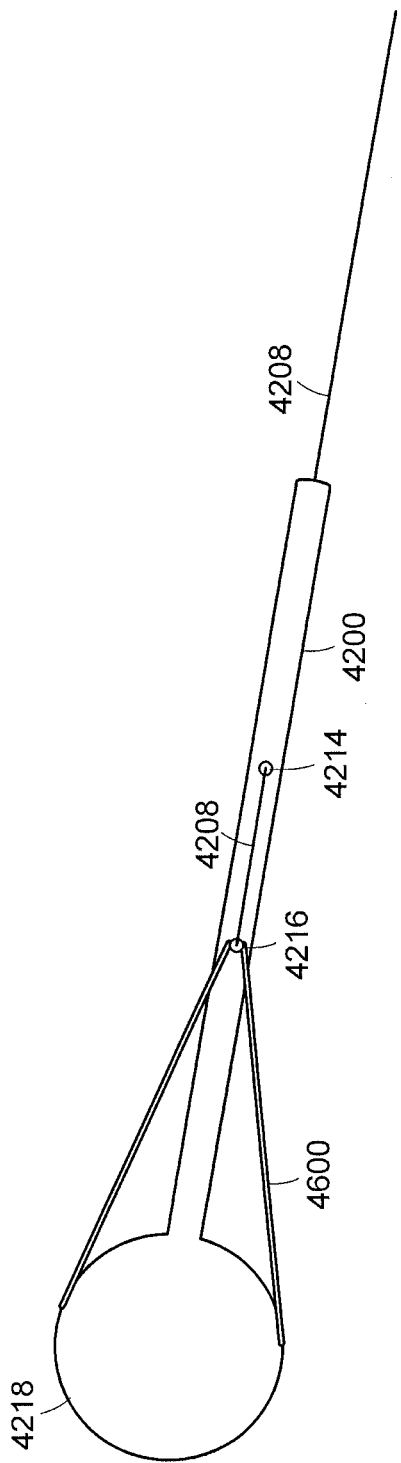
FIG. 46 is a plan view of the distal end of the catheter system illustrating a releasable ball tip mechanism.
Figure 47:
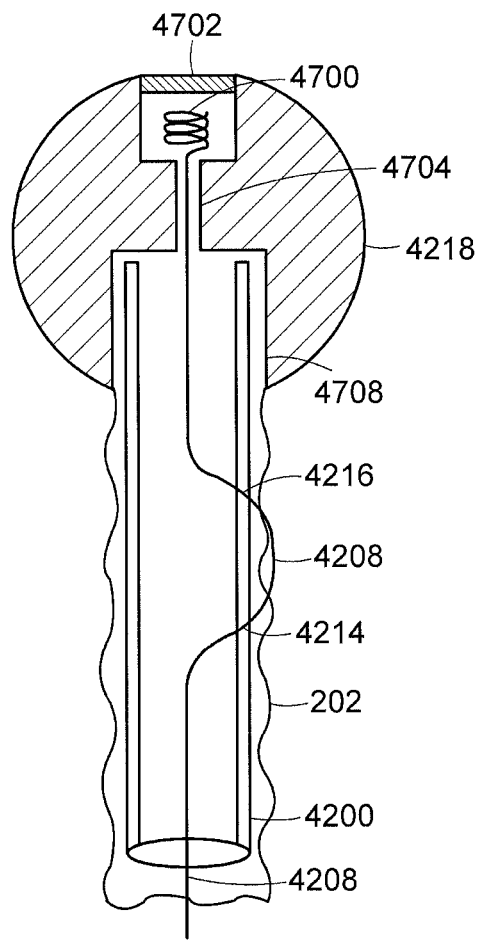
FIG. 47 is a plan view of the distal end of the catheter illustrating an alternative embodiment of a releasable ball tip mechanism.
Figure 48:
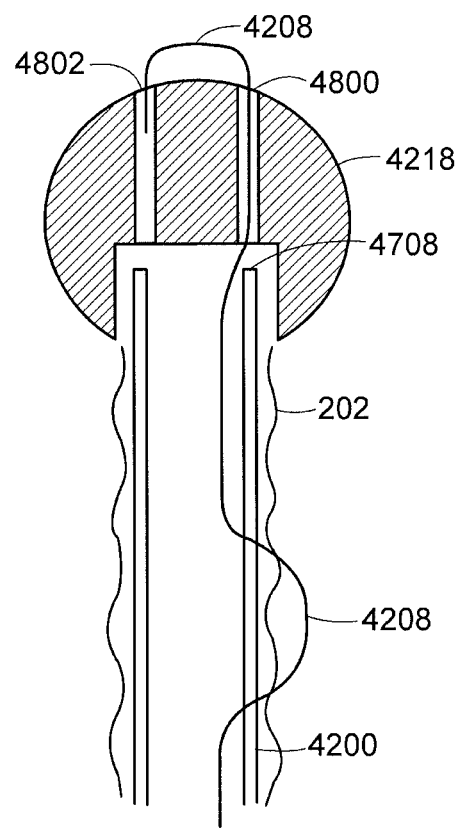
FIG. 48 is a plan view of the distal end of the catheter illustrating yet another embodiment of a releasable ball tip mechanism.

FIGS. 46-48 illustrate embodiments for attaching a releasable spherical shaped element to the distal end of the catheter. FIG. 46 is a plan view of the distal end of the catheter system illustrating a releasable ball tip mechanism. As discussed in conjunction with the catheter system shown in FIG. 42, a sleeve retention wire 4208 travels through second lumen 4204 in the catheter shaft 4200 exits the second lumen 4204 through proximal skive hole 4214 and re-enters the second lumen through distal skive hole 4216.

The ends of wire 4600 are attached to the ball 4218 and the wire 4600 is looped through sleeve retention wire 4208 to hold the ball 4218 at the distal end of the inner shaft 4200 of the catheter. The ball 4218 is released by pulling back on sleeve retention wire 4208 with fitting 4220 (FIG. 42A) until wire 4600 is no longer held by sleeve retention wire 4208. The ball 4218 then falls off the distal end of the inner shaft of the catheter 4200 and exits the body through normal peristalsis through the intestines.

FIG. 47 is a plan view of the distal end of the catheter illustrating an alternative embodiment of a releasable ball tip mechanism. The inner shaft 4200 fits in recess 4706 in the ball 4218. The sleeve retention wire 4208 exits the inner shaft 4200 through proximal skive hole 4214, pierces the sleeve 202 and re-enters the inner shaft 4200 through distal proximal skive hole 4216. The distal end of the sleeve retention wire 4208 is formed into a coil shape 4700 and sits in a pocket 4702 in the ball 4218. The pocket 4702 is connected to the recess 4702 through hole 4704, which is of a smaller diameter than the recess 4702 and the pocket 4700. The distal end of the sleeve retention wire 4208 is annealed so that the sleeve retention wire 4208 can be pulled back in a proximal direction and will straighten out to allow the wire to pass through hole 4704.

FIG. 48 is yet another embodiment of a releasable ball tip mechanism. The inner shaft 4200 fits in recess 4706 in the ball 4218. The sleeve retention wire 4208 exits the inner shaft 4200 through proximal skive hole 4214, pierces the sleeve 202 and re-enters the inner shaft 4200 through distal proximal skive hole 4216.

The ball 4218 includes two holes 4800, 4802 extending from the recess 4706 to the exterior surface of the ball 4218. The distal end of the sleeve retention wire 4208 passes through hole 166 and is looped back into hole 167. As the sleeve retention wire 4208 is pulled proximally, the wire 4218 is pulled back through hole 4802 and then through hold 4800 and the ball 4218 is released from the distal end of the catheter.

Figure 49:
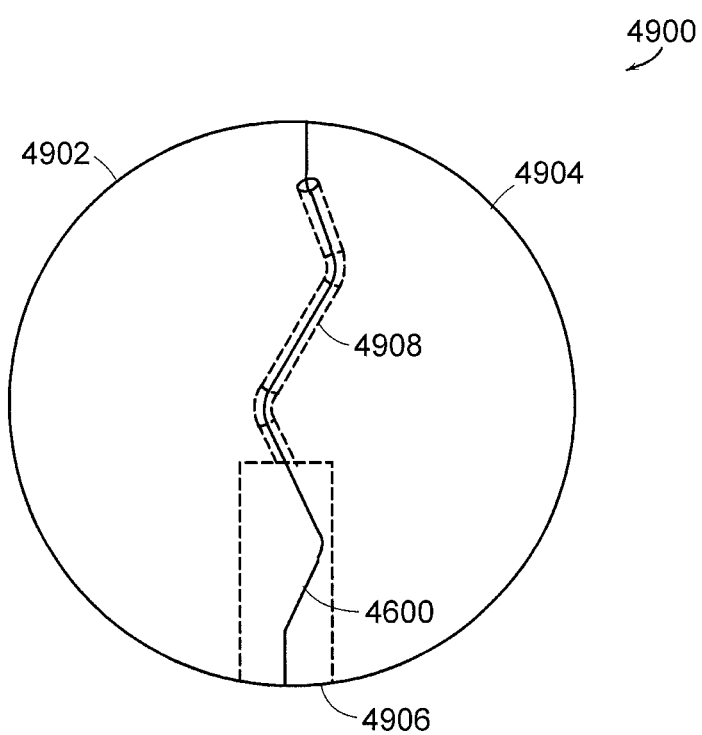
FIG. 49 is a cross sectional view of an alternative embodiment of a solid spherical shaped element.

FIG. 49 is a cross sectional view of an alternative embodiment of a solid spherical shaped element. A ball 4900 is fabricated in two halves, 4902 and 4904. The sleeve retention wire 4006 fits into an S shaped track 4908. The S shape of the track 4908 creates sufficient friction to hold the ball on the end of the catheter during delivery of the gastrointestinal implant device. The sleeve retention wire 4600 fits snugly in the channel 4908 but can be pulled proximally to release the sleeve retention wire 4600 from the ball 4900. The catheter shaft fits in the recess 4906.

Figure 50A:
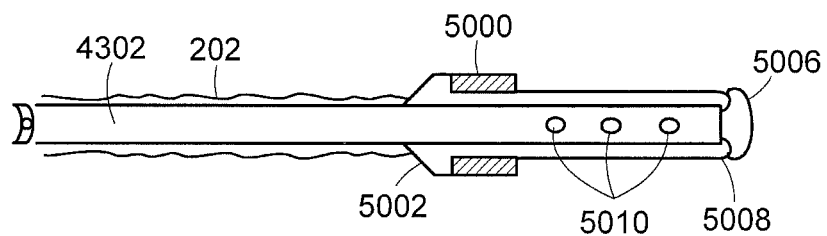
FIG. 50A is a plan view of the distal end of the catheter with an inflatable spherical shaped element.
Figure 50B:
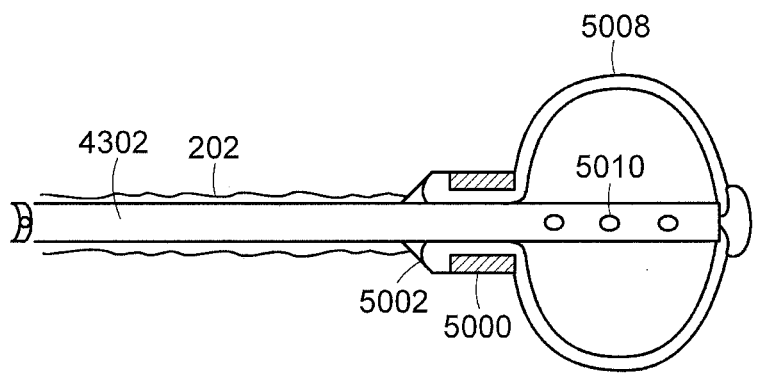
FIG. 50B is a plan view of the distal end of the catheter after the inflatable spherical shaped element has been inflated.

A low profile balloon can be used instead of the ball 4218 at the distal end of the catheter. FIGS. 50A-50B is a plan view of the distal end of the catheter shown in FIG. 44 with a low profile balloon. In the embodiment shown, a low profile balloon replaces the ball at the distal end of the catheter shown in FIG. 44. FIG. 50A is a plan view of the distal end of the catheter with an inflatable spherical shaped element. FIG. 50B is a plan view of the distal end of the catheter after the inflatable spherical shaped element has been inflated;

Referring to FIG. 50A, a silicone or latex sleeve 202 is attached to the distal end of the catheter shaft 4302. Filling holes 5010 connect with the inner lumen of the catheter to provide a passage for inflation of an inflatable spherical shaped element (balloon) 5008. The balloon 5008 is attached to the shaft 4302 with a metal band 5000 that has a tapered proximal transition 5002 to minimize edges that could catch on the sleeve 202 after delivery of the sleeve 202. The metal band 5000 is about 0.003-0.005" (0.076-0.127 mm) thick. The balloon 5008 can be thin wall molded, tubular polyurethane or silicone. The balloon is stored along the distal catheter shaft 4302 with the distal end pushed into the lumen of the catheter shaft and attached to the catheter shaft 4302 with a plug 5006 to keep the balloon from expanding beyond the tip of the catheter.

FIG. 50B illustrates the distal end of the catheter 4302 after the balloon 5002 has been expanded into a spherical shape. The balloon is expanded by fluid, which flows through the catheter shaft and enters the balloon 5008 through the fluid passage holes from the catheter shaft. The plug 5006 at the end of the catheter shaft ensures that the balloon acts like the ball shown in the embodiment in FIG. 50 by limiting expansion of the balloon beyond the tip of the catheter and the plug also provides some lateral strength to the balloon. By replacing the ball with a balloon at the distal end of the catheter, the distal tip is more stable for axial compression. Also, the catheter will not deflect with side loading.

The further one tries to pass a device into the intestine, the more difficult it is since friction and tortuosity increase. FIG. 51 is a plan view of an alternative delivery system for delivering a gastrointestinal implant device. The delivery system enables delivery of a long sleeve into the intestine and includes a distal pill with folded sleeve material inside. Peristalsis carries the pill distal in the intestine, causing the sleeve material to unfurl.

The delivery system is described for delivering the embodiment of the gastrointestinal device described in conjunction with FIG. 28. However, the delivery system is not limited to the delivery of a distal section of the sleeve for this embodiment of the gastrointestinal implant device. As described in conjunction with FIG. 28, the gastrointestinal device includes a proximal ring 2802, a distal ring 2803 and a sleeve 202. The proximal section of the sleeve is fully deployed and some amount of the distal section of sleeve 202 is packed into a pill 5100.

The gastrointestinal implant device is delivered as previously described into the proximal intestines. Once deployed in the intestines, peristalsis from the natural activity of the intestine pulls the pill 5100 distally through the intestine. As the pill is pulled distally, the distal section of the sleeve 202 pulls out of the pill and deploys straight in the intestine. Peristalsis pulls the pill through the remainder of the intestines and the pill finally exits the body.

A one-foot length of sleeve material can be packed into a pill with length of 1" (25.4 mm) and diameter of 0.47" (12 mm). Therefore, if one only wishes to pass the catheter 2 feet into the intestine for delivery of the gastrointestinal device, the pill 5100 enables a 3 foot sleeve to be delivered with the additional 1' distal section of the 3-foot sleeve delivered in the pill 5100.

Figure 52:
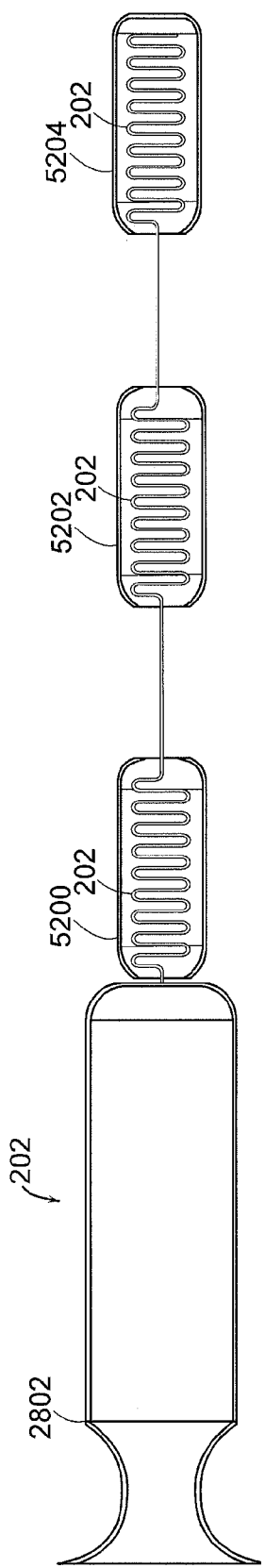
FIG. 52 is a plan view of another embodiment of the delivery mechanism shown in FIG. 51.

FIG. 52 is a plan view of another embodiment of the delivery mechanism shown in FIG. 51. The delivery mechanism enables delivery of a long sleeve into the intestine and includes encapsulated sleeve materials formed into pill shapes. Each pill dissolves in the body at different rates enabling the sleeve to be pulled distally by peristalsis as it unfolds once the pill covering dissolves.

The delivery mechanism is shown for delivery of the gastrointestinal implant device described in conjunction with FIG. 28. The first section of the sleeve 202 is fully deployed after the gastrointestinal implant device has been delivered into the proximal intestine as previously described. A plurality of distal sections of the sleeve 202 are coated to form a plurality of dissolvable pills 5200, 5202, 5204. The coatings applied to form each respective pill 5200, 5202, 5204 are made of a dissolvable material, with each coating tailored to dissolve at different times depending on the polymer make up and the environment. Each pill 5200, 5202, 5204 is carried distally by peristalsis. The coating on the first pill 5200 is selected to dissolve first. After the coating on the first pill 5200 has dissolved, the second and third pills 5202 and 5204 pull the compacted sleeve 202 distally. The coating on the second pill 5202 dissolves next, as the third pill 5204 pulls the sleeve more distally. Finally, the coating on the third pill 5204 dissolves and the sleeve 202 is fully deployed. The plurality of dissolvable pills enables the ultimate delivery of many feet of sleeve material with the simpler delivery of only an initial 1-2 foot section of the sleeve into the proximal intestine. As described in conjunction with the embodiment shown in FIG. 51, a one-foot length of sleeve material can be packed into a pill with length of 1" (25.4 mm) and diameter of 0.47" (12 mm).

A number of biodegradable materials may be used for the coatings on the pills including polyethylene glycols (PEG), polylactic acids (PLA) and polycaprolactones (PCL). These materials are made in formable resins or in liquids that can be converted to solids through various types of chemical and photochemical reactions. These materials break down into chemicals that are safe to internal tissues. These resins are made biodegradable by formulating a base molecule with a hydrolytically unstable link within the base chain.

For example, PEG is made biodegradable by incorporating lactic acid into the base chain. One end of the lactide molecule forms a link that will break down rapidly in the presence of water. One means of controlling the rate of degradation is by varying the number of lactide elements within the base chain. The greater the number, the faster the chain will break down. Additionally, the percent solids or density of the resulting solid is varied to alter degradation rates. Denser materials take longer to break down. Also, hydrolytically unstable bonds break down faster in elevated pH environments. Such an environment occurs naturally within the small intestines, on the outside of the sleeve where bile and bicarbonates are deposited.

Figure 53C:
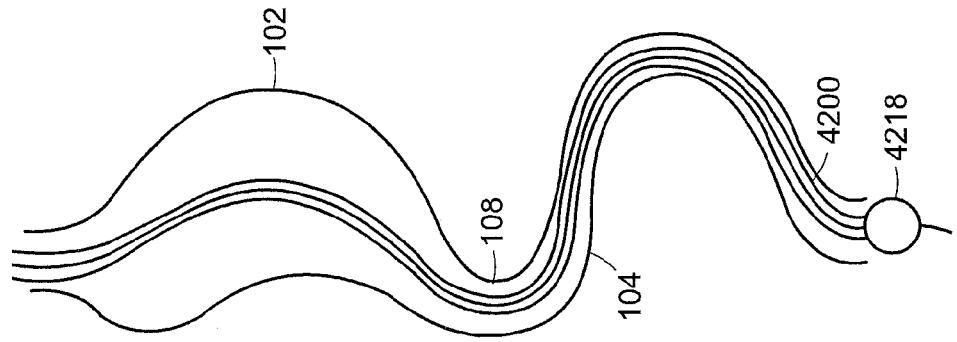
FIGS. 53A-53C illustrate a method for delivering an alternate embodiment of the catheter system 4250 having a central lumen for placement over a guide wire.
Figure 53B:
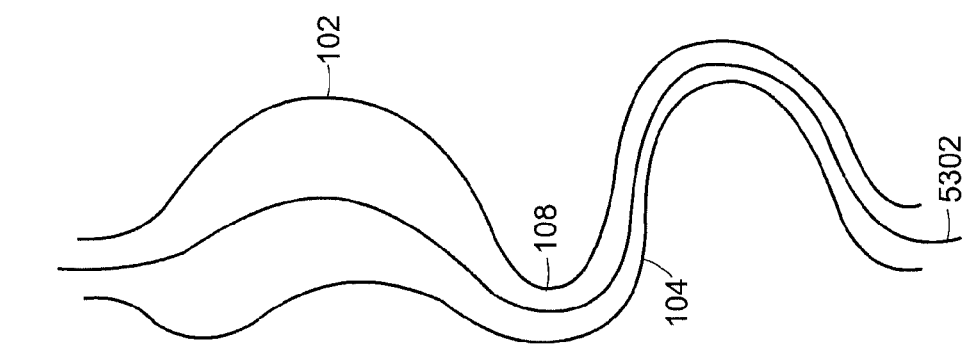
Figure 53A:
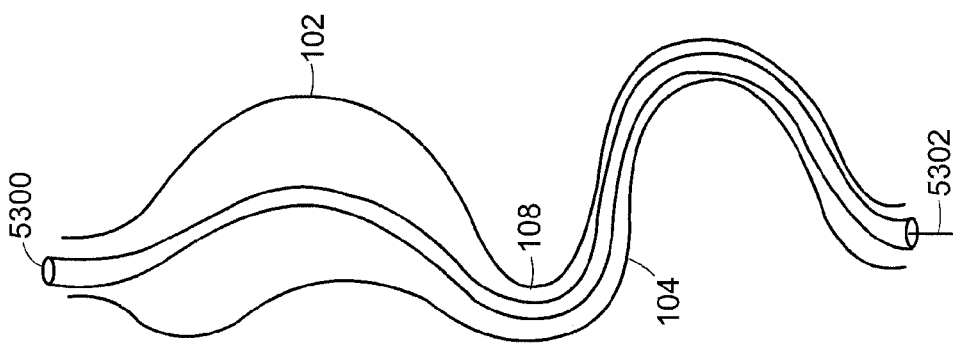

FIGS. 53A-53C illustrate a method for delivering an alternate embodiment of the catheter system 4250 having a central lumen for placement over a guide wire. FIG. 53A is a sectional view of a portion of the digestive tract in a body illustrating an enteroscope 5300 extending through the stomach, through the pylorus 104 to the duodenum 104. A guide wire 5302 is then passed through the enteroscope 5300. After the guide wire has been passed through the enteroscope 5300 is removed. FIG. 53B is a sectional view of a portion of the digestive tract in a body illustrating the guide wire 5302 extending through the stomach 104 and the duodenum 104 after the enteroscope 5300 has been removed. The catheter system follows a guide wire 5302 through the esophagus and the stomach to the pylorus portion 108 of the stomach 102. FIG. 53C is a sectional view of a portion of the digestive tract in a body illustrating the catheter extending through the stomach 102 and duodenum 104 over the guide wire 5300. After the gastrointestinal implant device has been delivered, the catheter 4200 is pulled back through the stomach. After the catheter has been removed, the guide wire 5302 is pulled back through the intestines and the stomach 102.

While this invention has been particularly shown and described with references to preferred embodiments thereof, it will be understood by those skilled in the art that various changes in form and details may be made therein without departing from the scope of the invention encompassed by the appended claims.

What is claimed is:

1. A delivery apparatus for delivering a gastrointestinal device, the apparatus comprising:
    a gastrointestinal device comprising a tube;
    a shaft extending through the tube, the shaft configured to pass through a length of the intestines and to deliver the gastrointestinal device;
    an atraumatic element, distinct from the gastrointestinal device, distal to and releasably coupled to a distal tip of the shaft; and
    a release mechanism that releasably engages the atraumatic element to retain the atraumatic element on the distal tip of the shaft, the release mechanism comprising a moveable element, the atraumatic element being released from the distal tip of the shaft and the moveable element by movement of the moveable element, the shaft including first and second holes near its distal tip, the moveable element exiting the shaft via the first hole and re-entering the shaft via the second hole.

2. The apparatus according to claim 1, wherein the shaft and gastrointestinal device are disposed within a guide tube, the guide tube configured to guide movement of the shaft and gastrointestinal device.

3. The apparatus according to claim 2, wherein the guide tube guides the passage of the shaft and gastrointestinal device through a length of the stomach.

4. The apparatus according to claim 1, wherein the atraumatic element is remotely releasable.

5. The apparatus according to claim 4, wherein the atraumatic element comprises a ball.

6. The apparatus according to claim 4, wherein the atraumatic element is inflatable.

7. The apparatus according to claim 1, wherein the atraumatic element is attached to a loop which is held by the release mechanism.

8. The apparatus according to claim 1, wherein the atraumatic element is larger in diameter than the shaft.

9. The apparatus according to claim 8, wherein the atraumatic element is 0.25 inches to 0.75 inches in diameter.

10. The apparatus according to claim 1, wherein the shaft is a catheter having a lumen therein.

11. The apparatus according to claim 1, wherein the shaft has a minimum bend radius of less than 0.5 inches without kinking.

12. The apparatus according to claim 1, wherein the moveable element extends along a first lumen in the shaft and a wire extends along a second lumen in the shaft.

13. The apparatus according to claim 1, wherein the moveable element extends between the first and second holes through a loop attached to the atraumatic element.

14. The apparatus according to claim 1, wherein the moveable element extends along a length of the inner shaft and is longitudinally moveable within the shaft.

15. The apparatus according to claim 1, wherein the moveable element is a wire.

16. The apparatus according to claim 1, wherein the atraumatic element is released by movement of the moveable element away from the atraumatic element.

17. A method of delivering a gastrointestinal device, the method comprising:
    passing a shaft through a length of the intestines, the shaft having an atraumatic element, distinct from the gastrointestinal device, distal to and releasably coupled to a distal tip of the shaft and having a release mechanism that releasably engages the atraumatic element to retain the atraumatic element on the distal tip of the shaft;
    releasing the atraumatic element from the shaft and the release mechanism, the release mechanism comprising a moveable element, the atraumatic element being released from the distal tip of the shaft and the moveable element by movement of the moveable element, the shaft including first and second holes near its distal tip, the moveable element exiting the shaft via the first hole and re-entering the shaft via the second hole; and delivering the gastrointestinal device over the shaft, the gastrointestinal device comprising a tube extending over the shaft.

18. The method according to claim 17, wherein the shaft and gastrointestinal device are disposed within a guide tube, the guide tube configured to guide movement of the shaft and gastrointestinal device.

19. The method according to claim 18, wherein the guide tube guides the passage of the shaft and gastrointestinal device through a length of the stomach.

20. The method according to claim 17, wherein the shaft is disposed within a lumen of the gastrointestinal device.

21. The method according to claim 17, wherein the atraumatic element is remotely releasable.

22. The method according to claim 17, wherein the atraumatic element comprises a ball.

23. The method according to claim 17, wherein the atraumatic element is inflatable.

24. The method according to claim 17, wherein the atraumatic element is attached to a loop which is held by the release mechanism.

25. The method according to claim 17, wherein the atraumatic element is larger in diameter than the shaft.

26. The method according to claim 25, wherein the atraumatic element is 0.25 inches to 0.75 inches in diameter.

27. The method according to claim 17, wherein the shaft is a catheter having a lumen therein.

28. The method according to claim 17, wherein the shaft has a minimum bend radius of less than 0.5 inches without kinking.

29. The method according to claim 17, wherein the moveable element extends along a first lumen in the shaft and a wire extends along a second lumen in the shaft.

30. The method according to claim 17, wherein the moveable element extends between the first and second holes through a loop attached to the atraumatic element.

31. The method according to claim 17, wherein the moveable element extends along a length of the inner shaft and is longitudinally moveable within the shaft.

32. The method according to claim 17, wherein the atraumatic element is released by movement of the moveable element away from the atraumatic element.

33. The method according to claim 17, wherein the gastrointestinal device is delivered through an incision in the stomach.

* * * * *